(12) United States Patent
Corona et al.

(10) Patent No.: US 12,078,634 B2
(45) Date of Patent: *Sep. 3, 2024

(54) BROAD SPECTRUM KINASE BINDING AGENTS

(71) Applicant: Promega Corporation, Madison, WI (US)

(72) Inventors: Cesear Corona, Paso Robles, CA (US); Poncho Meisenheimer, San Luis Obispo, CA (US); Matthew Robers, Madison, WI (US); James Vasta, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/819,784

(22) Filed: Aug. 15, 2022

(65) Prior Publication Data

US 2023/0194515 A1 Jun. 22, 2023

Related U.S. Application Data

(63) Continuation of application No. 16/426,982, filed on May 30, 2019, now Pat. No. 11,442,063.

(60) Provisional application No. 62/677,956, filed on May 30, 2018.

(51) Int. Cl.

| | | |
|---|---|---|
| C07D 239/48 | (2006.01) | |
| G01N 1/34 | (2006.01) | |
| G01N 33/543 | (2006.01) | |
| G01N 33/573 | (2006.01) | |
| G01N 21/64 | (2006.01) | |
| G01R 33/56 | (2006.01) | |
| G01T 1/164 | (2006.01) | |

(52) U.S. Cl.
CPC ..... *G01N 33/54353* (2013.01); *C07D 239/48* (2013.01); *G01N 1/34* (2013.01); *G01N 33/573* (2013.01); *G01N 21/6428* (2013.01); *G01N 2021/6439* (2013.01); *G01R 33/5601* (2013.01); *G01T 1/1642* (2013.01)

(58) Field of Classification Search
CPC .......... C07D 239/48; G01N 33/54353; G01N 33/576; G01N 1/34; G01N 21/6428; G01N 2021/6439; G01R 33/5601; G01T 1/1642

See application file for complete search history.

(56) References Cited

U.S. PATENT DOCUMENTS

| | | | |
|---|---|---|---|
| 4,810,636 A | 3/1989 | Corey | |
| 4,812,409 A | 3/1989 | Babb et al. | |
| 6,162,931 A | 12/2000 | Gee et al. | |
| 6,670,114 B1 | 12/2003 | Maertens et al. | |
| 6,670,144 B1 | 12/2003 | Craig et al. | |
| 7,238,842 B2 | 7/2007 | Wood et al. | |
| 7,425,436 B2 | 9/2008 | Darzins et al. | |
| 7,429,472 B2 | 9/2008 | Darzins et al. | |
| 7,625,903 B2* | 12/2009 | Johnson | C07D 413/12 544/295 |
| 7,829,350 B2 | 11/2010 | Josephson et al. | |
| 7,867,726 B2 | 1/2011 | Wood et al. | |
| 7,884,098 B2* | 2/2011 | Axten | C07D 241/20 544/323 |
| 8,557,970 B2 | 10/2013 | Encell et al. | |
| 8,669,103 B2 | 3/2014 | Binkowski et al. | |
| 8,901,120 B2 | 12/2014 | Bearss et al. | |
| 9,056,885 B2 | 6/2015 | Kirkland et al. | |
| 2003/0092029 A1 | 5/2003 | Josephson et al. | |
| 2011/0281289 A1 | 11/2011 | Cutillas et al. | |
| 2014/0323346 A1* | 10/2014 | Daly | C07K 1/22 435/6.13 |

FOREIGN PATENT DOCUMENTS

| | | |
|---|---|---|
| WO | WO 2014/093677 | 6/2014 |
| WO | WO 2018033556 | 2/2018 |

OTHER PUBLICATIONS

Vasta, Cell Chemical Biology, vol. 25, 206-214, 2018. (Year: 2018).*
Vasta et al. Quantitative, Wide-Spectrum Kinase Profiling in Live Cells for Assessing the Effect of Cellular ATP on Target Engagement, Cell Chemical Biology, Feb. 15, 2018, 25, pp. 206-214, https://doi.org/10.1016/j.chembiol.2017.10.010.
Japanese Office Acton, Japanese Patent Application No. 2020-566944, mailed Jun. 15, 2023, 13 pgs.
Crivat et al., Imaging proteins inside cells with fluorescent tags. Trends Biotechnol. Jan. 2012;30(1):8-16.
Dhanasekaran et al., Signaling by dual specificity kinases. Oncogene. Sep. 17, 1998;17(11 Reviews):1447-55.
Gautier et al., An engineered protein tag for multiprotein labeling in living cells. Chem Biol. Feb. 2008;15(2):128-36.
Manning et al., The protein kinase complement of the human genome. Science. Dec. 6, 2002;298(5600):1912-34.
Patterson et al., Finding the Right (Bioorthogonal) Chemistry. ACS Chem Biol. Mar. 21, 2014;9(3):592-605.
Zhang et al., Characterization of the novel broad-spectrum kinase inhibitor CTx-0294885 as an affinity reagent for mass spectrometry-based kinome profiling. J Proteome Res. Jul. 5, 2013;12(7):3104-16.
International Search Report and Written Opinion, PCT/US19/34675, mailed Aug. 12, 2019, 9 pgs.
Office Action for European Patent Application No. 19812069.3, dated Feb. 7, 2024 (5 pages).

* cited by examiner

*Primary Examiner* — D Margaret M Seaman
(74) *Attorney, Agent, or Firm* — Casimir Jones, SC; David W. Staple

(57) ABSTRACT

Provided herein are compounds that are broad-spectrum protein kinase binding agents, detectable tracers comprising such compounds, and method of use thereof for the detection of protein kinases.

14 Claims, 25 Drawing Sheets
(24 of 25 Drawing Sheet(s) Filed in Color)
Specification includes a Sequence Listing.

FIG. 1A

| Tracer | CC-1804 | CC-1817 | CC-1294 |
|---|---|---|---|
| Chemotype | Benzamide | Benzamide | Methylbenzamide |
| Linker | *para*-pip-O4 | *meta*-pip-O4 | *para*-pip-O4 |
| [Tracer], uM | 0.5 | 0.5 | 1 |
| Mode | Live | Live | Live |
|  | Fold Change | Fold Change | Fold Change |
| Kinases Above 1.4 fold | 300 | 322 | 179 |
| Kinases Above 2-fold | 226 | 222 | 108 |
| Kinases above 3-fold | 153 | 154 | 68 |
| Percent Relative to Total | 50.4 | 54.1 | 30.1 |
| Percent Relative to Total | 38.0 | 37.3 | 18.2 |
| Percent Relative to Total | 25.7 | 25.9 | 11.4 |
| Percent Relative to Hits | 84.0 | 90.2 | 50.1 |
| Percent Relative to Hits | 63.3 | 62.2 | 30.3 |
| Percent Relative to Hits | 42.9 | 43.1 | 19.0 |

Red cells = data not relevant due to poor kinase expression

FIG. 1B

| Total Kinase Entities | Tracer | 1804 | 1817 | 1294 |
|---|---|---|---|---|
| 595 | | | | |
| | Linker | O4 | O4 | O4 |
| Kinase Entities Hit > 1.4-fold | [Tracer], uM | 0.5 | 0.5 | 1 |
| 46 | Mode | Live | Live | Live |
| | Hit Count > 1.3999 | 7600 Fold Change | 7520 Fold Change | K5 Fold Change |
| STK11 | 3 | 4.06 | 5.98 | 2.40 |
| STK16 | 3 | 17.08 | 30.67 | 11.69 |
| STK17B | 2 | 2.07 | 3.21 | 1.12 |
| STK24 | 1 | 1.30 | 3.13 | 1.17 |
| STK25 | 1 | 1.13 | 1.52 | 1.03 |
| STK26 | 1 | 1.23 | 4.22 | 1.04 |
| STK3 | 2 | 2.15 | 1.85 | 1.38 |
| STK32A | 3 | 1.92 | 2.33 | 1.72 |
| STK32B | 3 | 3.31 | 5.96 | 2.53 |
| STK33 | 3 | 3.04 | 3.07 | 2.16 |
| STK35 | 3 | 4.37 | 4.84 | 1.67 |
| STK36 | 3 | 10.13 | 4.40 | 3.59 |
| STK38 | 3 | 6.02 | 2.96 | 1.54 |
| STK38L | 2 | 3.56 | 2.30 | 1.31 |
| STK4 | 3 | 4.11 | 3.70 | 1.75 |
| STYK1 | 2 | 1.61 | 2.50 | 1.15 |
| TAOK1 | 1 | 1.02 | 1.65 | 1.04 |
| TAOK2 | 1 | 1.18 | 1.62 | 1.02 |
| TAOK3 | 1 | 1.08 | 1.99 | 1.03 |
| TBK1 | 3 | 9.49 | 12.40 | 7.09 |

| | | | | |
|---|---|---|---|---|
| TEC | 3 | 6.63 | 3.26 | 6.55 |
| TEK | 3 | 27.54 | 57.59 | 19.77 |
| TESK1 | 1 | 1.37 | 2.25 | 1.17 |
| TESK2 | 1 | 1.09 | 1.53 | 1.06 |
| TGFBR1 | 1 | 1.29 | 1.45 | 1.31 |
| TIE1 | 3 | 11.29 | 10.02 | 7.14 |
| TK2 | 2 | 1.54 | 1.72 | 1.19 |
| TLK1 | 1 | 3.17 | 1.37 | 1.10 |
| TLK2 | 1 | 4.00 | 1.33 | 1.05 |
| TNK1 | 3 | 9.62 | 9.98 | 5.82 |
| TNK2 | 3 | 9.31 | 6.53 | 3.93 |
| TNNI3K | 3 | 3.62 | 3.45 | 1.71 |
| TSSK1B | 2 | 1.70 | 2.92 | 1.34 |
| TTK | 2 | POOR FIT | 3.40 | 2.84 |
| TXK | 3 | 2.80 | 3.15 | 3.12 |
| TYK2 | 3 | 3.65 | 1.74 | 1.77 |
| TYK2JH1 | 2 | 2.74 | 1.57 | 1.05 |
| TYK2JH2 | 3 | 6.69 | 1.93 | 1.46 |
| TYRO3 | 3 | 2.01 | 1.56 | 2.18 |
| UHMK1 | 2 | 1.80 | 1.53 | 1.10 |
| ULK1 | 3 | 17.31 | 16.98 | 13.29 |
| ULK2 | 3 | 12.59 | 8.64 | 3.70 |
| ULK3 | 3 | 7.05 | 7.76 | 2.92 |
| WEE1 | 3 | 7.00 | 7.53 | 4.77 |
| WEE2 | 3 | 2.33 | 2.79 | 2.89 |
| YES1 | 3 | 1.65 | 1.55 | 1.85 |

| Total Kinase Entities 595 | Tracer | 1804 | 1817 | 1294 |
|---|---|---|---|---|
|  | Linker | O4 | O4 | O4 |
| Kinase Entities Hit > 1.4-fold 359 | [Tracer], uM | 0.5 | 0.5 | 1 |
|  | Mode | Live | Live | Live |
|  | Hit Count > 1.3999 | 7600 Fold Change | 7520 Fold Change | K5 Fold Change |
| AAK1 | 3 | 26.14 | 12.80 | 13.04 |
| AAK1 | 3 | 26.14 | 12.80 | 13.04 |
| ABL1 | 1 | 1.46 | 1.32 | 1.33 |
| ABL1(H396P) | 3 | 1.98 | 1.50 | 1.81 |
| ABL1(M351T) | 2 | 1.51 | 1.37 | 1.48 |
| ABL1(Q252H) | 3 | 2.04 | 1.70 | 1.75 |
| ABL1(T315I) | 3 | 1.99 | 1.53 | 1.91 |
| ABL1(Y253F) | 1 | 1.47 | 1.33 | 1.38 |
| ABL2 | 3 | 2.71 | 3.17 | 1.97 |
| ACVR1 | 1 | 1.31 | 1.43 | 1.32 |
| ACVR1B | 1 | 1.34 | 1.45 | 1.36 |
| ADCK1 | 2 | 1.86 | 2.04 | 1.19 |
| ADCK2 | 1 | 1.12 | 1.50 | 1.06 |
| ADCK5 | 2 | 1.82 | 2.76 | 1.07 |
| ADK | 2 | 1.51 | 2.06 | 1.23 |
| ADPGK | 2 | 1.41 | 2.02 | 1.05 |
| AKT1 | 3 | 1.92 | 1.41 | 1.53 |
| AKT2 | 3 | 2.38 | 1.95 | 1.65 |
| AKT3 | 1 | 1.62 | 1.36 | 1.28 |
| ALK | 3 | 2.02 | 2.42 | 1.53 |
| ALK(C1156Y) | 3 | 2.02 | 2.06 | 1.44 |

FIG. 1C (cont.)

| | | | | |
|---|---|---|---|---|
| ALK(L1196M) | 3 | 2.26 | 3.03 | 1.62 |
| AURKA | 3 | 9.66 | 13.85 | 7.80 |
| AURKB | 3 | 15.19 | 21.28 | 5.15 |
| AURKC | 3 | 18.93 | 28.20 | 7.08 |
| AXL | 3 | 2.95 | 3.44 | 2.67 |
| BCKDK | 2 | 1.50 | 1.61 | 1.06 |
| BMP2K | 3 | 15.64 | 8.44 | 4.21 |
| BMPR1A | 1 | 1.22 | 1.44 | 1.09 |
| BMPR1B | 1 | 1.23 | 1.51 | 1.20 |
| BMX | 3 | 3.80 | 3.22 | 2.77 |
| BRSK1 | 3 | 11.01 | 4.91 | 4.59 |
| BRSK2 | 3 | 5.63 | 2.79 | 2.10 |
| BTK | 3 | 6.48 | 7.60 | 7.11 |
| BUB1 | 1 | 1.90 | 1.19 | 1.28 |
| CAMK1 | 2 | 2.19 | 3.10 | 1.12 |
| CAMK1D | 1 | 1.29 | 2.78 | 1.07 |
| CAMK1G | 2 | 1.45 | 4.61 | 1.05 |
| CAMK2A | 2 | 4.73 | 2.97 | 0.95 |
| CAMK2B | 2 | 1.72 | 1.68 | 1.09 |
| CAMK2D | 2 | 4.25 | 2.38 | 1.05 |
| CAMK2G | 2 | 5.96 | 3.44 | 0.99 |
| CASK | 2 | 1.72 | 1.16 | 1.46 |
| CDC42BPG | 1 | 1.24 | 1.58 | 1.05 |
| CDC7 | 2 | 1.48 | 1.80 | 1.06 |
| CDK1 + B1 | 3 | 2.50 | 4.14 | 1.56 |
| CDK1 + E1 | 3 | 2.63 | 5.04 | 1.58 |
| CDK10 + L2 | 2 | 3.25 | 1.67 | N/A |

FIG. 1C (cont.)

| | | | | |
|---|---|---|---|---|
| CDK13 + K | 1 | 1.40 | 1.32 | 1.06 |
| CDK14 + Y | 2 | 4.03 | 1.51 | 1.37 |
| CDK15 + Y | 3 | 3.35 | 2.33 | 2.44 |
| CDK16 + Y | 3 | 6.24 | 2.47 | 1.90 |
| CDK17 + Y | 3 | 8.78 | 2.80 | 2.15 |
| CDK18 + Y | 3 | 10.46 | 4.03 | 3.43 |
| CDK2 + E1 | 3 | 11.54 | 7.99 | 2.87 |
| CDK20 + H | 3 | 6.96 | 4.02 | 1.79 |
| CDK3 + E1 | 3 | 4.80 | 8.39 | 1.68 |
| CDK4 + D1 | 2 | 4.25 | 1.40 | 1.62 |
| CDK4 + D3 | 3 | 5.27 | 1.60 | 1.73 |
| CDK5 + CDK5R1 | 2 | 10.53 | 5.37 | N/A |
| CDK5 + CDK5R2 | 2 | 10.27 | 5.12 | N/A |
| CDK6 + D1 | 1 | 2.04 | 1.33 | 1.28 |
| CDK7 + H | 1 | 2.40 | 1.17 | 1.36 |
| CDK9 + K | 3 | 3.60 | 4.26 | 1.42 |
| CDK9 + T1 | 2 | 2.65 | 2.39 | 1.10 |
| CDKL1 | 2 | 3.50 | 2.78 | 1.18 |
| CDKL2 | 3 | 8.85 | 2.82 | 1.70 |
| CDKL3 | 2 | 2.55 | 1.42 | 1.24 |
| CDKL5 | 3 | 5.95 | 3.64 | 1.98 |
| CERK | 1 | 1.19 | 1.78 | 1.05 |
| CHEK1 | 2 | 1.60 | 2.58 | 1.07 |
| CHEK2 | 2 | 1.78 | 2.08 | 1.22 |
| CHUK | 1 | 1.09 | 1.67 | 1.07 |

FIG. 1D

| Total Kinase Entities | Tracer | 1804 | 1817 | 1294 |
|---|---|---|---|---|
| 595 | | | | |
| | Linker | O4 | O4 | O4 |
| Kinase Entities Hit > 1.4-fold | [Tracer], uM | 0.5 | 0.5 | 1 |
| 286 | Mode | Live | Live | Live |
| | Hit Count > 1.3999 | 7600 Fold Change | 7520 Fold Change | K5 Fold Change |
| CLK1 | 3 | 7.10 | 4.52 | 5.17 |
| CLK2 | 2 | 3.71 | 5.02 | PCTK-EXP |
| CLK4 | 3 | 3.20 | 4.58 | 3.20 |
| COQ8A | 2 | 1.61 | 1.65 | 1.19 |
| COQ8B | 2 | 2.18 | 1.99 | 1.14 |
| CSF1R | 1 | 1.31 | 1.70 | 1.20 |
| CSK | 1 | 1.25 | 1.45 | 1.05 |
| CSNK1A1 | 1 | 1.42 | 1.40 | 1.06 |
| CSNK1A1L | 2 | 3.05 | 1.82 | 1.18 |
| CSNK1D | 2 | 3.07 | 3.26 | 1.27 |
| CSNK1E | 2 | 1.47 | 1.63 | 1.06 |
| CSNK1G2 | 2 | 2.94 | 1.71 | 1.34 |
| CSNK1G3 | 2 | 1.69 | 1.61 | 1.14 |
| CSNK2A1 | 2 | 2.70 | 1.95 | 1.14 |
| CSNK2A2 | 3 | 10.19 | 5.62 | 2.49 |
| DAPK1 | 1 | 1.50 | 1.33 | 1.02 |
| DAPK2 | 2 | 2.42 | 1.43 | 1.15 |
| DAPK3 | 1 | 1.93 | 1.31 | 0.98 |
| DCLK3 | 1 | 2.23 | 1.32 | 1.14 |

FIG. 1D (cont.)

| | | | | |
|---|---|---|---|---|
| DDR1 | 2 | 1.41 | 1.91 | POOR FIT |
| DDR2 | 3 | 3.66 | 6.77 | 2.69 |
| DMPK | 2 | 2.06 | 2.19 | 1.11 |
| DYRK1A | 2 | 2.37 | 2.13 | POOR FIT |
| DYRK1B | 2 | 2.72 | 2.74 | 1.38 |
| DYRK2 | 3 | 2.00 | 1.67 | 1.51 |
| DYRK3 | 3 | 1.84 | 1.62 | 1.53 |
| EGFR(E746-A750del) | 3 | 1.67 | 1.42 | 1.55 |
| EGFR(G719C) | 1 | 1.63 | 1.37 | 1.06 |
| EGFR(L747-E749del, A750P) | 2 | 1.57 | 1.40 | 1.31 |
| EGFR(L858R) | 2 | 1.52 | 1.43 | 1.20 |
| EGFR(L858R,T790M) | 3 | 1.60 | 1.50 | 1.42 |
| EIF2AK4k2 | 2 | 4.68 | 2.85 | 1.29 |
| EPHA1 | 3 | 2.83 | 4.11 | 2.26 |
| EPHA2 | 3 | 2.00 | 2.38 | 1.42 |
| EPHA3 | 2 | 1.42 | 1.77 | 1.11 |
| EPHA4 | 3 | 2.59 | 2.98 | 1.55 |
| EPHA5 | 3 | 2.47 | 2.60 | 1.62 |
| EPHA6 | 3 | 4.59 | 5.89 | 3.40 |
| EPHA7 | 3 | 5.38 | 5.73 | 2.94 |
| EPHA8 | 3 | 2.98 | 2.82 | 2.04 |
| EPHB1 | 3 | 3.05 | 4.26 | 1.78 |
| EPHB2 | 2 | 1.89 | 2.35 | 1.37 |
| EPHB4 | 3 | 2.87 | 4.19 | 1.81 |

FIG. 1D (cont.)

| | | | | |
|---|---|---|---|---|
| ERN1 | 3 | 2.69 | 1.76 | 1.57 |
| ERN2 | 3 | 5.63 | 3.41 | 2.15 |
| FER | 3 | 2.47 | 2.33 | 1.70 |
| FES | 2 | 2.42 | 3.35 | 1.24 |
| FGFR1 | 3 | 5.25 | 5.14 | 3.69 |
| FGFR2 | 3 | 4.23 | 5.39 | 2.40 |
| FGFR3 | 3 | 3.60 | 4.30 | 2.47 |
| FGFR3(G697C) | 3 | 2.86 | 3.55 | 2.26 |
| FGFR4 | 3 | 2.94 | 2.50 | 2.20 |
| FLT1 | 3 | 2.18 | 3.10 | 1.61 |
| FLT3 | 2 | 3.72 | 4.03 | POOR FIT |
| FLT3(D835H) | 3 | 4.81 | 5.44 | 3.83 |
| FLT3(D835V) | 3 | 4.49 | 5.32 | 3.33 |
| FLT3(D835Y) | 3 | 4.60 | 5.33 | 3.66 |
| FLT3(K663Q) | 3 | 3.73 | 4.81 | 3.54 |
| FLT3(N841I) | 3 | 4.37 | 5.20 | 3.09 |
| FLT3(R834Q) | 3 | 3.64 | 4.45 | 3.26 |
| FRK | 2 | 1.59 | 1.44 | 1.34 |
| FYN | 3 | 3.19 | 2.88 | 2.90 |
| GAK | 3 | 23.49 | 12.89 | 17.88 |
| GK2 | 2 | 1.53 | 2.08 | 1.01 |
| GRK5 | 1 | 1.28 | 1.44 | 1.08 |
| GRK6 | 1 | 1.24 | 1.47 | 1.07 |
| GRK7 | 2 | 1.73 | 1.65 | 1.11 |
| GSK3A | 2 | 1.55 | 2.47 | 1.06 |
| GSK3B | 2 | 1.89 | 2.94 | 1.02 |

FIG. 1D (cont.)

| | | | | |
|---|---|---|---|---|
| GUCY2D | 1 | 1.27 | 1.80 | 1.08 |
| HIPK1 | 1 | 1.77 | 1.39 | 1.13 |
| HIPK2 | 1 | 2.03 | 1.31 | 1.16 |
| HIPK3 | 2 | 2.36 | 1.43 | 1.26 |
| HIPK4 | 3 | 18.93 | 6.62 | 5.58 |

FIG. 1E

| Total Kinase Entities | Tracer | 1804 | 1817 | 1294 |
|---|---|---|---|---|
| 595 | Chemotype | NHCTxpip | mCTxpip | CTx-0294885 |
| | Linker | O4 | O4 | O4 |
| Kinase Entities Hit > 1.4-fold | [Tracer], uM | 0.5 | 0.5 | 1 |
| 206 | Mode | Live | Live | Live |
| | Hit Count > 1.3999 | 7600 Fold Change | 7520 Fold Change | K5 Fold Change |
| IRAK3 | 3 | 4.01 | 5.84 | 4.11 |
| IRAK4 | 3 | 9.87 | 26.54 | 6.90 |
| ITK | 3 | 3.50 | 5.95 | 2.10 |
| JAK2 | 2 | 2.20 | 1.97 | |
| JAK2 (V617F) | 3 | 5.42 | 6.86 | 5.64 |
| JAK2JH1 | 2 | 3.52 | 3.62 | |
| JAK3 | 2 | 3.42 | 1.73 | |
| JNK3 | 3 | 2.15 | 1.78 | 1.74 |
| KDR | 2 | 1.48 | 1.50 | |
| Kit | 2 | 1.51 | 2.16 | 1.14 |
| KIT(A829P) | 3 | 2.46 | 3.17 | 1.73 |
| KIT(D816H) | 3 | 2.77 | 3.41 | 1.93 |
| KIT(D816V) | 3 | 3.80 | 4.83 | 2.53 |
| KIT(L576P) | 2 | 1.78 | 2.86 | 1.29 |
| KIT(V559D) | 3 | 2.58 | 4.07 | 1.94 |
| KIT(V559D,T670I) | 3 | 2.16 | 3.27 | 1.50 |
| KIT(V559D,V654A) | 2 | 1.40 | 2.11 | 1.06 |
| LATS1 | 3 | 7.67 | 4.70 | 3.24 |
| LATS2 | 3 | 6.65 | 6.89 | 3.96 |
| LCK | 3 | 2.81 | 2.92 | 1.56 |
| LIMK1 | 2 | 4.77 | 3.76 | 1.32 |

FIG. 1E (cont.)

| | | | | |
|---|---|---|---|---|
| LIMK2 | 2 | 5.55 | 4.61 | 1.38 |
| LMTK2 | 1 | 1.18 | 1.51 | |
| LMTK3 | 1 | 1.32 | 1.83 | 1.27 |
| LRRK2 | 2 | 3.08 | 5.14 | |
| LRRK2(G2019S) | 2 | 2.42 | 4.03 | |
| LYN | 2 | 2.01 | 2.02 | 1.25 |
| MAP2K4 | 1 | 1.05 | 1.41 | 0.99 |
| MAP2K5 | 2 | 1.97 | 1.63 | 1.03 |
| MAP3K10 | 3 | 4.52 | 4.67 | 1.87 |
| MAP3K11 | 3 | 4.80 | 5.23 | 2.43 |
| MAP3K12 | 3 | 3.48 | 4.34 | 1.86 |
| MAP3K13 | 3 | 1.93 | 2.47 | 1.49 |
| MAP3K14 | 2 | 1.58 | 1.75 | 0.97 |
| MAP3K19 | 3 | 2.67 | 2.63 | 1.40 |
| MAP3K2 | 2 | 2.71 | 2.61 | |
| MAP3K21 | 2 | 2.61 | 2.22 | 1.25 |
| MAP3K3 | 2 | 2.85 | 4.08 | 1.29 |
| MAP3K4 | 3 | 3.66 | 6.98 | 2.17 |
| MAP3K5 | 1 | 1.28 | 1.57 | 1.04 |
| MAP3K6 | 1 | 1.26 | 1.43 | 0.97 |
| MAP3K9 | 3 | 2.82 | 2.57 | 2.22 |
| MAP4K1 | 3 | 3.94 | 2.07 | 2.58 |
| MAP4K2 | 3 | 7.03 | 10.89 | 1.97 |
| MAP4K3 | 3 | 6.84 | 3.45 | 1.58 |
| MAP4K5 | 2 | 2.82 | 1.74 | 1.18 |
| MAPK1 | 2 | 1.81 | 1.70 | 1.40 |
| MAPK11 | 3 | 5.04 | 1.57 | 2.94 |

FIG. 1E (cont.)

| | | | | |
|---|---|---|---|---|
| MAPK13 | 2 | 1.67 | 1.76 | 1.06 |
| MAPK14 | 3 | 3.69 | 1.58 | 1.86 |
| MAPK3 | 1 | 1.30 | 1.52 | 1.23 |
| MAPK4 | 3 | 49.60 | 42.86 | 4.04 |
| MAPK6 | 3 | 26.79 | 18.83 | 12.79 |
| MAPK8 | 3 | 5.75 | 4.67 | 3.45 |
| MAPK9 | 3 | 10.57 | 7.60 | 5.75 |
| MARK2 | 3 | 2.99 | 4.46 | 1.75 |
| MARK3 | 1 | POOR EXP | 2.44 | 1.20 |
| MARK4 | 3 | 6.18 | 6.77 | 2.44 |
| MAST3 | 3 | 2.04 | 1.41 | 1.60 |
| MAST4 | 2 | 2.13 | 1.33 | 1.79 |
| MELK | 3 | 3.54 | 4.75 | 2.20 |
| MERTK | 3 | 2.23 | 3.06 | 2.02 |
| MET | 3 | 5.77 | 4.36 | 5.52 |
| MET(M1250T) | 3 | 6.71 | 4.94 | 5.91 |
| MET(Y1235D) | 3 | 4.05 | 3.29 | 2.72 |
| MKNK2 | 2 | 2.57 | 2.49 | 1.12 |
| MLTK | 2 | 4.13 | 2.40 | 1.06 |
| MOK | 2 | 4.06 | 9.07 | 1.16 |
| MUSK | 2 | 7.61 | 9.11 | POOR EXP |
| MYLK2 | 3 | 20.12 | 14.97 | 7.44 |
| MYLK3 | 3 | 13.45 | 8.05 | 2.49 |
| MYLK4 | 3 | 11.49 | 6.37 | 12.48 |
| NEK1 | 3 | 4.43 | 7.94 | 1.48 |
| NEK11 | 3 | 3.86 | 4.17 | 1.66 |

FIG. 1F

| Total Kinase Entities | Tracer | 1804 | 1817 | 1294 |
|---|---|---|---|---|
| 595 | | | | |
| | Linker | O4 | O4 | O4 |
| Kinase Entities Hit > 1.4-fold | [Tracer], uM | 0.5 | 0.5 | 1 |
| 126 | Mode | Live | Live | Live |
| | Hit Count > 1.3999 | 7600 Fold Change | 7520 Fold Change | K5 Fold Change |
| NIM1K | 2 | 6.08 | 10.25 | 1.14 |
| NLK | 2 | 2.80 | 1.74 | 1.21 |
| NPR1 | 2 | 1.67 | 2.39 | 1.22 |
| NPR2 | 1 | 1.23 | 1.68 | 1.13 |
| NRK | 2 | 1.51 | 2.85 | 1.09 |
| NTRK1v1 | 3 | 7.07 | 7.00 | 5.34 |
| NTRK1v2 | 3 | 6.94 | 6.62 | 5.10 |
| NTRK2 | 3 | 8.82 | 7.71 | 8.36 |
| NTRK3 | 1 | 1.25 | 1.46 | 1.11 |
| NUAK1 | 3 | 3.75 | 4.22 | 3.65 |
| NUAK2 | 2 | 2.43 | 2.15 | 1.34 |
| PAK4 | 3 | 10.78 | 12.96 | 1.58 |
| PAK6 | 2 | 2.64 | 2.37 | 1.03 |
| PDPK1 | 2 | 1.69 | 1.91 | 1.19 |
| PHKG1 | 3 | 8.04 | 3.70 | 4.38 |
| PHKG2 | 3 | 2.08 | 1.54 | 1.56 |
| PI4K2A | 2 | 1.40 | 2.02 | 1.10 |
| PIK3C3 | 1 | 1.39 | 2.99 | 1.18 |
| PIKFYVE | 1 | 1.35 | 1.40 | |
| PIM1 | 2 | 1.51 | 1.36 | 1.56 |
| PIM3 | 3 | 2.04 | 1.54 | 1.65 |

FIG. 1F (cont.)

| | | | | |
|---|---|---|---|---|
| PINK1 | 2 | 1.57 | 2.61 | 1.16 |
| PIP4K2C | 2 | 1.59 | 2.86 | 1.12 |
| PIP5K1B | 1 | 1.20 | 1.60 | 1.08 |
| PKDCC | 1 | 1.14 | 1.59 | 1.02 |
| PKMYT1 | 3 | 2.38 | 2.18 | 1.68 |
| PKN1 | 1 | 1.28 | 1.81 | 1.15 |
| PKN2 | 1 | 1.17 | 1.41 | 1.09 |
| PKN3 | 2 | 2.03 | 1.85 | 1.30 |
| PLK2 | 3 | 2.72 | 5.02 | 1.76 |
| PLK3 | 2 | 3.26 | 6.95 | 1.33 |
| PLK4 | 3 | 7.57 | 7.49 | 5.41 |
| PNCK | 2 | 1.94 | 1.78 | 1.23 |
| POMK | 2 | 1.86 | 2.77 | 1.26 |
| PRKA + B1 and G1 | 3 | 25.21 | 18.05 | 17.06 |
| PRKAA2 | 3 | 14.14 | 14.70 | 7.25 |
| PRKACA | 3 | 6.39 | 5.37 | 3.75 |
| PRKACB | 3 | 4.65 | 4.30 | 2.63 |
| PRKCB | 1 | 1.20 | 1.47 | 1.05 |
| PRKCE | 2 | 2.62 | 1.65 | 1.20 |
| PRKCH | 1 | 1.30 | 1.46 | 1.06 |
| PRKCQ | 2 | 1.46 | 1.52 | 1.38 |
| PRKD3 | 1 | 1.41 | 1.23 | 1.06 |
| PRKG1 | 1 | 1.21 | 1.46 | 1.12 |
| PRKG2 | 2 | 1.92 | 2.79 | 1.26 |
| PRKX | 3 | 7.64 | 9.31 | 2.61 |
| PTK2 | 3 | 4.06 | 4.01 | 3.47 |
| PTK2B | 3 | 2.73 | 2.99 | 1.71 |

FIG. 1F (cont.)

| | | | | |
|---|---|---|---|---|
| PTK6 | 3 | 3.75 | 5.54 | 2.13 |
| RET | 3 | 9.66 | 10.31 | 5.06 |
| RET(M918T) | 3 | 8.38 | 6.94 | 4.41 |
| RET(V804L) | 3 | 9.53 | 10.33 | 5.44 |
| RET(V804M) | 3 | 10.38 | 10.87 | 5.76 |
| RIOK2 | 3 | 7.50 | 4.11 | 4.30 |
| RIPK1 | 3 | 2.64 | 4.44 | 1.75 |
| RIPK2 | 3 | 7.23 | 5.74 | 1.94 |
| ROCK1 | 1 | 1.24 | 1.85 | 1.20 |
| ROCK2 | 2 | 1.40 | 1.80 | 1.04 |
| RON | 3 | 3.47 | 6.34 | 1.72 |
| ROR1 | 1 | 1.24 | 1.44 | 1.18 |
| RPS6KA1 | 3 | 9.56 | 7.34 | 6.74 |
| RPS6KA2 | 3 | 5.66 | 4.74 | 5.36 |
| RPS6KA3 | 3 | 6.79 | 4.83 | 6.13 |
| RPS6KA4 | 3 | 7.42 | 8.81 | 5.36 |
| RPS6KA6 | 3 | 5.11 | 3.79 | 4.65 |
| RPS6KB1 | 1 | 1.61 | 1.32 | 1.21 |
| RYK | 2 | 1.46 | 2.13 | 1.24 |
| SBK1 | 1 | 1.35 | 1.55 | 1.22 |
| SBK3 | 3 | 5.90 | 9.03 | 5.67 |
| SGK1 | 3 | 3.15 | 3.32 | 1.98 |
| SGK2 | 3 | 1.89 | 2.04 | 1.52 |
| SGK3 | 2 | 1.47 | 1.51 | 1.10 |
| SIK1 | 3 | 13.17 | 9.55 | 9.68 |
| SIK3 | 3 | 11.62 | 7.39 | 2.39 |

CC-1861

CTx-0294885

- 200 Kinases Evaluated
  - 300 nM Compound
- Compounds ranked according to CC-1861 fractional occupancy
- 71 Kinases prefer CC-1861 over CTx
- 4 Kinases prefer CTx over CC-1861

| Target | CC-1861 Potency (nM) | CTx-0294885 Potency (nM) |
|---|---|---|
| SBK3 | 26 | 12 |
| NIM1K | 31 | 2100 |
| TYK2JH2 | 55 | 2000 |
| HIPK2 | 66 | 240 |
| JAK2JH1 | 82 | 150 |
| CSNK2A1 | 120 | 3500 |
| TYK2 | 150 | 1400 |
| SGK1 | 150 | 620 |
| HIPK3 | 230 | 3000 |
| MAST3 | 290 | 270 |
| NEK11 | 320 | 1100 |
| NEK1 | 330 | 2300 |
| CSNK1G2 | 330 | 1400 |
| FGFR4 | 340 | 690 |
| MAST4 | 410 | 460 |
| MAPK9 | 460 | 700 |
| NEK2 | 520 | 1700 |
| NEK3 | 550 | 5600 |
| TYK2JH1 | 700 | 4200 |
| MAPK11 | 840 | 850 |
| NEK4 | 840 | 4700 |
| MAP3K21 | 940 | 3600 |
| DSTYK | 1300 | >20000 |
| MAP3K19 | 2100 | 3700 |
| CSNK1A1L | 3400 | 4500* |
| STK38L | 3500 | >10000 |

BROAD SPECTRUM KINASE BINDING AGENTS

CROSS-REFERENCE TO RELATED APPLICATIONS

The present application is a continuation of U.S. Ser. No. 16/426,982, filed May 30, 2019, which claims the priority benefit Provisional Patent Application No. 62/677,956, filed May 30, 2018, each of which is incorporated in its entirety.

SEQUENCE LISTING

The text of the computer readable sequence listing filed herewith, titled "36452-303 SEQUENCE LISTING", created Jan. 24, 2023, having a file size of 6,204 bytes, is hereby incorporated by reference in its entirety.

FIELD

Provided herein are compounds that are broad-spectrum protein kinase binding agents, detectable tracers comprising such compounds, and method of use thereof for the detection of protein kinases.

BACKGROUND

The human genome contains about 560 protein kinase genes, and they constitute about 2% of all human genes (Manning et al. (2002) *Science* 298 (5600): 1912-1934; herein incorporated by reference in its entirety). Up to 30% of all human proteins may be modified by kinase activity, and kinases are known to regulate the majority of cellular pathways, especially those involved in signal transduction. The chemical activity of a kinase involves transferring a phosphate group from a nucleoside triphosphate (usually ATP) and covalently attaching it to specific amino acids with a free hydroxyl group. Most kinases act on both serine and threonine (serine/threonine kinases), others act on tyrosine (tyrosine kinases), and a number act on all three (dual-specificity kinases) (Dhanasekaran & Premkumar (September 1998). Oncogene. 17 (11 Reviews): 1447-55.; herein incorporated by reference in its entirety). Aberrant kinase signaling is associated with many diseases and conditions.

U.S. Pat. Pub No. 2014/0323346 and Zhang et al. (*J. Proteome Res.* 2013, 12, 3104-3116), both of which are herein incorporated by reference in their entireties, describe protein kinase binding agents. Improved kinase ligands with broad specificity are needed to allow cellular kinase profiling, kinase purification, etc.

SUMMARY

Provided herein are compounds that are broad-spectrum protein kinase binding agents, detectable tracers comprising such compounds, and method of use thereof for the detection of protein kinases.

In some embodiments, provided herein are broad-spectrum kinase binding agents of formula:

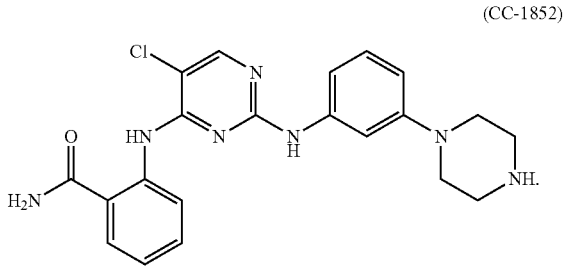 [SMILES: NC(=O)c1ccccc1Nc1nc(Nc2cccc(N3CCNCC3)c2)ncc1Cl]

(CC-1852)

In some embodiments, provided herein are broad-spectrum kinase binding agents of formula:

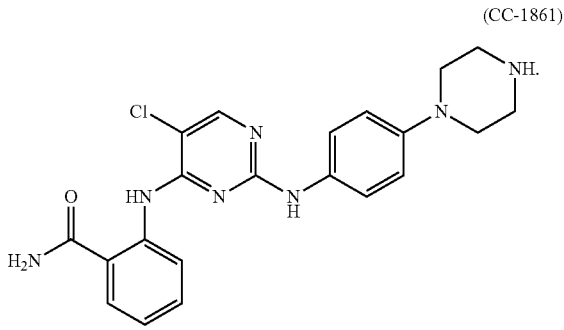 [SMILES: NC(=O)c1ccccc1Nc1nc(Nc2ccc(N3CCNCC3)cc2)ncc1Cl]

(CC-1861)

In some embodiments, provided herein are broad-spectrum kinase binding agents of formula:

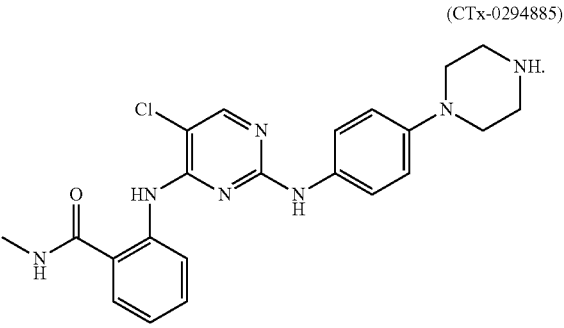 [SMILES: CNC(=O)c1ccccc1Nc1nc(Nc2ccc(N3CCNCC3)cc2)ncc1Cl]

(CTx-0294885)

In some embodiments, provided herein are broad-spectrum kinase binding agents (e.g., CC-1852) attached to a functional element or solid surface, comprising a moiety of formula:

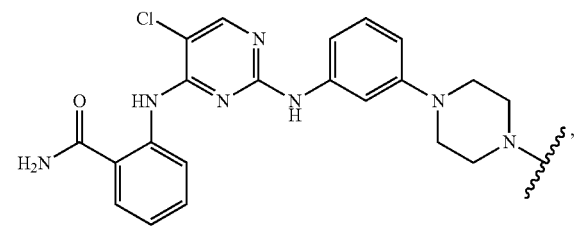 [SMILES: *N1CCN(c2cccc(Nc3ncc(Cl)c(Nc4ccccc4C(N)=O)n3)c2)CC1]

attached to the functional element or solid surface (e.g., CC-1816, CC-1817, etc.).

In some embodiments, provided herein are broad-spectrum kinase binding agents (e.g., CC-1861) attached to a functional element or solid surface, comprising a moiety of formula:

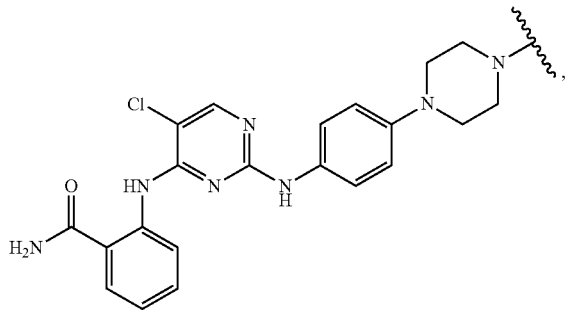 [SMILES: *N1CCN(c2ccc(Nc3ncc(Cl)c(Nc4ccccc4C(N)=O)n3)cc2)CC1]

attached to the functional element or solid surface (e.g., CC-1803, CC-1804, etc.).

In some embodiments, provided herein are broad-spectrum kinase binding agents (e.g., CTx-0294885) attached to a functional element or solid surface, comprising a moiety of formula:

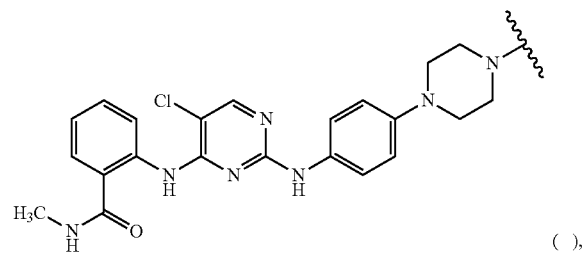

attached to the functional element or solid surface (e.g., CC-1290, CC-1294, etc.).

In some embodiments, provided herein are the broad-spectrum kinase binding agents herein linked to a solid surface, wherein the solid surface is selected from a sedimental particle, a membrane, glass, a tube, a well, a self-assembled monolayer, a surface plasmon resonance chip, or a solid support with an electron conducting surface. In some embodiments, the sedimental particle is a magnetic particle.

In some embodiments, provided herein are the broad-spectrum kinase binding agents herein linked to a functional element, wherein the functional element is selected from a detectable element, an affinity element, and a capture element. In some embodiments, the detectable element comprises a fluorophore, chromophore, radionuclide, electron opaque molecule, a MRI contrast agent, SPECT contrast agent, or mass tag. In some embodiments, a broad-spectrum kinase binding agent described herein (e.g., CC-1852, CC-1861, or CTx-0294885) is attached to the functional element directly. In some embodiments, a broad-spectrum kinase binding agent described herein (e.g., CC-1852, CC-1861, or CTx-0294885) is attached to the functional element via a linker. In some embodiments, the linker comprises —[(CH$_2$)$_2$O]$_n$—, wherein n is 1-20 (e.g., 1, 2, 3, 4, 5, 6, 7, 8, 9 10, 11, 12, 13, 14, 15, 16, 17, 18, 19 20, or ranges therebetween). In some embodiments, the linker is attached to the broad-spectrum kinase binding agent described herein (e.g., CC-1852, CC-1861, or CTx-0294885), and/or the functional element, by an amide bond.

In some embodiments, provided herein is a broad-spectrum kinase binding agent comprising a structure of:

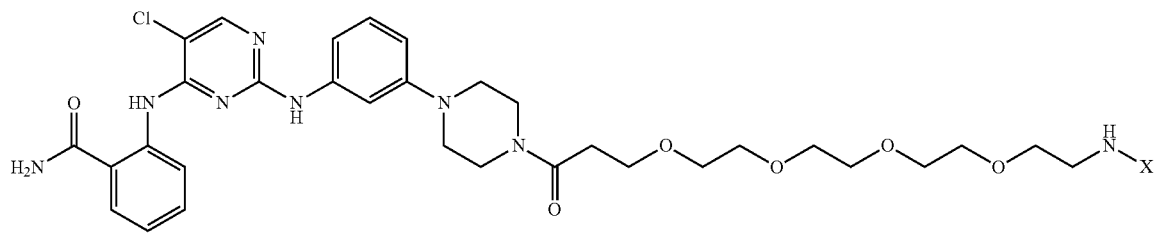

wherein X is a functional element or solid surface. In some embodiments, X is a fluorophore. In some embodiments, provided herein is a broad-spectrum kinase binding agent comprising a structure of:

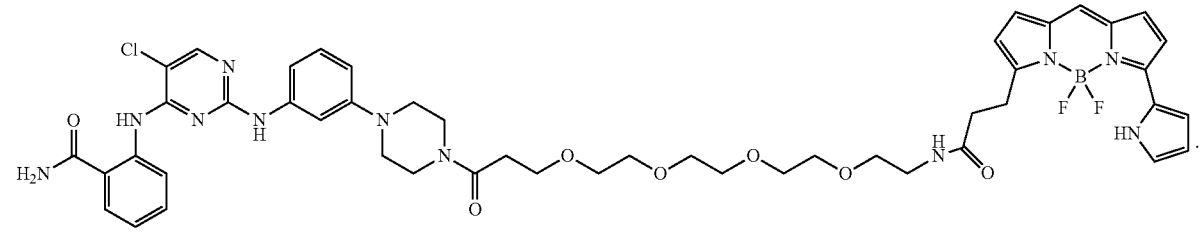

In some embodiments, provided herein is a broad-spectrum kinase binding agent comprising a structure of:

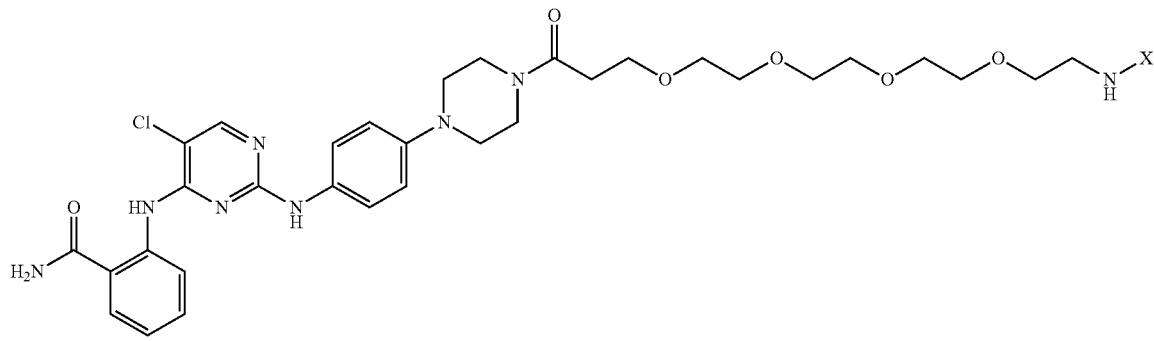

wherein X is a functional element or solid surface. In some embodiments, X is a fluorophore. In some embodiments, provided herein is a broad-spectrum kinase binding agent comprising a structure of:

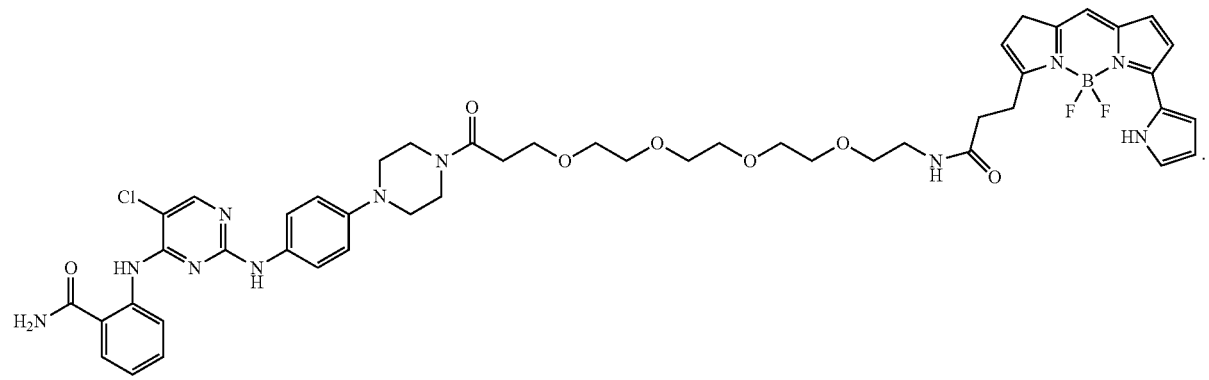

In some embodiments, provided herein is a broad-spectrum kinase binding agent comprising a structure of:

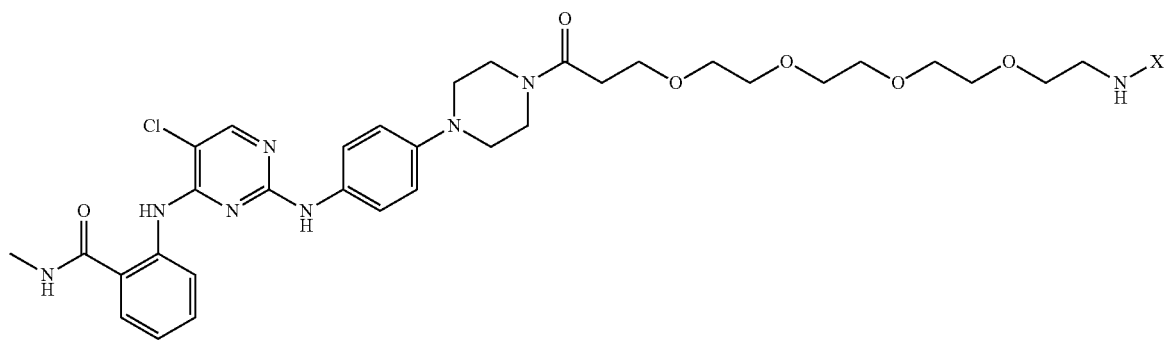

wherein X is a functional element or solid surface. In some embodiments, X is a fluorophore. In some embodiments, provided herein is a broad-spectrum kinase binding agent comprising a structure of:

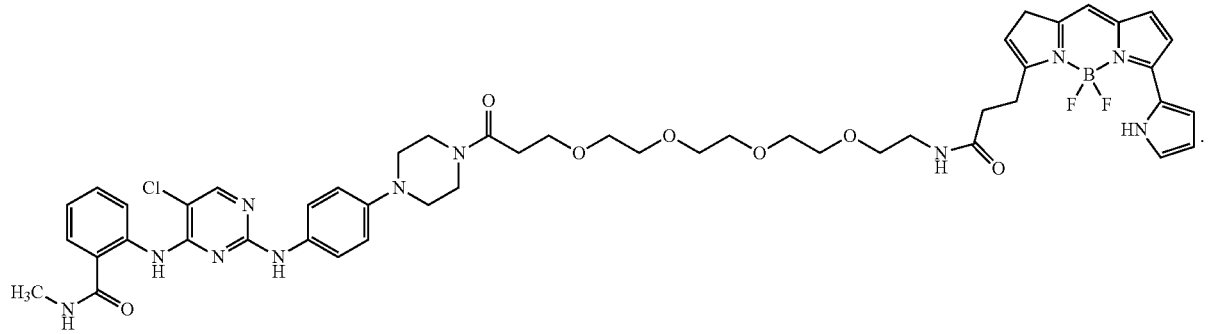

In some embodiments, a broad-spectrum kinase binding agent herein comprises a non-natural abundance of one or more stable heavy isotopes.

In some embodiments, provided herein are methods of detecting or quantifying kinases in a sample, comprising contacting the sample with a broad-spectrum kinase binding agent herein and detecting or quantifying the functional element of a signal produced thereby. In some embodiments, the functional element of a signal produced thereby is detected or quantified by fluorescence, mass spectrometry, optical imaging, magnetic resonance imaging (MRI), and energy transfer (e.g., FRET, BRET, ALPHA).

In some embodiments, provided herein are methods of isolating kinases from a sample, comprising contacting the sample with a broad-spectrum kinase binding agent herein, and separating the functional element of the solid surface, as well as the bound kinases, from the unbound portion of the sample. In some embodiments, methods comprise isolating the kinases from a sample by a method described herein, and analyzing the isolated kinases by mass spectrometry.

In some embodiments, provided herein are methods of monitoring interactions between kinases and unmodified biomolecules comprising contacting the sample with a broad-spectrum kinase binding agent herein.

In some embodiments, methods herein are performed using a sample selected from a cell, cell lysate, body fluid, tissue, biological sample, in vitro sample, and environmental sample.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A-B. Summary of the BRET results generated with kinase tracers against a large panel of kinase/NanoLuc® fusions expressed in live cells. Assay signals were assessed by taking the ratio of BRET in the presence of tracer/no tracer control. Assays are categorized as follows: >3-fold signal (green cells), 2-3 fold signal (yellow cells), and 1.5-2 fold signal (red cells).

FIG. 1C-F. Individual BRET signals observed between the broad-spectrum kinase tracers and individual kinase/NanoLuc® fusions expressed in live cells. Assay signals were assessed by taking the ratio of BRET in the presence of tracer/no tracer control. Assays are categorized as follows: >3-fold signal (green cells), 2-3 fold signal (yellow cells), and 1.5-2 fold signal (red cells).

Figure 6:
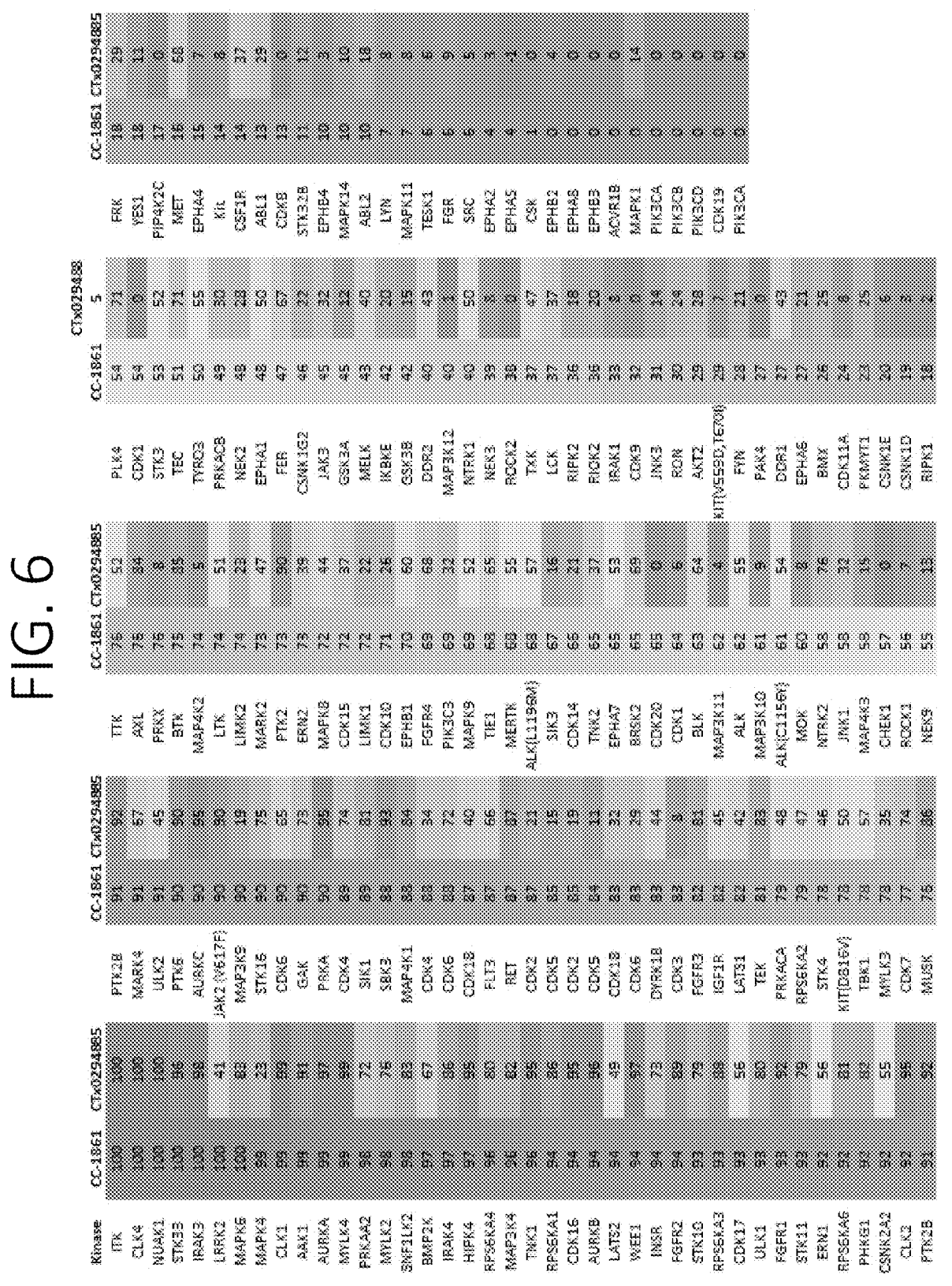

FIG. 6A detailed heat map of target engagement potency in live cells for 300 nM CC-1861 vs CTx-0294885. Target engagement was measured by competitive displacement against NanoBRET™ tracers in living HEK293 cells. Red indicates higher occupancy, and green indicates lower occupancy.

FIG. 8. Detailed comparisons of intracellular affinity values for CC-1861 vs CTx-0294885 for various kinases in living cells. Values were measured by competitive displacement of NanoBRET™ tracers in living cells.

DEFINITIONS

Figure 2A:
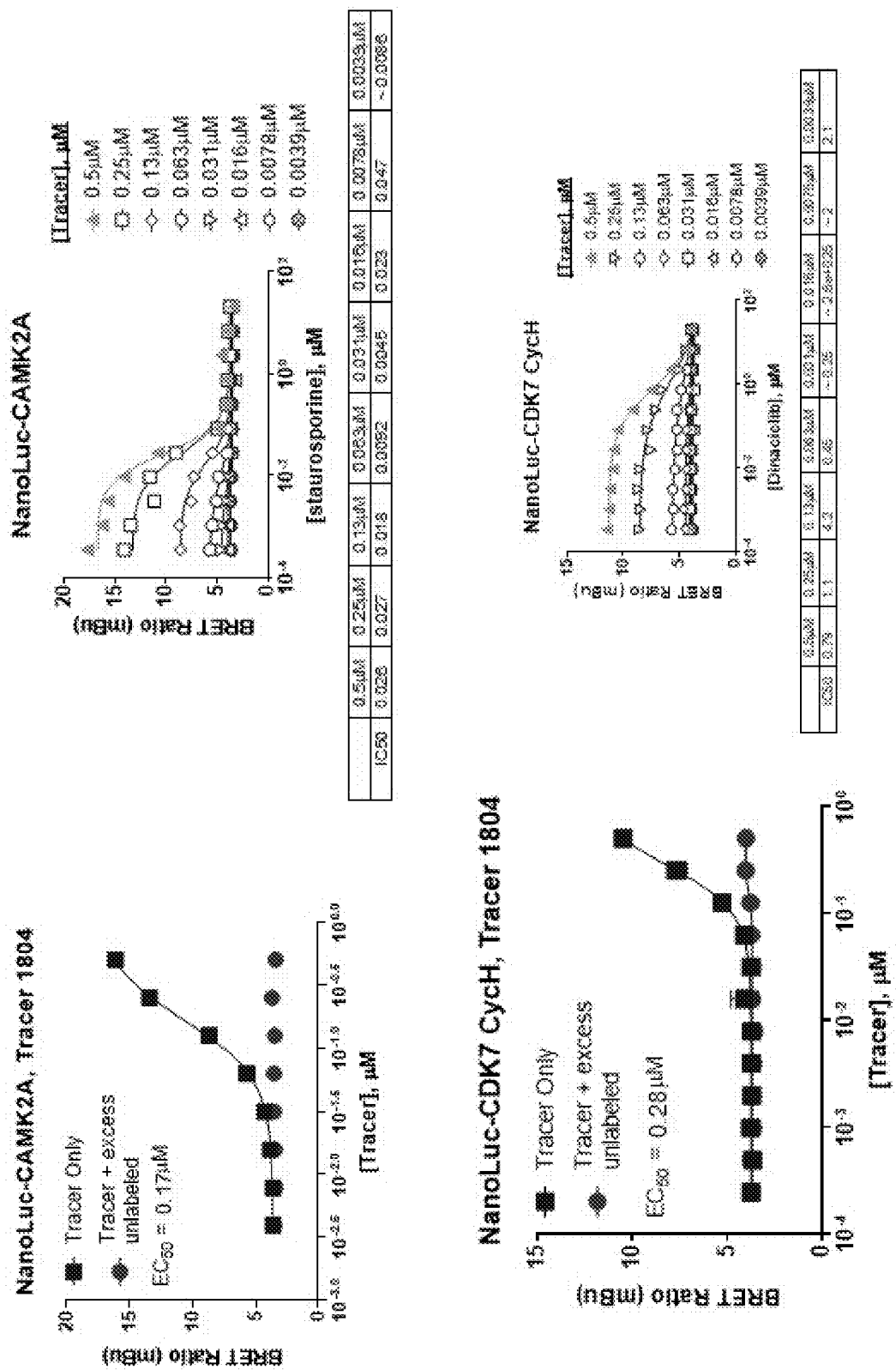
FIG. 2A-C. BRET Target Engagement results in live cells with representative Kinase/NanoLuc® fusions. Cells transfected with plasmid DNA encoding each kinase/Nluc fusion was treated with serially diluted tracer 1804 (left panels), resulting in a dose-dependent increase of specific BRET. Target engagement can be observed for each kinase by titration of unlabeled test compound against a fixed concentration of tracer 1804 (right panels). For each example shown, the BRET signal was superior with tracer 1804 compared to 1294.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide" is a reference to one or more peptides and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "CC-1852" refers to a compound of the structure:

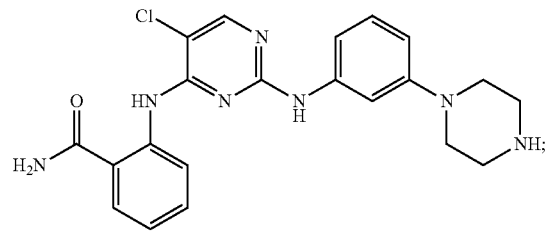

(CC-1852)

or a moiety/substituent of a molecular entity, the moiety/substituent having the structure:

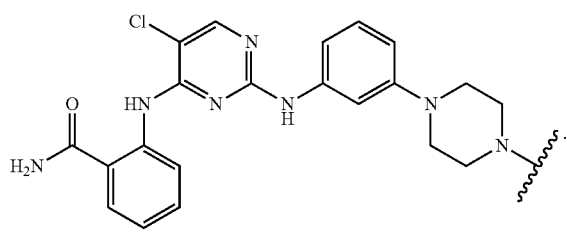

(e.g., CC-1816, CC-1817)

As used herein, the term "CC-1861" refers to a compound of the structure:

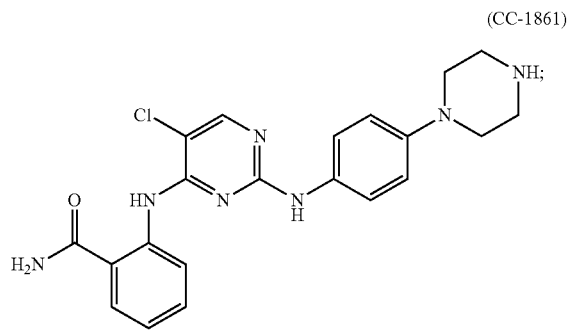 [SMILES: NC(=O)c1ccccc1Nc1nc(Nc2ccc(N3CCNCC3)cc2)ncc1Cl]

(CC-1861)

or a moiety/substituent of a molecular entity, the moiety/substituent having the structure:

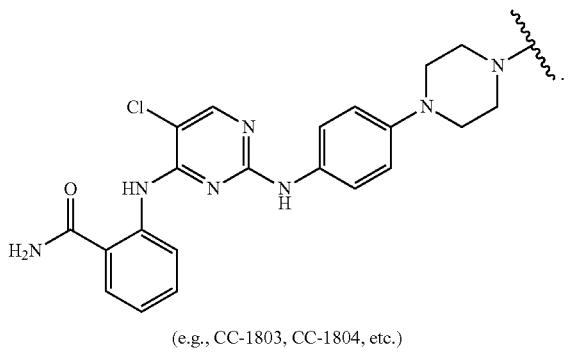 [SMILES: *N1CCN(c2ccc(Nc3ncc(Cl)c(Nc4ccccc4C(N)=O)n3)cc2)CC1]

(e.g., CC-1803, CC-1804, etc.)

As used herein, the term "CTx-0294885" refers to a compound of the structure:

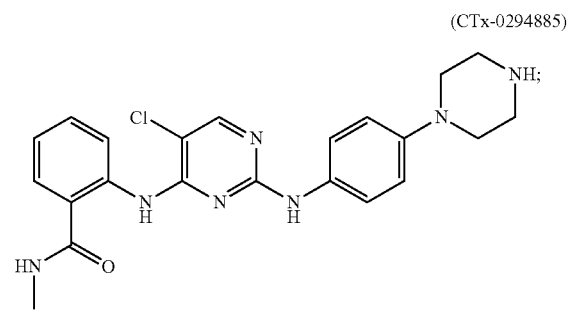 [SMILES: CNC(=O)c1ccccc1Nc1nc(Nc2ccc(N3CCNCC3)cc2)ncc1Cl]

(CTx-0294885)

or a moiety/substituent of a molecular entity, the moiety/substituent having the structure:

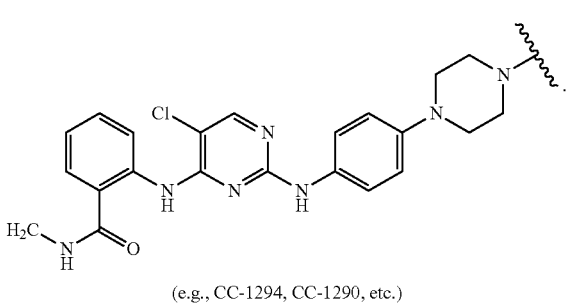 [SMILES: *N1CCN(c2ccc(Nc3ncc(Cl)c(Nc4ccccc4C(=O)NC)n3)cc2)CC1]

(e.g., CC-1294, CC-1290, etc.)

As used herein, the term "tracer" refers to a compound of interest or an agent that binds to an analyte of interest (e.g., protein of interest (e.g., kinase), etc.) and displays a quantifiable or detectable property (e.g., detected or quantified any suitable biochemical or biophysical technique (e.g., optically, magnetically, electrically, by resonance imaging, by mass, by radiation, etc.)). Tracers may comprise a compound of interest or an agent that binds to an analyte of interest linked (e.g., directly or via a suitable linker) to a fluorophore, radionuclide, mass tag, contrast agent for magnetic resonance imaging (MRI), planar scintigraphy (PS), positron emission tomography (PET), single photon emission computed tomography (SPECT), and computed tomography (CT) (e.g., a metal ion chelator with bound metal ion, isotope, or radionuclide), etc.

As used herein, the term "sample" is used in its broadest sense. In one sense, it is meant to include a specimen or culture obtained from any source as well as biological and environmental samples. Biological samples may be obtained from animals (including humans) and encompass fluids, solids, tissues, and gases. Biological samples include blood products such as plasma, serum, and the like. Sample may also refer to cell lysates or purified forms of the enzymes, peptides, and/or polypeptides described herein. Cell lysates may include cells that have been lysed with a lysing agent or lysates such as rabbit reticulocyte or wheat germ lysates. Sample may also include cell-free expression systems. Environmental samples include environmental material such as surface matter, soil, water, crystals, and industrial samples. Such examples are not however to be construed as limiting the sample types applicable to the present invention.

As used herein, the term "linearly connected atoms" refers to the backbone atoms of a chain or polymer, excluding pendant, side chain, or H atoms that do not form the main chain or backbone.

As used herein, the term "functional element" refers to a detectable, reactive, affinity, or otherwise bioactive agent or moiety that is attached (e.g., directly or via a suitable linker) to a compound described herein (e.g., CC-1852, CC-1861, CTx-029485), derivatives or analogs thereof, etc.). Other additional functional elements that may find use in embodiments described herein comprise "localization elements", "detection elements", etc.

As used herein, the term "capture element" refers to a molecular entity that forms a covalent interaction with a corresponding "capture agent."

As used herein, the term "affinity element" refers to a molecular entity that forms a stable noncovalent interaction with a corresponding "affinity agent."

As used herein, the term "solid support" is used in reference to any solid or stationary material to which reagents such as substrates, mutant proteins, drug-like molecules, and other test components are or may be attached. Examples of solid supports include microscope slides, wells of microtiter plates, coverslips, beads, particles, resin, cell culture flasks, as well as many other suitable items. The beads, particles, or resin can be magnetic or paramagnetic.

As used herein, in chemical structures the indication:

represents a point of attachment of one moiety to another moiety.

DETAILED DESCRIPTION

Provided herein are compounds that are broad-spectrum protein kinase binding agents, detectable tracers comprising such compounds, and method of use thereof for the detection of protein kinases.

In some embodiments, provided herein are compounds that bind a broad spectrum of protein kinases (e.g., specific to protein kinases, but not specific among protein kinases). In some embodiments, compounds CC-1852, CC-1861, and/or CTx-0294885:

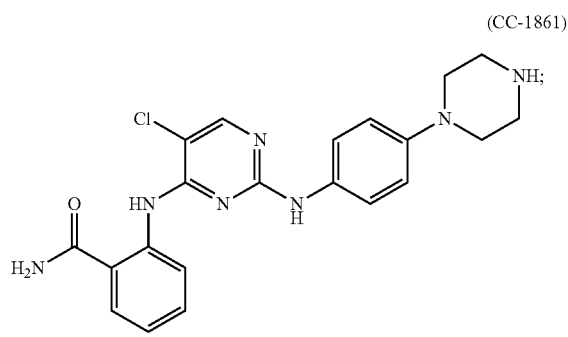

(CC-1861)

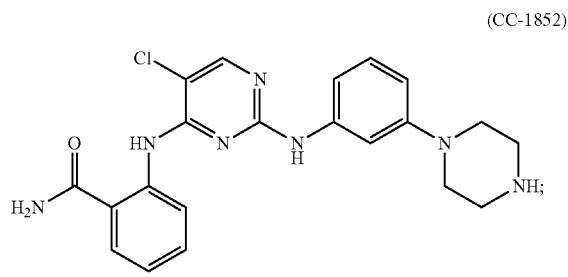

(CC-1852)

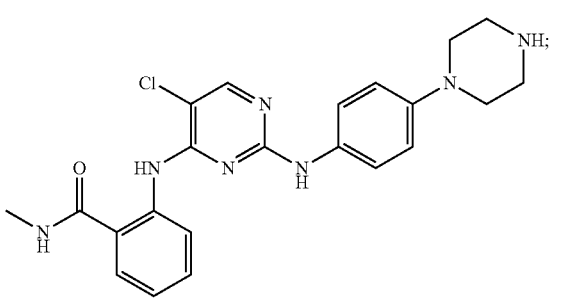

(CTx-0294885)

are provided. In some embodiments, provided herein are compounds or molecular entities comprising a CC-1861, CC-1852, and/or CTx-0294885 moiety:

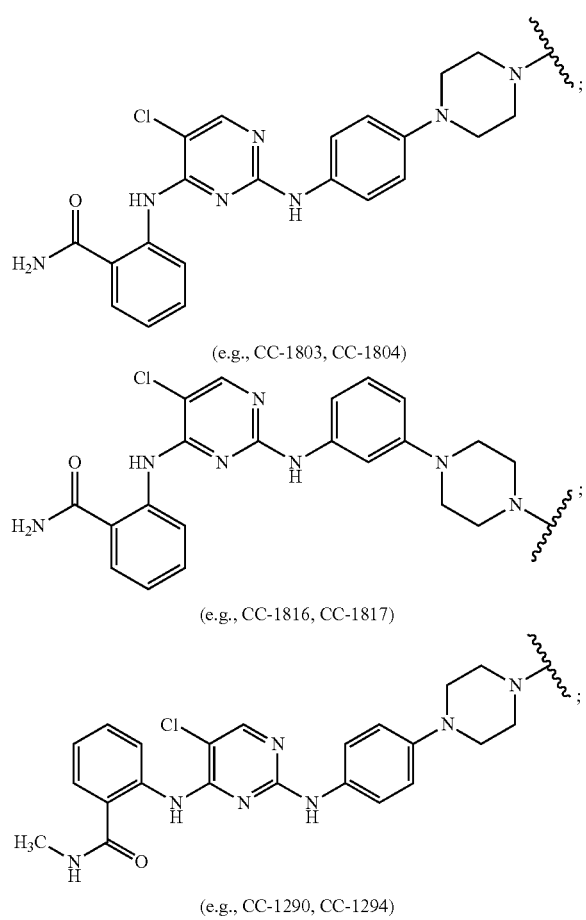

(e.g., CC-1803, CC-1804)

(e.g., CC-1816, CC-1817)

(e.g., CC-1290, CC-1294)

a functional element (e.g., attached to the nitrogen at the 4-position of the piperazine of CC-1861, CC-1852, CTx-0294885). In some embodiments, provided herein are analogs or derivatives of CC-1852, CC-1861, CTx-0294885, and/or compounds or molecular entities comprising analogs or derivatives of CC-1852, CC-1861, CTx-0294885, and a functional element (e.g., analogs or derivatives of CC-1816, CC-1817, CC-1803, CC-1804, CC-1290, CC-1294, etc.). In some embodiments, CC-1852, CC-1861, CTx-0294885, or an analog or derivative thereof is attached directly (via a single covalent bond) to a functional element. In some embodiments, CC-1852, CC-1861, CTx-0294885, or an analog or derivative thereof (e.g., CC-1816, CC-1817, CC-1803, CC-1804, CC-1290, CC1294, etc.) is attached indirectly (via a linker) to a functional element.

In some embodiments, compounds herein (e.g., comprising CC-1852, CC-1861, CTx-0294885, analogs or derivatives thereof, etc.) incorporate reactive groups suitable for chemical conjugation to a functional element (e.g., detectable element, linker, etc.). These reactive groups may be present on the compound (e.g., at the 4-position of the piperazine of CC-1852, CC-1861, CTx-0294885, analogs or derivatives thereof, etc.) or connected by a suitable linker (e.g., connected to the 4-position of the piperazine of CC-1852, CC-1861, CTx-029488, analogs or derivatives thereof (e.g., CC-1816, CC-1817, CC-1803, CC-1804, CC-1290, CC-1294, etc.), etc.). In some embodiments, the reactive group on the compound is configured to react specifically (e.g., via bioorthogonal, or click chemistry) with a reactive partner that is present or has been introduced on the functional element. An exemplary click reaction is copper catalyzed click where the compound bears an alkyne or an azide, and the functional element bears the complementary group (e.g., an azide or an alkyne). Mixing these two species together in the presence of an appropriate copper catalyst causes the compound to be covalently conjugated to the functional element through a triazole. Many other bioorthogonal reactions have been reported (for example Patterson, D. M., et al. (2014). "Finding the Right (Bioorthogonal) Chemistry." ACS Chemical Biology 9(3): 592-605.; herein incorporated by reference in its entirety), and compounds (e.g., comprising CC-1852, CC-1861, CTx-0294885, analogs or derivatives thereof (e.g., CC-1816, CC-1817, CC-1803, CC-1804, CC-1290, CC1294, etc.), etc.) and functional elements incorporating complementary reactive species are embodiments of the present invention.

In some embodiments, compounds herein (e.g., comprising CC-1852, CC-1861, CTx-0294885, analogs or derivatives thereof (e.g., CC-1816, CC-1817, CC-1803, CC-1804, CC-1290, CC1294, etc.), etc.) are tethered to a functional element (e.g., detectable element, solid surface, etc.) by a suitable linker. In some embodiments, linkers connecting the compounds herein (e.g., comprising CC-1852, CC-1861, CTx-0294885, analogs or derivatives thereof (e.g., CC-1816, CC-1817, CC-1803, CC-1804, CC-1290, CC1294, etc.), etc.) to a functional element (e.g., detectable element, solid surface, etc.) are provided as part of the compositions herein.

In some embodiments, a linker provides sufficient distance between compounds herein (e.g., CC-1852, CC-1861, CTx-0294885, analogs or derivatives thereof (e.g., CC-1816, CC-1817, CC-1803, CC-1804, CC-1290, CC-1294, etc.), etc.) and functional elements (e.g., detectable element, solid surface, etc.) to allow each to function undisturbed (or minimally disturbed by the linkage to the other. For example, linkers provide sufficient distance to allow a kinase binding agent to bind a kinase and detectable moiety to be detectable (e.g., without or with minimal interference between the two). In some embodiments, a linker separates a compound herein (e.g., CC-1852, CC-1861, CC-CTx-0294885, analogs or derivatives thereof (e.g., CC-1816, CC-1817, CC-1803, CC-1804, CC-1290, CC1294, etc.), etc.) and a functional element (e.g., detectable element, solid surface, etc.) by 5 angstroms to 1000 angstroms, inclusive, in length. Suitable linkers separate a compound herein and a functional element by 5 Å, 10 Å, 20 Å, 50 Å, 100 Å, 150 Å, 200 Å, 300 Å, 400 Å, 500 Å, 600 Å, 700 Å, 800 Å, 900 Å, 1000 Å, and any suitable ranges therein (e.g., 5-100 Å, 50-500 Å, 150-700 Å, etc.). In some embodiments, the linker separates a compound herein and a functional element by 1-200 atoms (e.g., 1, 2, 3, 4, 5, 6, 7, 8, 9, 10, 15, 20, 25, 30, 35, 40, 45, 50, 60, 70, 80, 90, 100, 120, 140, 160, 180, 200, or any suitable ranges therein (e.g., 2-20, 10-50, etc.)).

In some embodiments, a linker comprises 1 or more (e.g., 1-20 (e.g., 1, 2, 3, 4, 5, 6, 7, 8, 9, 10, 11, 12, 13, 14, 15, 16, 17, 18, 19, 20, or any ranges therebetween) —(CH$_2$)$_2$O— (oxyethylene) groups (e.g., —(CH$_2$)$_2$O—(CH$_2$)$_2$O—(CH$_2$)$_2$O—(CH$_2$)$_2$O—, —(CH$_2$)$_2$O—(CH$_2$)$_2$O—(CH$_2$)$_2$O—(CH$_2$)$_2$ O—(CH$_2$)$_2$O—, —(CH$_2$)$_2$O—(CH$_2$)$_2$O—(CH$_2$)$_2$O—(CH$_2$)$_2$O—(CH$_2$)$_2$O—, etc.). In some embodiments, the linker is —(CH$_2$)$_2$O—(CH$_2$)$_2$O—(CH$_2$)$_2$O—(CH$_2$)$_2$O—.

In some embodiments, a linker is attached to a compound herein (e.g., CC-1852, CC-1861, CTx-0294885, analogs or derivatives thereof (e.g., CC-1816, CC-1817, CC-1803, CC-1804, CC-1290, CC1294, etc.), etc.) at the 4-position of the piperazine of a compound herein (e.g., CC-1852, CC-1861, CTx-0294885, analogs or derivatives thereof (e.g., CC-1816, CC-1817, CC-1803, CC-1804, CC-1290, CC1294, etc.), etc.). In some embodiments, the N at the 4-position of the piperazine of a compound herein (e.g., CC-1852, CC-1861, CTx-0294885, analogs or derivatives thereof (e.g., CC-1816, CC-1817, CC-1803, CC-1804, CC-1290, CC1294, etc.), etc.) forms an amide bond with the terminus of a linker. In some embodiments, a linker comprises one or more (e.g., 2, 3, 4, 5, 6, or more or ranges therebetween) amides.

In some embodiments, a linker comprises two or more "linker moieties" ($L^1$, $L^2$, etc.). In some embodiments, a linker comprises a cleavable (e.g., enzymatically cleavable, chemically cleavable, etc.) moiety (Y) and 0, 1, 2, of more "linker moieties" ($L^1$, $L^2$, etc.). In some embodiments, linker moieties are straight or branched chains comprising any combination of alkyl, alkenyl, or alkynyl chains, and mainchain heteroatoms (e.g., O, S, N, P, etc.). In some embodiments, linker moieties comprises one or more backbone groups selected from of: —O—, —S—, —CH=CH—, =C=, a carbon-carbon triple bond, C=O, NH, SH, OH, CN, etc. In some embodiments, a linker moiety comprises one or more substituents, pendants, side chains, etc., comprising any suitable organic functional groups (e.g., OH, NH2, CN, =O, SH, halogen (e.g., Cl, Br, F, I), COOH, CH3, etc.).

In particular embodiments, a linker moiety comprises an alkyl carbamate group (e.g., $(CH_2)_n$OCONH, $(CH_2)_n$NHCOO, etc.). In some embodiments, the alkyl carbamate is oriented such the COO end is oriented toward the compound herein (e.g., CC-1852, CC-1861, CTx-0294885, analogs or derivatives thereof (e.g., CC-1816, CC-1817, CC-1803, CC-1804, CC-1290, CC1294, etc.), etc.), and the NH end is oriented toward the functional element. In some embodiments, the alkyl carbamate is oriented such the NH end is oriented toward the compound and the COO end is oriented toward the functional element. In some embodiments, a linker or linker moiety comprises a single alkyl carbamate group. In some embodiments, a linker or linker moiety comprises two or more alkyl carbamate groups (e.g., 2, 3, 4, 5, 6, 7, 8, etc.).

In some embodiments, a linker moiety comprises more than 1 linearly connected C, S, N, and/or O atoms. In some embodiments, a linker moiety comprises one or more alkyl carbamate groups. In some embodiments, a linker moiety comprises one or more alkyl groups (e.g., methyl, ethyl, propyl, butyl, pentyl, hexyl, etc.). In some embodiments, a linker moiety comprises 1-200 linearly connected atoms (e.g., 1, 2, 3, 4, 5, 6, 7, 8, 9, 10, 15, 20, 25, 30, 35, 40, 45, 50, 60, 70, 80, 90, 100, 120, 140, 160, 180, 200, or any suitable ranges therein (e.g., 2-20, 10-50, 6-18)). In some embodiments, a linker moiety is 1-200 linearly connected atoms (e.g., 1, 2, 3, 4, 5, 6, 7, 8, 9, 10, 15, 20, 25, 30, 35, 40, 45, 50, 60, 70, 80, 90, 100, 120, 140, 160, 180, 200, or any suitable ranges therein (e.g., 2-20, 10-50, 6-18)) in length.

In some embodiments, a compound herein (e.g., CC-1852, CC-1861, CTx-0294885, analogs or derivatives thereof (e.g., CC-1816, CC-1817, CC-1803, CC-1804, CC-1290, CC1294, etc.), etc.) is attached (e.g., directly or via a linker) to a functional element (e.g., detectable element, capture element, solid surface, etc.).

In some embodiments, the compositions described herein (e.g., comprising CC-1852, CC-1861, CTx-0294885, analogs or derivatives thereof (e.g., CC-1816, CC-1817, CC-1803, CC-1804, CC-1290, CC1294, etc.), etc.) are biocompatible (e.g., cell compatible) and/or cell permeable.

Therefore, in some embodiments, suitable functional elements (e.g., detectable, capture elements) are ones that are cell compatible and/or cell permeable within the context of such compositions. In some embodiments, a composition comprising an addition element, when added extracellularly, is capable of crossing the cell membrane to enter a cell (e.g., via diffusion, endocytosis, active transport, passive transport, etc.). In some embodiments, suitable functional elements and linkers are selected based on cell compatibility and/or cell permeability, in addition to their particular function.

In certain embodiments, functional elements have a detectable property that allows for detection of the compound herein (e.g., comprising CC-1852, CC-1861, CTx-0294885, analogs or derivatives thereof (e.g., CC-1816, CC-1817, CC-1803, CC-1804, CC-1290, CC1294, etc.), etc.) or an analyte (e.g., kinase) bound thereto. Detectable functional elements include those with a characteristic electromagnetic spectral property such as emission or absorbance, magnetism, electron spin resonance, electrical capacitance, dielectric constant, or electrical conductivity as well as functional groups which are ferromagnetic, paramagnetic, diamagnetic, luminescent, electrochemiluminescent, fluorescent, phosphorescent, chromatic, antigenic, or have a distinctive mass. A functional element includes, but is not limited to, a nucleic acid molecule (e.g., DNA or RNA (e.g., an oligonucleotide or nucleotide), a protein (e.g., a luminescent protein, a peptide, a contrast agent (e.g., MM contract agent), a radionuclide, an affinity tag (e.g., biotin or streptavidin), a hapten, an amino acid, a lipid, a lipid bilayer, a solid support, a fluorophore, a chromophore, a reporter molecule, a radionuclide, an electron opaque molecule, a MM contrast agent (e.g., manganese, gadolinium(III), or iron-oxide particles), or a coordinator thereof, and the like. Methods to detect a particular functional element, or to isolate a composition comprising a particular functional element and anything bound thereto, are understood.

In some embodiments, a functional group is or comprises a solid support. Suitable solid supports include a sedimental particle such as a magnetic particle, a sepharose, or cellulose bead; a membrane; glass, e.g., glass slides; cellulose, alginate, plastic, or other synthetically prepared polymer (e.g., an Eppendorf tube or a well of a multi-well plate); self-assembled monolayers; a surface plasmon resonance chip; or a solid support with an electron conducting surface; etc.

Exemplary detectable functional elements include haptens (e.g., molecules useful to enhance immunogenicity such as keyhole limpet hemacyanin), cleavable labels (e.g., photocleavable biotin) and fluorescent labels (e.g., N-hydroxysuccinimide (NETS) modified coumarin and succinimide or sulfonosuccinimide modified BODIPY (which can be detected by UV and/or visible excited fluorescence detection), rhodamine (R110, rhodols, CRG6, Texas Methyl Red (TAMRA), Rox5, FAM, or fluorescein), coumarin derivatives (e.g., 7 aminocoumarin, and 7-hydroxycoumarin, 2-amino-4-methoxynapthalene, 1-hydroxypyrene, resorufin, phenalenones or benzphenalenones (U.S. Pat. No. 4,812,409)), acridinones (U.S. Pat. No. 4,810,636), anthracenes, and derivatives of alpha and beta-naphthol, fluorinated xanthene derivatives including fluorinated fluoresceins and rhodols (e.g., U.S. Pat. No. 6,162,931), and bioluminescent molecules (e.g., luciferase (e.g., Oplophorus-derive luciferase (See e.g., U.S. application Ser. No. 12/773,002; U.S. application Ser. No. 13/287,986; herein incorporated by reference in their entireties) or GFP or GFP derivatives). A fluorescent (or bioluminescent) functional element may be used to sense changes in a system, like phosphorylation, in real-time. A fluorescent molecule, such as a chemosensor of metal ions, may be employed to label proteins which bind the composition. A bioluminescent or fluorescent functional group such as BODIPY, rhodamine green, GFP, or infrared dyes, finds use as a functional element and may, for instance, be employed in interaction studies (e.g., using BRET, FRET, LRET or electrophoresis).

Another class of functional elements includes molecules detectable using electromagnetic radiation and includes, but is not limited to, xanthene fluorophores, dansyl fluorophores, coumarins and coumarin derivatives, fluorescent acridinium moieties, benzopyrene-based fluorophores as well as 7-nitrobenz-2-oxa-1,3-diazole, and 3-N-(7-nitrobenz-2-oxa-1,3-diazol-4-yl)-2,3-diamino-propionic acid. Preferably, the fluorescent molecule has a high quantum yield of fluorescence at a wavelength different from native amino acids and more preferably has high quantum yield of fluorescence that can be excited in the visible, or in both the UV and visible, portion of the spectrum. Upon excitation at a preselected wavelength, the molecule is detectable at low concentrations either visually or using conventional fluorescence detection methods. Electrochemiluminescent molecules such as ruthenium chelates and its derivatives or nitroxide amino acids and their derivatives are detectable at femtomolar ranges and below.

In some embodiments, a functional element is a fluorophore. Suitable fluorophores for linking to the compounds herein (e.g., to form a fluorescent tracer) include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLuoR (Invitrogen), DYLIGHT FLUOR (Thermo Scientific, Pierce), ATTO and TRACY (Sigma Aldrich), FluoProbes (Interchim), DY and MEGASTOKES (Dyomics), SULFO CY dyes (CYANDYE, LLC), SETAU AND SQUARE DYES (SETA BioMedicals), QUASAR and CAL FLUOR dyes (Biosearch Technologies), SURELIGHT DYES (APC, RPE, PerCP, Phycobilisomes)(Columbia Biosciences), APC, APCXL, RPE, BPE (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog) such as those described in U.S. patent application Ser. No. 13/682,589, herein incorporated by reference in its entirety.

In addition to fluorescent molecules, a variety of molecules with physical properties based on the interaction and response of the molecule to electromagnetic fields and radiation find use in the compositions and methods described herein. These properties include absorption in the UV, visible, and infrared regions of the electromagnetic spectrum, presence of chromophores that are Raman active and can be further enhanced by resonance Raman spectroscopy, electron spin resonance activity, and nuclear magnetic resonances and molecular mass, e.g., via a mass spectrometer.

In some embodiments, a functional element is a capture element. In some embodiments, a capture element is a substrate for a protein (e.g., enzyme), and the capture agent is that protein. In some embodiments, a capture element is a "covalent substrate" or one that forms a covalent bond with a protein or enzyme that it reacts with. The substrate may comprise a reactive group (e.g., a modified substrate) that forms a covalent bond with the enzyme upon interaction with the enzyme, or the enzyme may be a mutant version that is unable to reconcile a covalently bound intermediate with the substrate. In some embodiments, the substrate is recognized by a mutant protein (e.g., mutant dehalogenase), which forms a covalent bond thereto. In such embodiments, while the interaction of the substrate and a wild-type version of the protein (e.g., dehalogenase) results in a product and the regeneration of the wild-type protein, interaction of the substrate (e.g., haloalkane) with the mutant version of the protein (e.g., dehalogenase) results in stable bond formation (e.g., covalent bond formation) between the protein and substrate. The substrate may be any suitable substrate for any mutant protein that has been altered to form an ultrastable or covalent bond with its substrate that would ordinarily only transiently bound by the protein. In some embodiments, the protein is a mutant hydrolase or dehalogenase. In some embodiments, the protein is a mutant dehalogenase and the substrate is a haloalkane. In some embodiments, the haloalkane comprises an alkane (e.g., $C_2$-$C_{20}$) capped by a terminal halogen (e.g., Cl, Br, F, I, etc.). In some embodiments, the haloalkane is of the formula A-X, wherein X is a halogen (e.g., Cl, Br, F, I, etc.), and wherein A is an alkane comprising 2-20 carbons. In certain embodiments, A comprises a straight-chain segment of 2-12 carbons. In certain embodiments, A is a straight-chain segment of 2-12 carbons. In some embodiments, the haloalkane may comprise any additional pendants or substitutions that do not interfere with interaction with the mutant dehalogenase.

In some embodiments, a capture agent is a SNAP-Tag and a capture element is benzyl guanine (See, e.g., Crivat G, Taraska J W (January 2012). *Trends in Biotechnology* 30 (1): 8-16.; herein incorporated by reference in its entirety). In some embodiments, a capture agent is a CLIP-Tag and a capture element is benzyl cytosine (See, e.g., Gautier, et al. Chem Biol. 2008 February; 15(2):128-36.; herein incorporated by reference in its entirety).

Systems comprising mutant proteins (e.g., mutant hydrolases (e.g., mutant dehalogenases) that covalently bind their substrates (e.g., haloalkane substrates) are described, for example, in U.S. Pat. Nos. 7,238,842; 7,425,436; 7,429,472; 7,867,726; each of which is herein incorporated by reference in their entireties.

In some embodiments, a functional element is an affinity element (e.g., that binds to an affinity agent). Examples of such pairs would include: an antibody as the affinity agent and an antigen as the affinity element; a His-tag as the affinity element and a nickel column as the affinity agent; a protein and small molecule with high affinity as the affinity agent and affinity element, respectively (e.g., streptavidin and biotin), etc. Examples of affinity molecules include molecules such as immunogenic molecules (e.g., epitopes of proteins, peptides, carbohydrates, or lipids (e.g., any molecule which is useful to prepare antibodies specific for that molecule)); biotin, avidin, streptavidin, and derivatives thereof; metal binding molecules; and fragments and combinations of these molecules. Exemplary affinity molecules include His5 (HHHHH)(SEQ ID NO: 1), HisX6 (HHHHHH)(SEQ ID NO: 2), C-myc (EQKLISEEDL) (SEQ ID NO: 3), Flag (DYKDDDDK) (SEQ ID NO: 4), SteptTag (WSHPQFEK)(SEQ ID NO: 5), HA Tag (YPYDVPDYA) (SEQ ID NO: 6), thioredoxin, cellulose binding domain, chitin binding domain, S-peptide, T7 peptide, calmodulin binding peptide, C-end RNA tag, metal binding domains, metal binding reactive groups, amino acid reactive groups, inteins, biotin, streptavidin, and maltose binding protein. Another example of an affinity molecule is dansyllysine. Antibodies that interact with the dansyl ring are commercially available (Sigma Chemical; St. Louis, Mo.) or can be prepared using known protocols such as described in Antibodies: A Laboratory Manual (Harlow and Lane, 1988).

In some embodiments, provided herein are methods of using the compounds herein (e.g., comprising CC-1852, CC-1861, CTx-0294885, analogs or derivatives thereof (e.g., CC-1816, CC-1817, CC-1803, CC-1804, CC-1290, CC1294, etc.), etc.) alone or attached to a functional element (e.g., directly of via a suitable linker) to detect, isolate, analyze, characterize, etc., kinases within a system (e.g., a cell, a cell lysate, a sample, a biochemical solution or mixture, a tissue, an organism, etc.).

In some embodiments, provided herein are methods of detecting one or more kinases in a sample, the method comprising contacting the sample with a compound herein (e.g., comprising CC-1852, CC-1861, CTx-0294885, analogs or derivatives thereof (e.g., CC-1816, CC-1817, CC-1803, CC-1804, CC-1290, CC1294, etc.), etc.). In some embodiments, provided herein are methods to isolate one or more kinases from a sample.

In some embodiments, methods are provided for characterizing a sample by analyzing the presence, quantity, and or population of kinases in the sample (e.g., what kinases are present and/or at what quantities) by contacting the sample with a compound herein (e.g., comprising CC-1852, CC-1861, CTx-0294885, analogs or derivatives thereof (e.g., CC-1816, CC-1817, CC-1803, CC-1804, CC-1290, CC1294, etc.), etc.).

In some embodiments, provided herein are methods of diagnosing a disease of condition comprising detecting the presence or quantity of one or more kinases in a sample from the subject by contacting the sample with a compound herein (e.g., comprising CC-1852, CC-1861, CTx-0294885, analogs or derivatives thereof (e.g., CC-1816, CC-1817, CC-1803, CC-1804, CC-1290, CC1294, etc.), etc.), wherein the presence or quantity of the one or more of the kinases in the sample is indicative of the disease, condition, or a predisposition thereto.

In some embodiments, provided herein are methods of monitoring a subject's response to a therapeutic treatment comprising: (a) detecting the presence or quantity of one or more kinases in a sample from the subject by contacting the sample with compound herein (e.g., comprising CC-1852, CC-1861, CTx-0294885, analogs or derivatives thereof (e.g., CC-1816, CC-1817, CC-1803, CC-1804, CC-1290, CC1294, etc.), etc.) prior to administration of the therapeutic treatment, and (b) detecting the presence or quantity of one or more kinases in a sample from the subject by contacting the sample with compound herein (e.g., comprising CC-1852, CC-1861, CTx-0294885, analogs or derivatives thereof (e.g., CC-1816, CC-1817, CC-1803, CC-1804, CC-1290, CC1294, etc.), etc.) following administration of the therapeutic treatment, wherein a change in the presence of quantity of the one or more kinases is indicative of the subject's response to the therapeutic treatment.

In some embodiments, kinases bound by the compounds herein are detected, quantified, and/or isolated by taking advantage of unique properties of the compound and/or the functional element bound thereto by any means including electrophoresis, gel filtration, high-pressure or fast-pressure liquid chromatography, mass spectroscopy, affinity chromatography, ion exchange chromatography, chemical extraction, magnetic bead separation, precipitation, hydrophobic interaction chromatography (HIC), or any combination thereof. The isolated kinase(s) may be employed for structural and functional studies, for diagnostic applications, for the preparation biological or pharmaceutical reagents, as a tool for the development of drugs, and for studying protein interactions, for the isolation and characterization of protein complexes, etc.

In some embodiments, methods are provided for detecting and/or quantifying a compound herein (e.g., comprising CC-1852, CC-1861, CTx-0294885, analogs or derivatives thereof (e.g., CC-1816, CC-1817, CC-1803, CC-1804, CC-1290, CC1294, etc.), etc.) and/or analyte (e.g., kinases) bound thereto in a sample. In some embodiments, techniques for detection and/or quantification of a compound herein (e.g., comprising CC-1852, CC-1861, CTx-0294885, analogs or derivatives thereof (e.g., CC-1816, CC-1817, CC-1803, CC-1804, CC-1290, CC1294, etc.), etc.) and/or analyte (e.g., kinases) bound thereto depend upon the identity of the functional element attached to the compound (e.g., capture element, affinity element, detectable element (e.g., fluorophore, luciferase, chelated radionuclide, chelated contrast agent, etc.) and/or specific modifications to the compound (e.g., mass tags (e.g., heavy isotopes (e.g., $^{13}C$, $^{15}N$, $^{2}H$, etc.). For example, when a compound herein (e.g., comprising CC-1852, CC-1861, CTx-0294885, analogs or derivatives thereof (e.g., CC-1816, CC-1817, CC-1803, CC-1804, CC-1290, CC1294, etc.), etc.) is linked to a fluorophore or other light emitting functional element, the compound and/or analyte (e.g., kinases) bound thereto may be detected/quantified in a sample using systems, devices, and/or apparatuses that are provided to detect, quantitate, or monitor, the amount of light (e.g., fluorescence) emitted, or changes thereto. In some embodiments, detection, quantification, and/or monitoring are provided by a device, system or apparatus comprising one or more of a spectrophotometer, fluorometer, luminometer, photomultiplier tube, photodiode, nephlometer, photon counter, electrodes, ammeter, voltmeter, capacitative sensors, flow cytometer, CCD, etc.

In addition to fluorescent functional elements, a variety of functional elements with physical properties based on the interaction and response of the functional elements to electromagnetic fields and radiation can be used to detect the compound herein (e.g., comprising CC-1852, CC-1861, CTx-0294885, analogs or derivatives thereof (e.g., CC-1816, CC-1817, CC-1803, CC-1804, CC-1290, CC1294, etc.), etc.) and/or a bound kinase. These properties include absorption in the UV, visible, and infrared regions of the electromagnetic spectrum, presence of chromophores that are Raman active and can be further enhanced by resonance Raman spectroscopy, electron spin resonance activity and nuclear magnetic resonances and molecular mass, e.g., via a mass spectrometer.

In some embodiments, systems are provided comprising: (a) a fusion of a protein kinase (e.g., of Table 1A-O or a variant thereof) and a bioluminescent protein; and (b) a broad-spectrum kinase binding moiety herein linked to a fluorophore; wherein the emission spectrum of the bioluminescent protein overlaps the excitation spectrum of the fluorophore, such that BRET is detectable between the bioluminescent protein and the fluorophore when the broad-spectrum kinase binding moiety binds to the protein kinase. Similar BRET systems (e.g., utilizing a NANOLUC® luciferase) are described in, for example, Intl. Pat. App.

PCT/US13/74765 (herein incorporated by reference in its entirety); embodiments of which will find use in the systems and methods herein.

In some embodiments, the compounds herein bind a broad spectrum of kinases, including protein kinases are of the following common families or subgroups: AGC (e.g., containing the PKA, PKG and PKC subfamilies), CAMK (e.g., calcium/calmodulin-dependent protein kinases), CK1 (e.g., casein kinase 1), CMGC (e.g., containing the CDK, MAPK, GSK3 and CLK subfamilies), NEK, RGC (e.g., receptor guanylate cyclases), STE, TKL (e.g., tyrosine protein kinase-like), and Tyr (e.g., tyrosine protein kinase). In some embodiments, the compounds herein bind to one or more kinases of atypical kinase families, such as, ADCK, alpha-type, FAST, PDK/BCKDK, PI3/PI4-kinase, RIO-type, etc. In some embodiments, the compounds herein bind to kinases of any suitable organism. In some embodiments, compounds herein bind to human and/or mouse kinases, such as those listed in Tables 1A-O, and/or homologs and analogs from other organisms.

TABLE 1A

AGC Ser/Thr protein kinase family

| | | |
|---|---|---|
| AKT1 | AKT1_HUMAN (P31749) | AKT1_MOUSE (P31750) |
| AKT2 | AKT2_HUMAN (P31751) | AKT2_MOUSE (Q60823) |
| AKT3 | AKT3_HUMAN (Q9Y243) | AKT3_MOUSE (Q9WUA6) |
| CDC42BPA | MRCKA_HUMAN (Q5VT25) | MRCKA_MOUSE (Q3UU96) |
| CDC42BPB | MRCKB_HUMAN (Q9Y5S2) | MRCKB_MOUSE (Q7TT50) |
| CDC42BPG | MRCKG_HUMAN (Q6DT37) | MRCKG_MOUSE (Q80UW5) |
| CIT | CTRO_HUMAN (O14578) | CTRO_MOUSE (P49025) |
| DMPK | DMPK_HUMAN (Q09013) | DMPK_MOUSE (P54265) |
| GRK1 | RK_HUMAN (Q15835) | RK_MOUSE (Q9WVL4) |
| GRK2 | ARBK1_HUMAN (P25098) | ARBK1_MOUSE (Q99MK8) |
| GRK3 | ARBK2_HUMAN (P35626) | ARBK2_MOUSE (Q3UYH7) |
| GRK4 | GRK4_HUMAN (P32298) | GRK4_MOUSE (O70291) |
| GRK5 | GRK5_HUMAN (P34947) | GRK5_MOUSE (Q8VEB1) |
| GRK6 | GRK6_HUMAN (P43250) | GRK6_MOUSE (O70293) |
| GRK7 | GRK7_HUMAN (Q8WTQ7) | |
| LATS1 | LATS1_HUMAN (O95835) | LATS1_MOUSE (Q8BYR2) |
| LATS2 | LATS2_HUMAN (Q9NRM7) | LATS2_MOUSE (Q7TSJ6) |
| MAST1 | MAST1_HUMAN (Q9Y2H9) | MAST1_MOUSE (Q9R1L5) |
| MAST2 | MAST2_HUMAN (Q6P0Q8) | MAST2_MOUSE (Q60592) |
| MAST3 | MAST3_HUMAN (O60307) | MAST3_MOUSE (Q3U214) |
| MAST4 | MAST4_HUMAN (O15021) | MAST4_MOUSE (Q811L6) |
| MASTL | GWL_HUMAN (Q96GX5) | GWL_MOUSE (Q8C0P0) |
| PDPK1 | PDPK1_HUMAN (O15530) | PDPK1_MOUSE (Q9Z2A0) |
| PDPK2P | PDPK2_HUMAN (Q6A1A2) | |
| PKN1 | PKN1_HUMAN (Q16512) | PKN1_MOUSE (P70268) |
| PKN2 | PKN2_HUMAN (Q16513) | PKN2_MOUSE (Q8BWW9) |
| PKN3 | PKN3_HUMAN (Q6P5Z2) | PKN3_MOUSE (Q8K045) |
| PRKACA | KAPCA_HUMAN (P17612) | KAPCA_MOUSE (P05132) |
| PRKACB | KAPCB_HUMAN (P22694) | KAPCB_MOUSE (P68181) |
| PRKACG | KAPCG_HUMAN (P22612) | |
| PRKCA | KPCA_HUMAN (P17252) | KPCA_MOUSE (P20444) |
| PRKCB | KPCB_HUMAN (P05771) | KPCB_MOUSE (P68404) |
| PRKCD | KPCD_HUMAN (Q05655) | KPCD_MOUSE (P28867) |
| PRKCE | KPCE_HUMAN (Q02156) | KPCE_MOUSE (P16054) |
| PRKCG | KPCG_HUMAN (P05129) | KPCG_MOUSE (P63318) |
| PRKCH | KPCL_HUMAN (P24723) | KPCL_MOUSE (P23298) |
| PRKCI | KPCI_HUMAN (P41743) | KPCI_MOUSE (Q62074) |
| PRKCQ | KPCT_HUMAN (Q04759) | KPCT_MOUSE (Q02111) |
| PRKCZ | KPCZ_HUMAN (Q05513) | KPCZ_MOUSE (Q02956) |
| PRKG1 | KGP1_HUMAN (Q13976) | KGP1_MOUSE (P0C605) |
| PRKG2 | KGP2_HUMAN (Q13237) | KGP2_MOUSE (Q61410) |
| PRKX | PRKX_HUMAN (P51817) | PRKX_MOUSE (Q922R0) |
| PRKY | PRKY_HUMAN (O43930) | |
| ROCK1 | ROCK1_HUMAN (Q13464) | ROCK1_MOUSE (P70335) |
| ROCK2 | ROCK2_HUMAN (O75116) | ROCK2_MOUSE (P70336) |
| RPS6KA1 | KS6A1_HUMAN (Q15418) | KS6A1_MOUSE (P18653) |
| RPS6KA2 | KS6A2_HUMAN (Q15349) | KS6A2_MOUSE (Q9WUT3) |

TABLE 1A-continued

AGC Ser/Thr protein kinase family

| | | |
|---|---|---|
| RPS6KA3 | KS6A3_HUMAN (P51812) | KS6A3_MOUSE (P18654) |
| RPS6KA4 | KS6A4_HUMAN (O75676) | KS6A4_MOUSE (Q9Z2B9) |
| RPS6KA5 | KS6A5_HUMAN (O75582) | KS6A5_MOUSE (Q8C050) |
| RPS6KA6 | KS6A6_HUMAN (Q9UK32) | KS6A6_MOUSE (Q7TPSO) |
| RPS6KB1 | KS6B1_HUMAN (P23443) | KS6B1_MOUSE (Q8BSK8) |
| RPS6KB2 | KS6B2_HUMAN (Q9UBS0) | KS6B2_MOUSE (Q9Z1M4) |
| SGK1 | SGK1_HUMAN (O00141) | SGK1_MOUSE (Q9WVC6) |
| SGK2 | SGK2_HUMAN (Q9HBY8) | SGK2_MOUSE (Q9QZS5) |
| SGK3 | SGK3_HUMAN (Q96BR1) | SGK3_MOUSE (Q9ERE3) |
| STK38 | STK38_HUMAN (Q15208) | STK38_MOUSE (Q91VJ4) |
| STK38L | ST38L_HUMAN (Q9Y2H1) | ST38L_MOUSE (Q7TSE6) |

TABLE 1B

CAMK Ser/Thr protein kinase family

| | | |
|---|---|---|
| | | SMKX_MOUSE (Q8C0X8) |
| BRSK1 | BRSK1_HUMAN (Q8TDC3) | BRSK1_MOUSE (Q5RJI5) |
| BRSK2 | BRSK2_HUMAN (Q8IWQ3) | BRSK2_MOUSE (Q69Z98) |
| CAMK1 | KCC1A_HUMAN (Q14012) | KCC1A_MOUSE (Q91YS8) |
| CAMK1D | KCC1D_HUMAN (Q8IU85) | KCC1D_MOUSE (Q8BW96) |
| CAMK1G | KCC1G_HUMAN (Q96NX5) | KCC1G_MOUSE (Q91VB2) |
| CAMK2A | KCC2A_HUMAN (Q9UQM7) | KCC2A_MOUSE (P11798) |
| CAMK2B | KCC2B_HUMAN (Q13554) | KCC2B_MOUSE (P28652) |
| CAMK2D | KCC2D_HUMAN (Q13557) | KCC2D_MOUSE (Q6PHZ2) |
| CAMK2G | KCC2G_HUMAN (Q13555) | KCC2G_MOUSE (Q923T9) |
| CAMK4 | KCC4_HUMAN (Q16566) | KCC4_MOUSE (P08414) |
| CAMKV | CAMKV_HUMAN (Q8NCB2) | CAMKV_MOUSE (Q3UHL1) |
| CASK | CSKP_HUMAN (O14936) | CSKP_MOUSE (O70589) |
| CHEK1 | CHK1_HUMAN (O14757) | CHK1_MOUSE (O35280) |
| CHEK2 | CHK2_HUMAN (O96017) | CHK2_MOUSE (Q9Z265) |
| DAPK1 | DAPK1_HUMAN (P53355) | DAPK1_MOUSE (Q80YE7) |
| DAPK2 | DAPK2_HUMAN (Q9UIK4) | DAPK2_MOUSE (Q8VDF3) |
| DAPK3 | DAPK3_HUMAN (O43293) | DAPK3_MOUSE (O54784) |
| DCLK1 | DCLK1_HUMAN (O15075) | DCLK1_MOUSE (Q9JLM8) |
| DCLK2 | DCLK2_HUMAN (Q8N568) | DCLK2_MOUSE (Q6PGN3) |
| DCLK3 | DCLK3_HUMAN (Q9C098) | DCLK3_MOUSE (Q8BWQ5) |
| Gm4922 | | SMKZ_MOUSE (Q8C0N0) |
| Gm7168 | | SMKY_MOUSE (A0AUV4) |
| HUNK | HUNK_HUMAN (P57058) | HUNK_MOUSE (O88866) |
| KALRN | KALRN_HUMAN (O60229) | KALRN_MOUSE (A2CG49) |
| MAPKAPK2 | MAPK2_HUMAN (P49137) | MAPK2_MOUSE (P49138) |
| MAPKAPK3 | MAPK3_HUMAN (Q16644) | MAPK3_MOUSE (Q3UMW7) |
| MAPKAPK5 | MAPK5_HUMAN (Q8IW41) | MAPK5_MOUSE (O54992) |
| MARK1 | MARK1_HUMAN (Q9P0L2) | MARK1_MOUSE (Q8VHJ5) |
| MARK2 | MARK2_HUMAN (Q7KZI7) | MARK2_MOUSE (Q05512) |
| MARK3 | MARK3_HUMAN (P27448) | MARK3_MOUSE (Q03141) |
| MARK4 | MARK4_HUMAN (Q96L34) | MARK4_MOUSE (Q8CIP4) |
| MELK | MELK_HUMAN (Q14680) | MELK_MOUSE (Q61846) |
| MKNK1 | MKNK1_HUMAN (Q9BUB5) | MKNK1_MOUSE (O08605) |
| MKNK2 | MKNK2_HUMAN (Q9HBH9) | MKNK2_MOUSE (Q8CDB0) |
| MYLK | MYLK_HUMAN (Q15746) | MYLK_MOUSE (Q6PDN3) |
| MYLK2 | MYLK2_HUMAN (Q9H1R3) | MYLK2_MOUSE (Q8VCR8) |
| MYLK3 | MYLK3_HUMAN (Q32MK0) | MYLK3_MOUSE (Q3UIZ8) |
| MYLK4 | MYLK4_HUMAN (Q86YV6) | MYLK4_MOUSE (Q5SUV5) |
| NIM1K | NIM1_HUMAN (Q8IY84) | NIM1_MOUSE (Q8BHI9) |
| NUAK1 | NUAK1_HUMAN (O60285) | NUAK1_MOUSE (Q641K5) |
| NUAK2 | NUAK2_HUMAN (Q9H093) | NUAK2_MOUSE (Q8BZN4) |
| OBSCN | OBSCN_HUMAN (Q5VST9) | OBSCN_MOUSE (A2AAJ9) |
| PASK | PASK_HUMAN (Q96RG2) | PASK_MOUSE (Q8CEE6) |
| PHKG1 | PHKG1_HUMAN (Q16816) | PHKG1_MOUSE (P07934) |
| PHKG2 | PHKG2_HUMAN (P15735) | PHKG2_MOUSE (Q9DB30) |
| PIM1 | PIM1_HUMAN (P11309) | PIM1_MOUSE (P06803) |
| PIM2 | PIM2_HUMAN (Q9P1W9) | PIM2_MOUSE (Q62070) |
| PIM3 | PIM3_HUMAN (Q86V86) | PIM3_MOUSE (P58750) |
| PNCK | KCC1B_HUMAN (Q6P2M8) | KCC1B_MOUSE (Q9QYK9) |

TABLE 1B-continued

CAMK Ser/Thr protein kinase family

| | | |
|---|---|---|
| PRKAA1 | AAPK1_HUMAN (Q13131) | AAPK1_MOUSE (Q5EG47) |
| PRKAA2 | AAPK2_HUMAN (P54646) | AAPK2_MOUSE (Q8BRK8) |
| PRKD1 | KPCD1_HUMAN (Q15139) | KPCD1_MOUSE (Q62101) |
| PRKD2 | KPCD2_HUMAN (Q9BZL6) | KPCD2_MOUSE (Q8BZ03) |
| PRKD3 | KPCD3_HUMAN (O94806) | KPCD3_MOUSE (Q8K1Y2) |
| PSKH1 | KPSH1_HUMAN (P11801) | KPSH1_MOUSE (Q91YA2) |
| PSKH2 | KPSH2_HUMAN (Q96Q56) | |
| SIK1 | SIK1_HUMAN (P57059) | SIK1_MOUSE (Q60670) |
| SIK2 | SIK2_HUMAN (Q9H0K1) | SIK2_MOUSE (Q8CFH6) |
| SIK3 | SIK3_HUMAN (Q9Y2K2) | SIK3_MOUSE (Q6P456) |
| SNRK | SNRK_HUMAN (Q9NRH2) | SNRK_MOUSE (Q8VDU5) |
| SPEG | SPEG_HUMAN (Q15772) | SPEG_MOUSE (Q62407) |
| STK11 | STK11_HUMAN (Q15831) | STK11_MOUSE (Q9WTK7) |
| STK17A | ST17A_HUMAN (Q9UEE5) | |
| STK17B | ST17B_HUMAN (O94768) | ST17B_MOUSE (Q8BG48) |
| STK33 | STK33_HUMAN (Q9BYT3) | STK33_MOUSE (Q924X7) |
| STK40 | STK40_HUMAN (Q8N2I9) | STK40_MOUSE (Q7TNL3) |
| Smok2a | | SMK2A_MOUSE (Q9QYZ6) |
| | | SMK2B_MOUSE (Q9QYZ3) |
| Smok2b | | |
| Smok3a | | SMK3A_MOUSE (C0HKC8) |
| Smok3b | | SMK3B_MOUSE (C0HKC9) |
| Stk-ps2 | | SMKW_MOUSE (Q8C0V7) |
| TRIB1 | TRIB1_HUMAN (Q96RU8) | TRIB1_MOUSE (Q8K4K4) |
| TRIB2 | TRIB2_HUMAN (Q92519) | TRIB2_MOUSE (Q8K4K3) |
| TRIB3 | TRIB3_HUMAN (Q96RU7) | TRIB3_MOUSE (Q8K4K2) |
| TRIO | TRIO_HUMAN (O75962) | TRIO_MOUSE (Q0KL02) |
| TSSK1B | TSSK1_HUMAN (Q9BXA7) | TSSK1_MOUSE (Q61241) |
| TSSK2 | TSSK2_HUMAN (Q96PF2) | TSSK2_MOUSE (O54863) |
| TSSK3 | TSSK3_HUMAN (Q96PN8) | TSSK3_MOUSE (Q9D2E1) |
| TSSK4 | TSSK4_HUMAN (Q6SA08) | TSSK4_MOUSE (Q9D411) |
| TSSK6 | TSSK6_HUMAN (Q9BXA6) | TSSK6_MOUSE (Q925K9) |
| TTN | TITIN_HUMAN (Q8WZ42) | TITIN_MOUSE (A2ASS6) |
| Tssk5 | | TSSK5_MOUSE (Q8C1R0) |

TABLE 1C

CK1 Ser/Thr protein kinase family

| | | |
|---|---|---|
| CSNK1A1 | KC1A_HUMAN (P48729) | KC1A_MOUSE (Q8BK63) |
| CSNK1A1L | KC1AL_HUMAN (Q8N752) | |
| CSNK1D | KC1D_HUMAN (P48730) | KC1D_MOUSE (Q9DC28) |
| CSNK1E | KC1E_HUMAN (P49674) | KC1E_MOUSE (Q9JMK2) |
| CSNK1G1 | KC1G1_HUMAN (Q9HCP0) | KC1G1_MOUSE (Q8BTH8) |
| CSNK1G2 | KC1G2_HUMAN (P78368) | KC1G2_MOUSE (Q8BVP5) |
| CSNK1G3 | KC1G3_HUMAN (Q9Y6M4) | KC1G3_MOUSE (Q8C4X2) |
| TTBK1 | TTBK1_HUMAN (Q5TCY1) | TTBK1_MOUSE (Q6PCN3) |
| TTBK2 | TTBK2_HUMAN (Q6IQ55) | TTBK2_MOUSE (Q3UVR3) |
| VRK1 | VRK1_HUMAN (Q99986) | VRK1_MOUSE (Q80X41) |
| VRK2 | VRK2_HUMAN (Q86Y07) | VRK2_MOUSE (Q8BN21) |
| VRK3 | VRK3_HUMAN (Q8IV63) | VRK3_MOUSE (Q8K3G5) |

TABLE 1D

CMGC Ser/Thr protein kinase family

| | | |
|---|---|---|
| CDK1 | CDK1_HUMAN (P06493) | CDK1_MOUSE (P11440) |
| CDK10 | CDK10_HUMAN (Q15131) | CDK10_MOUSE (Q3UMM4) |
| CDK11A | CD11A_HUMAN (Q9UQ88) | |
| CDK11B | CD11B_HUMAN (P21127) | CD11B_MOUSE (P24788) |
| CDK12 | CDK12_HUMAN (Q9NYV4) | CDK12_MOUSE (Q14AX6) |
| CDK13 | CDK13_HUMAN (Q14004) | CDK13_MOUSE (Q69ZA1) |
| CDK14 | CDK14_HUMAN (O94921) | CDK14_MOUSE (O35495) |
| CDK15 | CDK15_HUMAN (Q96Q40) | CDK15_MOUSE (Q3V3A1) |
| CDK16 | CDK16_HUMAN (Q00536) | CDK16_MOUSE (Q04735) |
| CDK17 | CDK17_HUMAN (Q00537) | CDK17_MOUSE (Q8K0D0) |
| CDK18 | CDK18_HUMAN (Q07002) | CDK18_MOUSE (Q04899) |
| CDK19 | CDK19_HUMAN (Q9BWU1) | CDK19_MOUSE (Q8BWD8) |
| CDK2 | CDK2_HUMAN (P24941) | CDK2_MOUSE (P97377) |
| CDK20 | CDK20_HUMAN (Q8IZL9) | CDK20_MOUSE (Q9JHU3) |
| CDK3 | CDK3_HUMAN (Q00526) | CDK3_MOUSE (Q80YP0) |
| CDK4 | CDK4_HUMAN (P11802) | CDK4_MOUSE (P30285) |
| CDK5 | CDK5_HUMAN (Q00535) | CDK5_MOUSE (P49615) |
| CDK6 | CDK6_HUMAN (Q00534) | CDK6_MOUSE (Q64261) |
| CDK7 | CDK7_HUMAN (P50613) | CDK7_MOUSE (Q03147) |
| CDK8 | CDK8_HUMAN (P49336) | CDK8_MOUSE (Q8R3L8) |
| CDK9 | CDK9_HUMAN (P50750) | CDK9_MOUSE (Q99J95) |
| CDKL1 | CDKL1_HUMAN (Q00532) | CDKL1_MOUSE (Q8CEQ0) |
| CDKL2 | CDKL2_HUMAN (Q92772) | CDKL2_MOUSE (Q9QUK0) |
| CDKL3 | CDKL3_HUMAN (Q8IVW4) | CDKL3_MOUSE (Q8BLF2) |
| CDKL4 | CDKL4_HUMAN (Q5MAI5) | CDKL4_MOUSE (Q3TZA2) |
| CDKL5 | CDKL5_HUMAN (O76039) | CDKL5_MOUSE (Q3UTQ8) |
| CLK1 | CLK1_HUMAN (P49759) | CLK1_MOUSE (P22518) |
| CLK2 | CLK2_HUMAN (P49760) | CLK2_MOUSE (O35491) |
| CLK3 | CLK3_HUMAN (P49761) | CLK3_MOUSE (O35492) |
| CLK4 | CLK4_HUMAN (Q9HAZ1) | CLK4_MOUSE (O35493) |
| DYRK1A | DYR1A_HUMAN (Q13627) | DYR1A_MOUSE (Q61214) |
| DYRK1B | DYR1B_HUMAN (Q9Y463) | DYR1B_MOUSE (Q9Z188) |
| DYRK2 | DYRK2_HUMAN (Q92630) | DYRK2_MOUSE (Q5U4C9) |
| DYRK3 | DYRK3_HUMAN (O43781) | DYRK3_MOUSE (Q922Y0) |
| DYRK4 | DYRK4_HUMAN (Q9NR20) | DYRK4_MOUSE (Q8BI55) |
| GSK3A | GSK3A_HUMAN (P49840) | GSK3A_MOUSE (Q2NL51) |
| GSK3B | GSK3B_HUMAN (P49841) | GSK3B_MOUSE (Q9WV60) |
| HIPK1 | HIPK1_HUMAN (Q86Z02) | HIPK1_MOUSE (O88904) |
| HIPK2 | HIPK2_HUMAN (Q9H2X6) | HIPK2_MOUSE (Q9QZR5) |
| HIPK3 | HIPK3_HUMAN (Q9H422) | HIPK3_MOUSE (Q9ERH7) |
| HIPK4 | HIPK4_HUMAN (Q8NE63) | HIPK4_MOUSE (Q3V016) |
| ICK | ICK_HUMAN (Q9UPZ9) | ICK_MOUSE (Q9JKV2) |
| MAK | MAK_HUMAN (P20794) | MAK_MOUSE (Q04859) |
| MAPK1 | MK01_HUMAN (P28482) | MK01_MOUSE (P63085) |
| MAPK10 | MK10_HUMAN (P53779) | MK10_MOUSE (Q61831) |
| MAPK11 | MK11_HUMAN (Q15759) | MK11_MOUSE (Q9WUI1) |
| MAPK12 | MK12_HUMAN (P53778) | MK12_MOUSE (O08911) |
| MAPK13 | MK13_HUMAN (O15264) | MK13_MOUSE (Q9Z1B7) |
| MAPK14 | MK14_HUMAN (Q16539) | MK14_MOUSE (P47811) |
| MAPK15 | MK15_HUMAN (Q8TD08) | MK15_MOUSE (Q80Y86) |
| MAPK3 | MK03_HUMAN (P27361) | MK03_MOUSE (Q63844) |
| MAPK4 | MK04_HUMAN (P31152) | MK04_MOUSE (Q6P5G0) |
| MAPK6 | MK06_HUMAN (Q16659) | MK06_MOUSE (Q61532) |
| MAPK7 | MK07_HUMAN (Q13164) | MK07_MOUSE (Q9WVS8) |
| MAPK8 | MK08_HUMAN (P45983) | MK08_MOUSE (Q91Y86) |
| MAPK9 | MK09_HUMAN (P45984) | MK09_MOUSE (Q9WTU6) |
| MOK | MOK_HUMAN (Q9UQ07) | MOK_MOUSE (Q9WVS4) |
| NLK | NLK_HUMAN (Q9UBE8) | NLK_MOUSE (O54949) |
| PRPF4B | PRP4B_HUMAN (Q13523) | PRP4B_MOUSE (Q61136) |
| SRPK1 | SRPK1_HUMAN (Q96SB4) | SRPK1_MOUSE (O70551) |
| SRPK2 | SRPK2_HUMAN (P78362) | SRPK2_MOUSE (O54781) |
| SRPK3 | SRPK3_HUMAN (Q9UPE1) | SRPK3_MOUSE (Q9Z0G2) |

TABLE 1E

NEK Ser/Thr protein kinase family

| | | |
|---|---|---|
| NEK1 | NEK1_HUMAN (Q96PY6) | NEK1_MOUSE (P51954) |
| NEK10 | NEK10_HUMAN (Q6ZWH5) | NEK10_MOUSE (Q3UGM2) |
| NEK11 | NEK11_HUMAN (Q8NG66) | NEK11_MOUSE (Q8C0Q4) |
| NEK2 | NEK2_HUMAN (P51955) | NEK2_MOUSE (O35942) |
| NEK3 | NEK3_HUMAN (P51956) | NEK3_MOUSE (Q9R0A5) |
| NEK4 | NEK4_HUMAN (P51957) | NEK4_MOUSE (Q9Z1J2) |
| NEK5 | NEK5_HUMAN (Q6P3R8) | NEK5_MOUSE (Q7TSC3) |
| NEK6 | NEK6_HUMAN (Q9HC98) | NEK6_MOUSE (Q9ES70) |
| NEK7 | NEK7_HUMAN (Q8TDX7) | NEK7_MOUSE (Q9ES74) |
| NEK8 | NEK8_HUMAN (Q86SG6) | NEK8_MOUSE (Q91ZR4) |
| NEK9 | NEK9_HUMAN (Q8TD19) | NEK9_MOUSE (Q8K1R7) |

TABLE 1F

STE Ser/Thr protein kinase family

| | | |
|---|---|---|
| MAP2K1 | MP2K1_HUMAN (Q02750) | MP2K1_MOUSE (P31938) |
| MAP2K2 | MP2K2_HUMAN (P36507) | MP2K2_MOUSE (Q63932) |
| MAP2K3 | MP2K3_HUMAN (P46734) | MP2K3_MOUSE (O09110) |
| MAP2K4 | MP2K4_HUMAN (P45985) | MP2K4_MOUSE (P47809) |
| MAP2K5 | MP2K5_HUMAN (Q13163) | MP2K5_MOUSE (Q9WVS7) |

TABLE 1F-continued

STE Ser/Thr protein kinase family

| | | |
|---|---|---|
| MAP2K6 | MP2K6_HUMAN (P52564) | MP2K6_MOUSE (P70236) |
| MAP2K7 | MP2K7_HUMAN (O14733) | MP2K7_MOUSE (Q8CE90) |
| MAP3K1 | M3K1_HUMAN (Q13233) | M3K1_MOUSE (P53349) |
| MAP3K10 | M3K10_HUMAN (Q02779) | M3K10_MOUSE (Q66L42) |
| MAP3K11 | M3K11_HUMAN (Q16584) | M3K11_MOUSE (Q80XI6) |
| MAP3K12 | M3K12_HUMAN (Q12852) | M3K12_MOUSE (Q60700) |
| MAP3K13 | M3K13_HUMAN (O43283) | M3K13_MOUSE (Q1HKZ5) |
| MAP3K14 | M3K14_HUMAN (Q99558) | M3K14_MOUSE (Q9WUL6) |
| MAP3K15 | M3K15_HUMAN (Q6ZN16) | M3K15_MOUSE (A2AQW0) |
| MAP3K19 | M3K19_HUMAN (Q56UN5) | M3K19_MOUSE (E9Q354) |
| MAP3K2 | M3K2_HUMAN (Q9Y2U5) | M3K2_MOUSE (Q61083) |
| MAP3K20 | M3K20_HUMAN (Q9NYL2) | M3K20_MOUSE (Q9ESL4) |
| MAP3K21 | M3K21_HUMAN (Q5TCX8) | M3K21_MOUSE (Q8VDG6) |
| MAP3K3 | M3K3_HUMAN (Q99759) | M3K3_MOUSE (Q61084) |
| MAP3K4 | M3K4_HUMAN (Q9Y6R4) | M3K4_MOUSE (O08648) |
| MAP3K5 | M3K5_HUMAN (Q99683) | M3K5_MOUSE (O35099) |
| MAP3K6 | M3K6_HUMAN (O95382) | M3K6_MOUSE (Q9WTR2) |
| MAP3K7 | M3K7_HUMAN (O43318) | M3K7_MOUSE (Q62073) |
| MAP3K8 | M3K8_HUMAN (P41279) | M3K8_MOUSE (Q07174) |
| MAP3K9 | M3K9_HUMAN (P80192) | M3K9_MOUSE (Q3U1V8) |
| MAP4K1 | M4K1_HUMAN (Q92918) | M4K1_MOUSE (P70218) |
| MAP4K2 | M4K2_HUMAN (Q12851) | M4K2_MOUSE (Q61161) |
| MAP4K3 | M4K3_HUMAN (Q8IVH8) | M4K3_MOUSE (Q99JP0) |
| MAP4K4 | M4K4_HUMAN (O95819) | M4K4_MOUSE (P97820) |
| MAP4K5 | M4K5_HUMAN (Q9Y4K4) | M4K5_MOUSE (Q8BPM2) |
| MINK1 | MINK1_HUMAN (Q8N4C8) | MINK1_MOUSE (Q9JM52) |
| MYO3A | MY03A_HUMAN (Q8NEV4) | MY03A_MOUSE (Q8K3H5) |
| MYO3B | MY03B_HUMAN (Q8WXR4) | MY03B_MOUSE (Q1EG27) |
| NRK | NRK_HUMAN (Q7Z2Y5) | NRK_MOUSE (Q9R0G8) |
| OXSR1 | OXSR1_HUMAN (O95747) | OXSR1_MOUSE (Q6P9R2) |
| PAK1 | PAK1_HUMAN (Q13153) | PAK1_MOUSE (O88643) |
| PAK2 | PAK2_HUMAN (Q13177) | PAK2_MOUSE (Q8CIN4) |
| PAK3 | PAK3_HUMAN (O75914) | PAK3_MOUSE (Q61036) |
| PAK4 | PAK4_HUMAN (O96013) | PAK4_MOUSE (Q8BTW9) |
| PAK5 | PAK5_HUMAN (Q9P286) | PAK5_MOUSE (Q8C015) |
| PAK6 | PAK6_HUMAN (Q9NQU5) | PAK6_MOUSE (Q3ULB5) |
| PBK | TOPK_HUMAN (Q96KB5) | TOPK_MOUSE (Q9JJ78) |
| SLK | SLK_HUMAN (Q9H2G2) | SLK_MOUSE (O54988) |
| STK10 | STK10_HUMAN (O94804) | STK10_MOUSE (O55098) |
| STK24 | STK24_HUMAN (Q9Y6E0) | STK24_MOUSE (Q99KH8) |
| STK25 | STK25_HUMAN (O00506) | STK25_MOUSE (Q9Z2W1) |
| STK26 | STK26_HUMAN (Q9P289) | STK26_MOUSE (Q99JT2) |
| STK3 | STK3_HUMAN (Q13188) | STK3_MOUSE (Q9JI10) |
| STK39 | STK39_HUMAN (Q9UEW8) | STK39_MOUSE (Q9Z1W9) |
| STK4 | STK4_HUMAN (Q13043) | STK4_MOUSE (Q9JI11) |
| STRADA | STRAA_HUMAN (Q7RTN6) | STRAA_MOUSE (Q3UUJ4) |
| STRADB | STRAB_HUMAN (Q9C0K7) | STRAB_MOUSE (Q8K4T3) |
| TAOK1 | TAOK1_HUMAN (Q7L7X3) | TAOK1_MOUSE (Q5F2E8) |
| TAOK2 | TAOK2_HUMAN (Q9UL54) | TAOK2_MOUSE (Q6ZQ29) |
| TAOK3 | TAOK3_HUMAN (Q9H2K8) | TAOK3_MOUSE (Q8BYC6) |
| TNIK | TNIK_HUMAN (Q9UKE5) | TNIK_MOUSE (P83510) |

TABLE 1G

TKL Ser/Thr protein kinase family

| | | |
|---|---|---|
| ACVR1 | ACVR1_HUMAN (Q04771) | ACVR1_MOUSE (P37172) |
| ACVR1B | ACV1B_HUMAN (P36896) | ACV1B_MOUSE (Q61271) |
| ACVR1C | ACV1C_HUMAN (Q8NER5) | ACV1C_MOUSE (Q8K348) |
| ACVR2A | AVR2A_HUMAN (P27037) | AVR2A_MOUSE (P27038) |
| ACVR2B | AVR2B_HUMAN (Q13705) | AVR2B_MOUSE (P27040) |
| ACVRL1 | ACVL1_HUMAN (P37023) | ACVL1_MOUSE (Q61288) |
| AMHR2 | AMHR2_HUMAN (Q16671) | AMHR2_MOUSE (Q8K592) |
| ANKK1 | ANKK1_HUMAN (Q8NFD2) | ANKK1_MOUSE (Q8BZ25) |
| ARAF | ARAF_HUMAN (P10398) | ARAF_MOUSE (P04627) |
| BMPR1A | BMR1A_HUMAN (P36894) | BMR1A_MOUSE (P36895) |
| BMPR1B | BMR1B_HUMAN (O00238) | BMR1B_MOUSE (P36898) |
| BMPR2 | BMPR2_HUMAN (Q13873) | BMPR2_MOUSE (O35607) |
| BRAF | BRAF_HUMAN (P15056) | BRAF_MOUSE (P28028) |
| ILK | ILK_HUMAN (Q13418) | ILK_MOUSE (O55222) |
| IRAK1 | IRAK1_HUMAN (P51617) | IRAK1_MOUSE (Q62406) |
| IRAK2 | IRAK2_HUMAN (O43187) | IRAK2_MOUSE (Q8CFA1) |
| IRAK3 | IRAK3_HUMAN (Q9Y616) | IRAK3_MOUSE (Q8K4B2) |
| IRAK4 | IRAK4_HUMAN (Q9NWZ3) | IRAK4_MOUSE (Q8R4K2) |
| KSR1 | KSR1_HUMAN (Q8IVT5) | KSR1_MOUSE (Q61097) |

TABLE 1G-continued

TKL Ser/Thr protein kinase family

| | | |
|---|---|---|
| KSR2 | KSR2_HUMAN (Q6VAB6) | KSR2_MOUSE (Q3UVC0) |
| LIMK1 | LIMK1_HUMAN (P53667) | LIMK1_MOUSE (P53668) |
| LIMK2 | LIMK2_HUMAN (P53671) | LIMK2_MOUSE (O54785) |
| LRRK1 | LRRK1_HUMAN (Q38SD2) | LRRK1_MOUSE (Q3UHC2) |
| LRRK2 | LRRK2_HUMAN (Q5S007) | LRRK2_MOUSE (Q5S006) |
| RAF1 | RAF1_HUMAN (P04049) | RAF1_MOUSE (Q99N57) |
| RIPK1 | RIPK1_HUMAN (Q13546) | RIPK1_MOUSE (Q60855) |
| RIPK2 | RIPK2_HUMAN (O43353) | RIPK2_MOUSE (P58801) |
| RIPK3 | RIPK3_HUMAN (Q9Y572) | RIPK3_MOUSE (Q9QZL0) |
| RIPK4 | RIPK4_HUMAN (P57078) | RIPK4_MOUSE (Q9ERK0) |
| TESK1 | TESK1_HUMAN (Q15569) | TESK1_MOUSE (O70146) |
| TESK2 | TESK2_HUMAN (Q96S53) | TESK2_MOUSE (Q8VCT9) |
| TGFBR1 | TGFR1_HUMAN (P36897) | TGFR1_MOUSE (Q64729) |
| TGFBR2 | TGFR2_HUMAN (P37173) | TGFR2_MOUSE (Q62312) |
| TNNI3K | TNI3K_HUMAN (Q59H18) | TNI3K_MOUSE (Q5GIG6) |

TABLE 1H

Tyr protein kinase family

| | | |
|---|---|---|
| AATK | LMTK1_HUMAN (Q6ZMQ8) | LMTK1_MOUSE (Q80YE4) |
| ABL1 | ABL1_HUMAN (P00519) | ABL1_MOUSE (P00520) |
| ABL2 | ABL2_HUMAN (P42684) | ABL2_MOUSE (Q4JIM5) |
| ALK | ALK_HUMAN (Q9UM73) | ALK_MOUSE (P97793) |
| AXL | UFO_HUMAN (P30530) | UFO_MOUSE (Q00993) |
| BLK | BLK_HUMAN (P51451) | BLK_MOUSE (P16277) |
| BMX | BMX_HUMAN (P51813) | BMX_MOUSE (P97504) |
| BTK | BTK_HUMAN (Q06187) | BTK_MOUSE (P35991) |
| CSF1R | CSF1R_HUMAN (P07333) | CSF1R_MOUSE (P09581) |
| CSK | CSK_HUMAN (P41240) | CSK_MOUSE (P41241) |
| DDR1 | DDR1_HUMAN (Q08345) | DDR1_MOUSE (Q03146) |
| DDR2 | DDR2_HUMAN (Q16832) | DDR2_MOUSE (Q62371) |
| EGFR | EGFR_HUMAN (P00533) | EGFR_MOUSE (Q01279) |
| EPHA1 | EPHA1_HUMAN (P21709) | EPHA1_MOUSE (Q60750) |
| EPHA10 | EPHAA_HUMAN (Q5JZY3) | EPHAA_MOUSE (Q8BYG9) |
| EPHA2 | EPHA2_HUMAN (P29317) | EPHA2_MOUSE (Q03145) |
| EPHA3 | EPHA3_HUMAN (P29320) | EPHA3_MOUSE (P29319) |
| EPHA4 | EPHA4_HUMAN (P54764) | EPHA4_MOUSE (Q03137) |
| EPHA5 | EPHA5_HUMAN (P54756) | EPHA5_MOUSE (Q60629) |
| EPHA6 | EPHA6_HUMAN (Q9UF33) | EPHA6_MOUSE (Q62413) |
| EPHA7 | EPHA7_HUMAN (Q15375) | EPHA7_MOUSE (Q61772) |
| EPHA8 | EPHA8_HUMAN (P29322) | EPHA8_MOUSE (O09127) |
| EPHB1 | EPHB1_HUMAN (P54762) | EPHB1_MOUSE (Q8CBF3) |
| EPHB2 | EPHB2_HUMAN (P29323) | EPHB2_MOUSE (P54763) |
| EPHB3 | EPHB3_HUMAN (P54753) | EPHB3_MOUSE (P54754) |
| EPHB4 | EPHB4_HUMAN (P54760) | EPHB4_MOUSE (P54761) |
| EPHB6 | EPHB6_HUMAN (O15197) | EPHB6_MOUSE (O08644) |
| ERBB2 | ERBB2_HUMAN (P04626) | ERBB2_MOUSE (P70424) |
| ERBB3 | ERBB3_HUMAN (P21860) | ERBB3_MOUSE (Q61526) |
| ERBB4 | ERBB4_HUMAN (Q15303) | ERBB4_MOUSE (Q61527) |
| FER | FER_HUMAN (P16591) | FER_MOUSE (P70451) |
| FES | FES_HUMAN (P07332) | FES_MOUSE (P16879) |
| FGFR1 | FGFR1_HUMAN (P11362) | FGFR1_MOUSE (P16092) |
| FGFR2 | FGFR2_HUMAN (P21802) | FGFR2_MOUSE (P21803) |
| FGFR3 | FGFR3_HUMAN (P22607) | FGFR3_MOUSE (Q61851) |
| FGFR4 | FGFR4_HUMAN (P22455) | FGFR4_MOUSE (Q03142) |
| FGR | FGR_HUMAN (P09769) | FGR_MOUSE (P14234) |
| FLT1 | VGFR1_HUMAN (P17948) | VGFR1_MOUSE (P35969) |
| FLT3 | FLT3_HUMAN (P36888) | FLT3_MOUSE (Q00342) |
| FLT4 | VGFR3_HUMAN (P35916) | VGFR3_MOUSE (P35917) |
| FRK | FRK_HUMAN (P42685) | FRK_MOUSE (Q922K9) |
| FYN | FYN_HUMAN (P06241) | FYN_MOUSE (P39688) |
| HCK | HCK_HUMAN (P08631) | HCK_MOUSE (P08103) |
| IGF1R | IGF1R_HUMAN (P08069) | IGF1R_MOUSE (Q60751) |
| INSR | INSR_HUMAN (P06213) | INSR_MOUSE (P15208) |
| INSRR | INSRR_HUMAN (P14616) | INSRR_MOUSE (Q9WTL4) |
| ITK | ITK_HUMAN (Q08881) | ITK_MOUSE (Q03526) |
| JAK1 | JAK1_HUMAN (P23458) | JAK1_MOUSE (P52332) |
| JAK2 | JAK2_HUMAN (O60674) | JAK2_MOUSE (Q62120) |
| JAK3 | JAK3_HUMAN (P52333) | JAK3_MOUSE (Q62137) |
| KDR | VGFR2_HUMAN (P35968) | VGFR2_MOUSE (P35918) |
| KIT | KIT_HUMAN (P10721) | KIT_MOUSE (P05532) |
| LCK | LCK_HUMAN (P06239) | LCK_MOUSE (P06240) |
| LMTK2 | LMTK2_HUMAN (Q8IWU2) | LMTK2_MOUSE (Q3TYD6) |
| LMTK3 | LMTK3_HUMAN (Q96Q04) | LMTK3_MOUSE (Q5XJV6) |

TABLE 1H-continued

Tyr protein kinase family

| | | |
|---|---|---|
| LTK | LTK_HUMAN (P29376) | LTK_MOUSE (P08923) |
| LYN | LYN_HUMAN (P07948) | LYN_MOUSE (P25911) |
| MATK | MATK_HUMAN (P42679) | MATK_MOUSE (P41242) |
| MERTK | MERTK_HUMAN (Q12866) | MERTK_MOUSE (Q60805) |
| MET | MET_HUMAN (P08581) | MET_MOUSE (P16056) |
| MST1R | RON_HUMAN (Q04912) | RON_MOUSE (Q62190) |
| MUSK | MUSK_HUMAN (O15146) | MUSK_MOUSE (Q61006) |
| NTRK1 | NTRK1_HUMAN (P04629) | NTRK1_MOUSE (Q3UFB7) |
| NTRK2 | NTRK2_HUMAN (Q16620) | NTRK2_MOUSE (P15209) |
| NTRK3 | NTRK3_HUMAN (Q16288) | NTRK3_MOUSE (Q6VNS1) |
| PDGFRA | PGFRA_HUMAN (P16234) | PGFRA_MOUSE (P26618) |
| PDGFRB | PGFRB_HUMAN (P09619) | PGFRB_MOUSE (P05622) |
| PTK2 | FAK1_HUMAN (Q05397) | FAK1_MOUSE (P34152) |
| PTK2B | FAK2_HUMAN (Q14289) | FAK2_MOUSE (Q9QVP9) |
| PTK6 | PTK6_HUMAN (Q13882) | PTK6_MOUSE (Q64434) |
| PTK7 | PTK7_HUMAN (Q13308) | PTK7_MOUSE (Q8BKG3) |
| RET | RET_HUMAN (P07949) | RET_MOUSE (P35546) |
| ROR1 | ROR1_HUMAN (Q01973) | ROR1_MOUSE (Q9Z139) |
| ROR2 | ROR2_HUMAN (Q01974) | ROR2_MOUSE (Q9Z138) |
| ROS1 | RO51_HUMAN (P08922) | ROS1_MOUSE (Q78DX7) |
| RYK | RYK_HUMAN (P34925) | RYK_MOUSE (Q01887) |
| SRC | SRC_HUMAN (P12931) | SRC_MOUSE (P05480) |
| SRMS | SRMS_HUMAN (Q9H3Y6) | SRMS_MOUSE (Q62270) |
| STYK1 | STYK1_HUMAN (Q6J9G0) | STYK1_MOUSE (Q6J9G1) |
| SYK | KSYK_HUMAN (P43405) | KSYK_MOUSE (P48025) |
| Smok1 | | SMOK1_MOUSE (Q9QYZ4) |
| Smoktcr | | SMKTR_MOUSE (A2KF29) |
| TEC | TEC_HUMAN (P42680) | TEC_MOUSE (P24604) |
| TEK | TIE2_HUMAN (Q02763) | TIE2_MOUSE (Q02858) |
| TIE1 | TIE1_HUMAN (P35590) | TIE1_MOUSE (Q06806) |
| TNK1 | TNK1_HUMAN (Q13470) | TNK1_MOUSE (Q99ML2) |
| TNK2 | ACK1_HUMAN (Q07912) | ACK1_MOUSE (O54967) |
| TXK | TXK_HUMAN (P42681) | TXK_MOUSE (P42682) |
| TYK2 | TYK2_HUMAN (P29597) | TYK2_MOUSE (Q9R117) |
| TYRO3 | TYRO3_HUMAN (Q06418) | TYRO3_MOUSE (P55144) |
| YES1 | YES_HUMAN (P07947) | YES_MOUSE (Q04736) |
| ZAP70 | ZAP70_HUMAN (P43403) | ZAP70_MOUSE (P43404) |

TABLE 1I

Other kinases.

| | | |
|---|---|---|
| AAK1 | AAK1_HUMAN (Q2M2I8) | AAK1_MOUSE (Q3UHJ0) |
| AURKA | AURKA_HUMAN (O14965) | AURKA_MOUSE (P97477) |
| AURKB | AURKB_HUMAN (Q96GD4) | AURKB_MOUSE (O70126) |
| AURKC | AURKC_HUMAN (Q9UQB9) | AURKC_MOUSE (O88445) |
| BMP2K | BMP2K_HUMAN (Q9NSY1) | BMP2K_MOUSE (Q91Z96) |
| BUB1 | BUB1_HUMAN (O43683) | BUB1_MOUSE (O08901) |
| BUB1B | BUB1B_HUMAN (O60566) | BUB1B_MOUSE (Q9Z1S0) |
| CAMKK1 | KKCC1_HUMAN (Q8N5S9) | KKCC1_MOUSE (Q8VBY2) |
| CAMKK2 | KKCC2_HUMAN (Q96RR4) | KKCC2_MOUSE (Q8C078) |
| CDC7 | CDC7_HUMAN (O00311) | CDC7_MOUSE (Q9Z0H0) |
| CHUK | IKKA_HUMAN (O15111) | IKKA_MOUSE (Q60680) |
| CSNK2A1 | CSK21_HUMAN (P68400) | CSK21_MOUSE (Q60737) |
| CSNK2A2 | CSK22_HUMAN (P19784) | CSK22_MOUSE (O54833) |
| CSNK2A3 | CSK23_HUMAN (Q8NEV1) | |
| DSTYK | DUSTY_HUMAN (Q6XUX3) | DUSTY_MOUSE (Q6XUX1) |
| EIF2AK1 | E2AK1_HUMAN (Q9BQI3) | E2AK1_MOUSE (Q9Z2R9) |
| EIF2AK2 | E2AK2_HUMAN (P19525) | E2AK2_MOUSE (Q03963) |
| EIF2AK3 | E2AK3_HUMAN (Q9NZJ5) | E2AK3_MOUSE (Q9Z2B5) |
| EIF2AK4 | E2AK4_HUMAN (Q9P2K8) | E2AK4_MOUSE (Q9QZ05) |
| ERN1 | ERN1_HUMAN (O75460) | ERN1_MOUSE (Q9EQY0) |
| ERN2 | ERN2_HUMAN (Q76MJ5) | ERN2_MOUSE (Q9Z2E3) |
| GAK | GAK_HUMAN (O14976) | GAK_MOUSE (Q99KY4) |
| HASPIN | HASP_HUMAN (Q8TF76) | HASP_MOUSE (Q9Z0R0) |
| IKBKB | IKKB_HUMAN (O14920) | IKKB_MOUSE (O88351) |
| IKBKE | IKKE_HUMAN (Q14164) | IKKE_MOUSE (Q9ROT8) |
| MLKL | MLKL_HUMAN (Q8NB16) | MLKL_MOUSE (Q9D2Y4) |
| MOS | MOS_HUMAN (P00540) | MOS_MOUSE (P00536) |
| NRBP1 | NRBP_HUMAN (Q9UHY1) | NRBP_MOUSE (Q99J45) |
| NRBP2 | NRBP2_HUMAN (Q9NSY0) | NRBP2_MOUSE (Q91V36) |
| PAN3 | PAN3_HUMAN (Q58A45) | PAN3_MOUSE (Q640Q5) |
| PDIK1L | PDK1L_HUMAN (Q8N165) | PDK1L_MOUSE (Q8QZR7) |
| PEAK1 | PEAK1_HUMAN (Q9H792) | PEAK1_MOUSE (Q69Z38) |
| PIK3R4 | PI3R4_HUMAN (Q99570) | PI3R4_MOUSE (Q8VD65) |

TABLE 1I-continued

Other kinases.

| | | |
|---|---|---|
| PINK1 | PINK1_HUMAN (Q9BXM7) | PINK1_MOUSE (Q99MQ3) |
| PKDCC | PKDCC_HUMAN (Q504Y2) | PKDCC_MOUSE (Q5RJI4) |
| PKMYT1 | PMYT1_HUMAN (Q99640) | PMYT1_MOUSE (Q9ESG9) |
| PLK1 | PLK1_HUMAN (P53350) | PLK1_MOUSE (Q07832) |
| PLK2 | PLK2_HUMAN (Q9NYY3) | PLK2_MOUSE (P53351) |
| PLK3 | PLK3_HUMAN (Q9H4B4) | PLK3_MOUSE (Q60806) |
| PLK4 | PLK4_HUMAN (O00444) | PLK4_MOUSE (Q64702) |
| PLK5 | PLK5_HUMAN (Q496M5) | PLK5_MOUSE (Q4FZD7) |
| POMK | SG196_HUMAN (Q9H5K3) | SG196_MOUSE (Q3TUA9) |
| PRAG1 | PRAG1_HUMAN (Q86YV5) | PRAG1_MOUSE (Q571I4) |
| PXK | PXK_HUMAN (Q7Z7A4) | PXK_MOUSE (Q8BX57) |
| RNASEL | RN5A_HUMAN (Q05823) | RN5A_MOUSE (Q05921) |
| RPS6KC1 | KS6C1_HUMAN (Q96S38) | KS6C1_MOUSE (Q8BLK9) |
| RPS6KL1 | RPKL1_HUMAN (Q9Y6S9) | RPKL1_MOUSE (Q8R2S1) |
| SBK1 | SBK1_HUMAN (Q52WX2) | SBK1_MOUSE (Q8QZX0) |
| SBK2 | SBK2_HUMAN (P0C263) | SBK2_MOUSE (P0C5K1) |
| SBK3 | SBK3_HUMAN (P0C264) | SBK3_MOUSE (P0C5K0) |
| SCYL1 | SCYL1_HUMAN (Q96KG9) | SCYL1_MOUSE (Q9EQC5) |
| SCYL2 | SCYL2_HUMAN (Q6P3W7) | SCYL2_MOUSE (Q8CFE4) |
| SCYL3 | PACE1_HUMAN (Q8IZE3) | PACE1_MOUSE (Q9DBQ7) |
| SGK494 | SG494_HUMAN (Q96LW2) | SG494_MOUSE (Q5SYL1) |
| STK16 | STK16_HUMAN (O75716) | STK16_MOUSE (O88697) |
| STK31 | STK31_HUMAN (Q9BXU1) | STK31_MOUSE (Q99MW1) |
| STK32A | ST32A_HUMAN (Q8WU08) | ST32A_MOUSE (Q8BGW6) |
| STK32B | ST32B_HUMAN (Q9NY57) | ST32B_MOUSE (Q9JJX8) |
| STK32C | ST32C_HUMAN (Q86UX6) | ST32C_MOUSE (Q8QZV4) |
| STK35 | STK35_HUMAN (Q8TDR2) | STK35_MOUSE (Q80ZW0) |
| STK36 | STK36_HUMAN (Q9NRP7) | STK36_MOUSE (Q69ZM6) |
| STKLD1 | STKL1_HUMAN (Q8NE28) | STKL1_MOUSE (Q80YS9) |
| TBCK | TBCK_HUMAN (Q8TEA7) | TBCK_MOUSE (Q8BM85) |
| TBK1 | TBK1_HUMAN (Q9UHD2) | TBK1_MOUSE (Q9WUN2) |
| TEX14 | TEX14_HUMAN (Q8IWB6) | TEX14_MOUSE (Q7M6U3) |
| TLK1 | TLK1_HUMAN (Q9UKI8) | TLK1_MOUSE (Q8C0V0) |
| TLK2 | TLK2_HUMAN (Q86UE8) | TLK2_MOUSE (O55047) |
| TP53RK | PRPK_HUMAN (Q96S44) | PRPK_MOUSE (Q99PW4) |
| TTK | TTK_HUMAN (P33981) | TTK_MOUSE (P35761) |
| UHMK1 | UHMK1_HUMAN (Q8TAS1) | UHMK1_MOUSE (P97343) |
| ULK1 | ULK1_HUMAN (O75385) | ULK1_MOUSE (O70405) |
| ULK2 | ULK2_HUMAN (Q8IYT8) | ULK2_MOUSE (Q9QY01) |
| ULK3 | ULK3_HUMAN (Q6PHR2) | ULK3_MOUSE (Q3U3Q1) |
| ULK4 | ULK4_HUMAN (Q96C45) | ULK4_MOUSE (Q3V129) |
| WEE1 | WEE1_HUMAN (P30291) | WEE1_MOUSE (P47810) |
| WEE2 | WEE2_HUMAN (P0C1S8) | WEE2_MOUSE (Q66JT0) |
| WNK1 | WNK1_HUMAN (Q9H4A3) | WNK1_MOUSE (P83741) |
| WNK2 | WNK2_HUMAN (Q9Y3S1) | WNK2_MOUSE (Q3UH66) |
| WNK3 | WNK3_HUMAN (Q9BYP7) | WNK3_MOUSE (Q80XP9) |
| WNK4 | WNK4_HUMAN (Q96J92) | WNK4_MOUSE (Q80UE6) |

TABLE 1J

ADCK protein kinase family

| | | |
|---|---|---|
| ADCK1 | ADCK1_HUMAN (Q86TW2) | ADCK1_MOUSE (Q9D0L4) |
| ADCK2 | ADCK2_HUMAN (Q7Z695) | ADCK2_MOUSE (Q6NSR3) |
| ADCK5 | ADCK5_HUMAN (Q3MIX3) | ADCK5_MOUSE (Q80V03) |
| COQ8A | COQ8A_HUMAN (Q8NI60) | COQ8A_MOUSE (Q60936) |
| COQ8B | COQ8B_HUMAN (Q96D53) | COQ8B_MOUSE (Q566J8) |

TABLE 1K

Alpha-type protein kinase family

| | | |
|---|---|---|
| ALPK1 | ALPK1_HUMAN (Q96QP1) | ALPK1_MOUSE (Q9CXB8) |
| ALPK2 | ALPK2_HUMAN (Q86TB3) | ALPK2_MOUSE (Q91ZB0) |
| ALPK3 | ALPK3_HUMAN (Q96L96) | ALPK3_MOUSE (Q924C5) |
| EEF2K | EF2K_HUMAN (O00418) | EF2K_MOUSE (O08796) |
| TRPM6 | TRPM6_HUMAN (Q9BX84) | TRPM6_MOUSE (Q8CIR4) |
| TRPM7 | TRPM7_HUMAN (Q96QT4) | TRPM7_MOUSE (Q923J1) |

TABLE 1L

FAST protein kinase family

| | | |
|---|---|---|
| FASTK | FASTK_HUMAN (Q14296) | FASTK_MOUSE (Q9JIX9) |

TABLE 1M

PDK/BCKDK protein kinase family

| | | |
|---|---|---|
| BCKDK | BCKD_HUMAN (O14874) | BCKD_MOUSE (O55028) |
| PDK1 | PDK1_HUMAN (Q15118) | PDK1_MOUSE (Q8BFP9) |
| PDK2 | PDK2_HUMAN (Q15119) | PDK2_MOUSE (Q9JK42) |
| PDK3 | PDK3_HUMAN (Q15120) | PDK3_MOUSE (Q922H2) |
| PDK4 | PDK4_HUMAN (Q16654) | PDK4_MOUSE (O70571) |

TABLE 1N

PI3/PI4-kinase family

| | | |
|---|---|---|
| ATM | ATM_HUMAN (Q13315) | ATM_MOUSE (Q62388) |
| ATR | ATR_HUMAN (Q13535) | ATR_MOUSE (Q9JKK8) |
| MTOR | MTOR_HUMAN (P42345) | MTOR_MOUSE (Q9JLN9) |
| PIK3CA | PK3CA_HUMAN (P42336) | PK3CA_MOUSE (P42337) |
| PIK3CG | PK3CG_HUMAN (P48736) | PK3CG_MOUSE (Q9JHG7) |

TABLE 1N-continued

PI3/PI4-kinase family

| | | |
|---|---|---|
| PRKDC | PRKDC_HUMAN (P78527) | PRKDC_MOUSE (P97313) |
| SMG1 | SMG1_HUMAN (Q96Q15) | SMG1_MOUSE (Q8BKX6) |

TABLE 1O

RIO-type Ser/Thr kinase family

| | | |
|---|---|---|
| RIOK1 | RIOK1_HUMAN (Q9BRS2) | RIOK1_MOUSE (Q922Q2) |
| RIOK2 | RIOK2_HUMAN (Q9BVS4) | RIOK2_MOUSE (Q9CQS5) |
| RIOK3 | RIOK3_HUMAN (O14730) | RIOK3_MOUSE (Q9DBU3) |

EXPERIMENTAL

All starting materials and reagents were purchased from commercial sources and used as received unless indicated otherwise. Abbreviations used in the examples that follow include the following: Boc is tert-butyloxycarbonyl; DCM is dichloromethane; DMF is N,N-dimethylformamide; ESI is electrospray ionization; HATU is 1-[bis(dimethylamino)methylene]-1H-1,2,3-triazolo[4,5-b]pyridinium 3-oxid hexafluorophosphate; HPLC is high-performance liquid chromatography; MS is mass spectrometry; RT is room temperature; and TFA is trifluoroacetic acid.

Example 1

Tert-butyl (15-(4-(4-(((5-chloro-4-(((2-(methylcarbamoyl)phenyl)amino)pyrimidin-2-yl)amino)phenyl)piperazin-1-yl)-15-oxo-3,6,9,12-tetraoxapentadecyl) carbamate Compound CC-1290

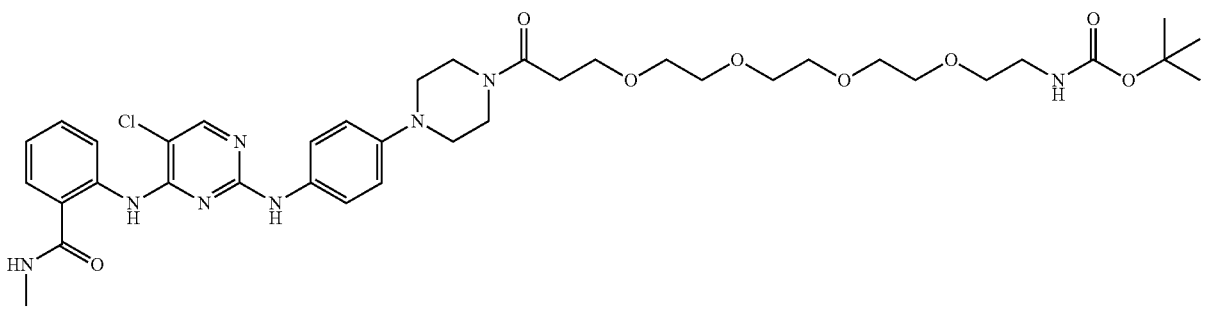 [SMILES: CNC(=O)c1ccccc1Nc1nc(Nc2ccc(N3CCN(C(=O)CCOCCOCCOCCOCCNC(=O)OC(C)(C)C)CC3)cc2)ncc1Cl]

2-((5-chloro-2-((4-(piperazin-1-yl)phenyl)amino)pyrimidin-4-yl)amino)-N-methylbenzamide (200.0 mg, 0.46 mmol) and 2,2-dimethyl-4-oxo-3,8,11,14,17-pentaoxa-5-azaicosan-20-oic acid (250.0 mg, 0.69 mmol) and HATU (208.4 mg, 0.55 mmol) were taken up in DMF (5 mL), and N,N-diisopropylethylamine (238.7 µL, 1.37 mmol) was added. The mixture was stirred for 3 hrs, and volatiles removed under reduced pressure. The crude was taken up in a minimum volume of dichloromethane, absorbed on Celite, and dried to a free flowing solid. The mixture was subjected to silica gel flash chromatography giving the desired product (192.0 mg, 53.3%) as a white solid. MS (ESI+) m/z calc'd for [M+H]$^+$ $C_{38}H_{54}ClN_8O_8$: 785.38, found 785.60.

Example 2

Compound CC-1294

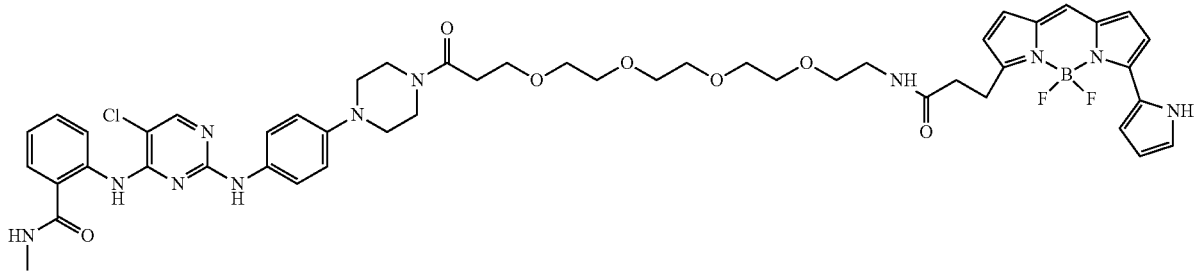

Tert-butyl (15-(4-(4-((5-chloro-4-((2-(methylcarbamoyl)phenyl)amino)pyrimidin-2-yl)amino)phenyl)piperazin-1-yl)-15-oxo-3,6,9,12-tetraoxapentadecyl)carbamate (125.0 mg, 0.16 mmol) in DCM (2.0 mL) was treated with 100 uL of triisopropylsilane followed by trifluoroacetic acid (2 mL). The mixture was capped, allowed to stir for 3 hrs, and volatiles removed under reduced pressure to give a yellow oil. The mixture was dried under high vacuum, and the residue treated with diethyl ether to give a yellow solid. The diethylether was decanted, and the residue dried under high vacuum for 30 min. The crude was taken up in anhydrous DMF (5 mL) with stirring and treated with N,N-diisopropylethylamine (277 μL, 1.59 mmol). The reaction was allowed to stir for 10 min, NanoBRET™ 590 SE tracer (Promega Corporation; 74.5 mg, 0.17 mmol) added, and the reaction stirred in the dark for 2 hrs. Volatiles were removed under reduced pressure giving a blue film that was purified by amine-modified silica gel flash chromatography to give the product (118.5 mg 74.8%) as a blue solid. MS (ESI+) m/z calc'd for $[M+H]^+$ $C_{49}H_{58}BClF_2N_{11}O_7$: 996.46, found 996.4.

Example 3

Tert-butyl (15-(4-(3-aminophenyl)piperazin-1-yl)-15-oxo-3,6,9,12 tetraoxapentadecyl)carbamate Compound CC-1815

2,5-dioxopyrrolidin-1-yl 2,2-dimethyl-4-oxo-3,8,11,14,17-pentaoxa-5-azaicosan-20-oate (525.0 mg, 1.14 mmol) and 3-(piperazin-1-yl)aniline (200.0 mg, 1.13 mmol) were dissolved in dichloromethane (10.0 mL) giving a yellow suspension. N,N-diisopropylethylamine (590 μL, 3.39 mmol) was added, and the mixture stirred for 2 hrs. The crude mixture was absorbed on Celite, volatiles removed under reduced pressure, and the crude subjected to silica gel flash chromatography giving the product (590.0 mg, 100%) as a yellow solid.

Example 4

2-((2-((3-(4-(1-amino-3,6,9,12-tetraoxapentadecan-15-oyl)piperazin-1-yl)phenyl)amino)-5-chloropyrimidin-4-yl)amino)benzamide Compound CC-1816

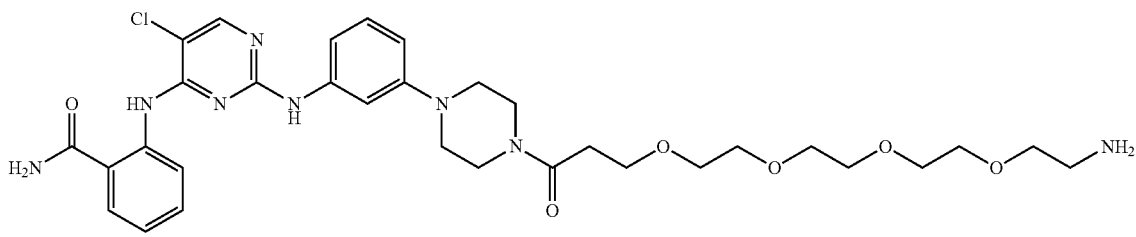 [SMILES: NCCOCCOCCOCCOCCC(=O)N1CCN(c2cccc(Nc3ncc(Cl)c(Nc4ccccc4C(N)=O)n3)c2)CC1]

2-((2,5-dichloropyrimidin-4-yl)amino)benzamide (294.3 mg, 1.04 mmol) and tert-butyl (15-(4-(3-aminophenyl)piperazin-1-yl)-15-oxo-3,6,9,12-tetraoxapentadecyl)carbamate (600.0 mg, 1.14 mmol) in 2-methoxyethanol (8 mL) were heated to 100° C. overnight. The mixture was cooled to RT, and volatiles removed under reduced pressure giving a red solid that was dried under high vacuum. The Boc-deprotected crude residue was dissolve in a minimum volume of dichloromethane, absorbed on Celite, dried to a free flowing solid, and purified by silica gel flash chromatography to give the desired product (270.0 mg, 33.7%) as a red-yellow solid. MS (ESI+) m/z calc'd for [M+H]$^+$ $C_{32}H_{44}ClN_8O_6$ 671.31 found 671.30.

Example 5

Compound CC-1817

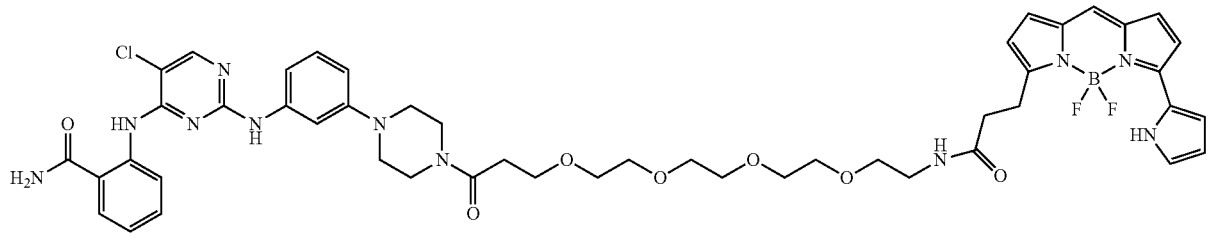

2-((2-((3-(4-(1-amino-3,6,9,12-tetraoxapentadecan-15-oyl)piperazin-1-yl)phenyl)amino)-5-chloropyrimidin-4-yl)amino)benzamide (250.0 mg, 0.037 mmol) was taken up in anhydrous DMF (5 mL) with stirring. To the mixture, N,N-diisopropylethylamine (22.2 µL, 0.03 mmol) was added, and the reaction allowed to stir for 10 min. NanoBRET™ 590 SE tracer (Promega Corp.; 17.5 mg, 0.038 mmol) was added, and the reaction stirred in the dark for 2 hrs. Volatiles were removed under reduced pressure giving a blue film that was taken up in 8 mL of 1:1:0.01 acetonitrile, water, trifluoroacetic acid and subjected to reverse phase preparative HPLC purification to give the product (12.0 mg 32.8%) as a blue solid. MS (ESI+) m/z calc'd for [M+H]$^+$ $C_{48}H_{56}BClF_2N_{11}O_7$: 982.41, found 982.67.

Example 6

Tert-butyl 4-(4-((4-((2-carbamoylphenyl)amino)-5-chloropyrimidin-2-yl)amino)phenyl)piperazine-1-carboxylate Compound CC-1790

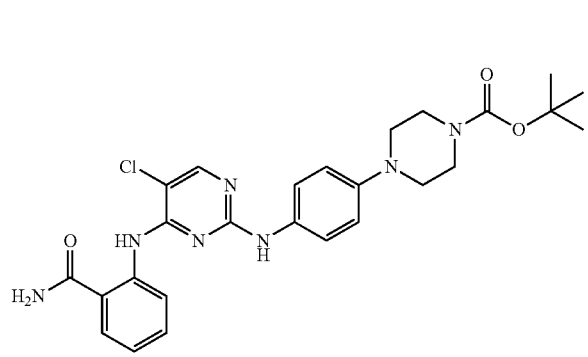 [SMILES: CC(C)(C)OC(=O)N1CCN(c2ccc(Nc3ncc(Cl)c(Nc4ccccc4C(N)=O)n3)cc2)CC1]

2-((2,5-dichloropyrimidin-4-yl)amino)benzamide (500 mg, 1.77 mmol) and tert-butyl 4-(4-aminophenyl)piperazine-1-carboxylate (583.8, 1.94 mmol) in 2-methoxyethanol (6 mL) were heated to 100° C. overnight. The mixture was cooled to RT, and volatiles removed under reduced pressure to give a brown solid that was dried under high vacuum. The crude residue was dissolved in a minimum volume of dichloromethane, absorbed on Celite, and dried to a free flowing solid. The mixture was purified by silica gel flash chromatography to give the desired product (200.0 mg, 21.6%) as a yellow solid. MS (ESI+) m/z calc'd for [M+H]+ $C_{26}H_{31}ClN_7O_3$: 524.22, found 524.19.

Example 7

2-((5-chloro-2-((4-(piperazin-1-yl)phenyl)amino)pyrimidin-4-yl)amino)benzamide-TFA Compound CC-1795

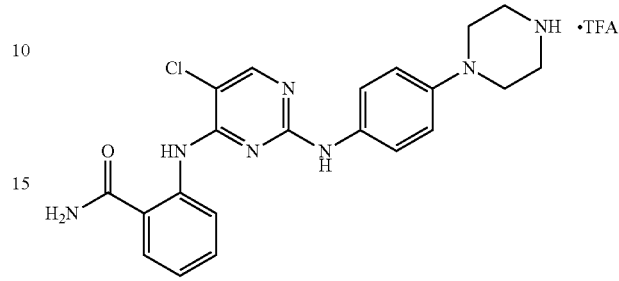

Tert-butyl 4-(4-((4-((2-carbamoylphenyl)amino)-5-chloropyrimidin-2-yl)amino)phenyl)piperazine-1-carboxylate (200.0 mg, 0.38 mmol) in DCM (3.0 mL) was treated with 300 μL of triisopropylsilane followed by trifluoroacetic acid (3 mL). The mixture was capped, allowed to stir for 4 hrs, and volatiles removed under reduced pressure to give a purple oil. The mixture was dried under high vacuum, and the residue treated with diethyl ether, giving a dark solid. Ether was decanted, and an additional portion of diethyl ether added and decanted before drying the residue under hi vacuum overnight. The resulting solid was dissolved in 1:1:0.01 acetonitrile, water, trifluoroacetic acid and subjected to reverse phase-preparative HPLC purification to give the desired product (136.0 mg, 84.1%) as a yellow solid.

Example 8 tert-butyl (15-(4-(4-((4-((2-carbamoylphenyl)amino)-5-chloropyrimidin-2-yl)amino)phenyl)piperazin-1-yl)-15-oxo-3,6,9,12-tetraoxapentadecyl)carbamate Compound CC-1796

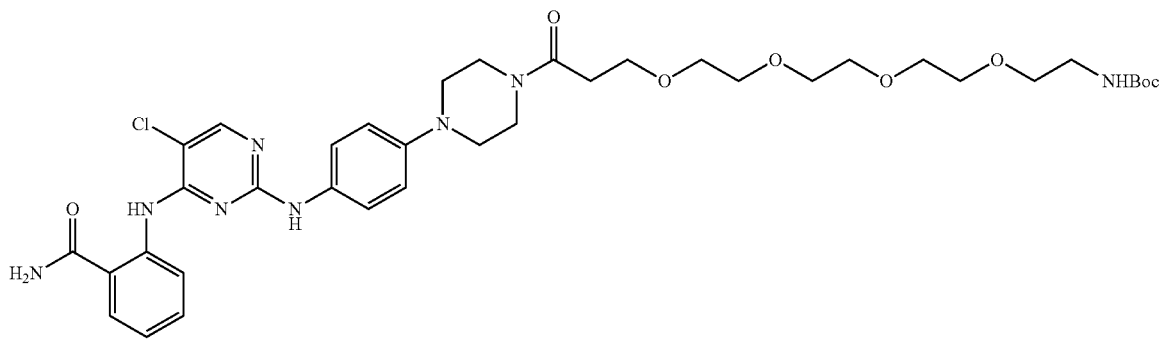 [SMILES: CC(C)(C)OC(=O)NCCOCCOCCOCCOCCC(=O)N1CCN(c2ccc(Nc3ncc(Cl)c(Nc4ccccc4C(N)=O)n3)cc2)CC1]

2-((5-chloro-2-((4-(piperazin-1-yl)phenyl)amino)pyrimidin-4-yl)amino)benzamide (100.0 mg, 0.24 mmol), 2,5-dioxopyrrolidin-1-yl 2,2-dimethyl-4-oxo-3,8,11,14,17-pentaoxa-5-azaicosan-20-oate (163.7 mg, 353.9 mmol) and N,N-diisopropylethylamine (127.3 μL, 0.71 mmol) in dichloromethane (10 mL) were stirred for 2 hrs. The crude was absorbed on Celite, dried to a free flowing solid, and the mixture subjected to silica gel flash chromatography to give the desired product (156.0 mg, 85.7%) as a yellow solid. MS (ESI+) m/z calc'd for [M+H]+ $C_{37}H_{52}ClN_8O_8$: 771.38, found 771.35.

Example 9

2-((2-((4-(4-(1-amino-3,6,9,12-tetraoxapentadecan-15-oyl)piperazin-1-yl)phenyl)amino)-5-chloropyrimidin-4-yl)amino)benzamide-TFA Compound CC-1803

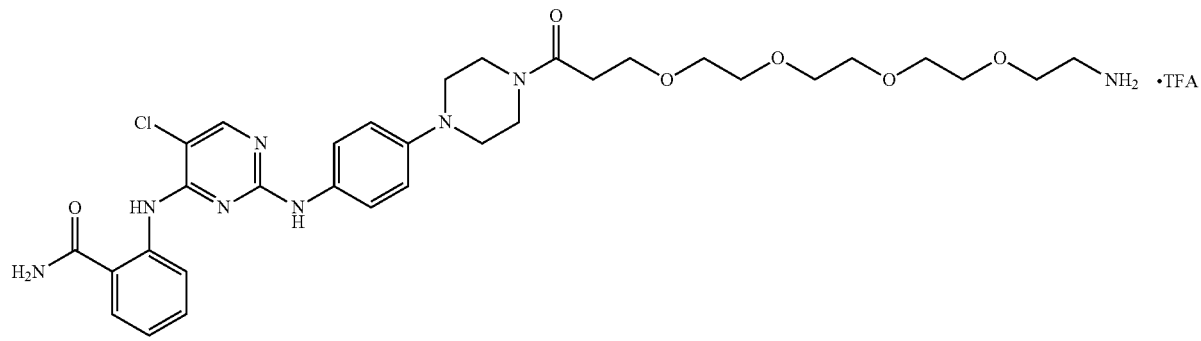 [SMILES: NCCOCCOCCOCCOCCC(=O)N1CCN(c2ccc(Nc3ncc(Cl)c(Nc4ccccc4C(N)=O)n3)cc2)CC1]

Tert-butyl (15-(4-(4-((4-((2-carbamoylphenyl)amino)-5-chloropyrimidin-2-yl)amino)phenyl)piperazin-1-yl)-15-oxo-3,6, 9,12-tetraoxapentadecyl)carbamate (100.0 mg, 0.13 mmol) in DCM (3.0 mL) was treated with 300 μL of triisopropylsilane followed by trifluoroacetic acid (3 mL). The mixture was capped and allowed to stir for 1 hr. Volatiles were removed under reduced pressure, and the mixture dried under high vacuum. The residue was treated with diethyl ether, giving a red solid, was decanted and an additional portion of diethyl ether was added and decanted before drying the residue under hi vacuum overnight. The resulting solid was dissolved in 1:1:0.01 acetonitrile, water, trifluoroacetic acid and subjected to reverse phase-preparative HPLC, affording the desired product (67.9 mg, 66.7%) as a yellow solid. MS (ESI+) m/z calc'd for [M+H]$^+$ $C_{32}H_{44}ClN_8O_6$: 671.31, found 671.35.

Example 10

Compound CC-1804

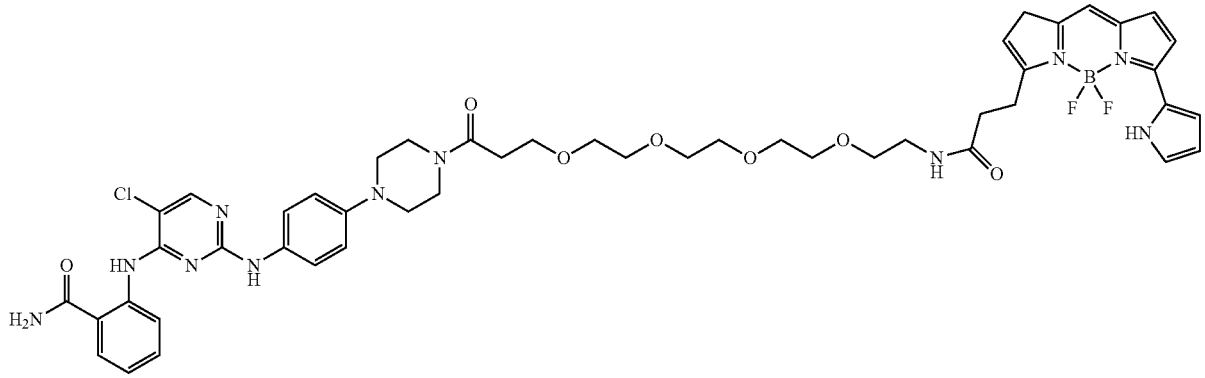

2-((2-((4-(4-(1-amino-3,6,9,12-tetraoxapentadecan-15-oyl)piperazin-1-yl)phenyl)amino)-5-chloropyrimidin-4-yl)amino)benzamide-TFA (20.0 mg, 0.03 mmol) was taken up in 5 ml anhydrous D1DMF with stirring. To the mixture, N,N-diisopropylethylamine (22.2 μL, 0.03 mmol) was added, and the reaction allowed to stir for 10 min. Nano-BRET™ 590 SE tracer (Promega Corp.; 16.3 mg, 0.038 mmol) was added, and the reaction stirred in the dark for 90 min. Volatiles were removed under reduced pressure giving a blue film that was taken up in 8 mL of 1:1:0.01 acetonitrile, water, trifluoroacetic acid and subjected to reverse phase preparative HPLC purification to give the product (24.8 mg, 99.0%) as a blue solid. MS (ESI+) m/z calc'd for [M+H]$^+$ C$_{48}$H$_{57}$BC$_1$F$_2$N$_{11}$O$_7$: 983.31, found 983.42.

Example 11

Experiments were conducted during development of embodiments herein to derive a comprehensive analysis of intracellular kinase target engagement using NanoBRET™ tracers derived from CC-1294 versus NanoBRET™ tracers derived from novel inhibitors. In wells of 96-well plates, 20,000 HEK293 cells/well were transfected with pFN31K and pFN32K plasmids for expression of kinase/NanoLuc® (Nluc) fusion proteins. Transfections were performed using 3:1 FuGENE HD:plasmid ratios. 24 hours post transfection, cells were treated for 2 hours in the presence of 0.5 uM CC-1804, CC-1852, or 1 uM CC-1294. After incubation, NanoBRET™-Target Engagement (TE) substrate/inhibitor solution was added to a final concentration of 1×. NanoBRET was measured on a Glomax® Discover plate reader. To determine relative BRET signals, BRET arising from the tracer was divided by BRET in the absence of tracer. As demonstrated in FIG. 1A-B, unexpectedly broad spectrum target engagement/kinase profiling was observed with CC-1804 and CC-1852 compared to CC-1294.

Example 12

Figure 2B:
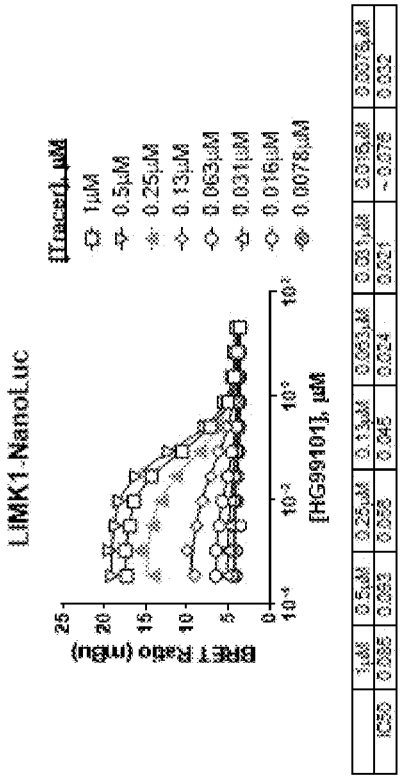
Figure 2B:
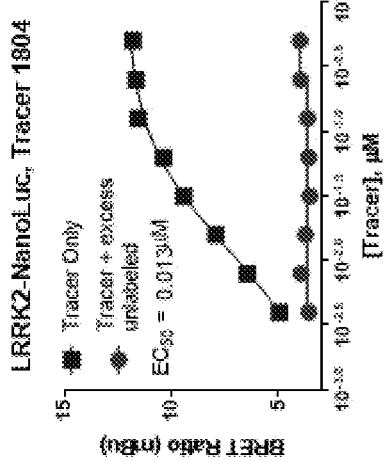
Figure 2B:
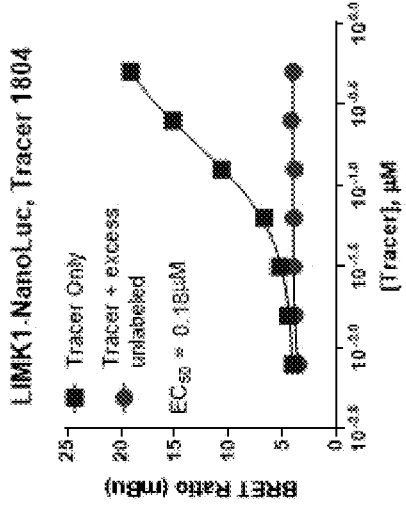
Figure 2B:
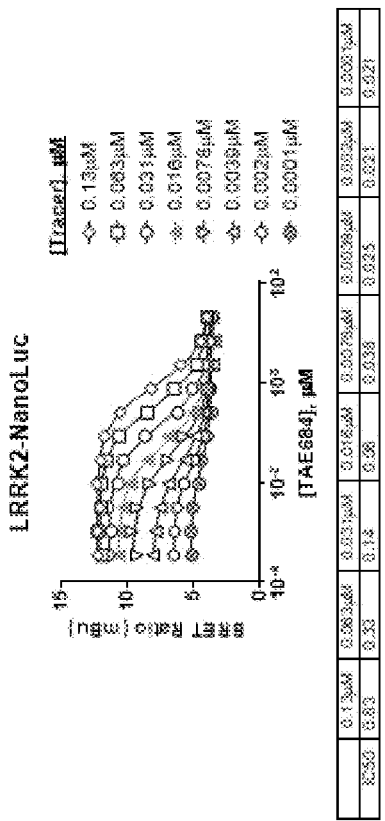
Figure 2C:
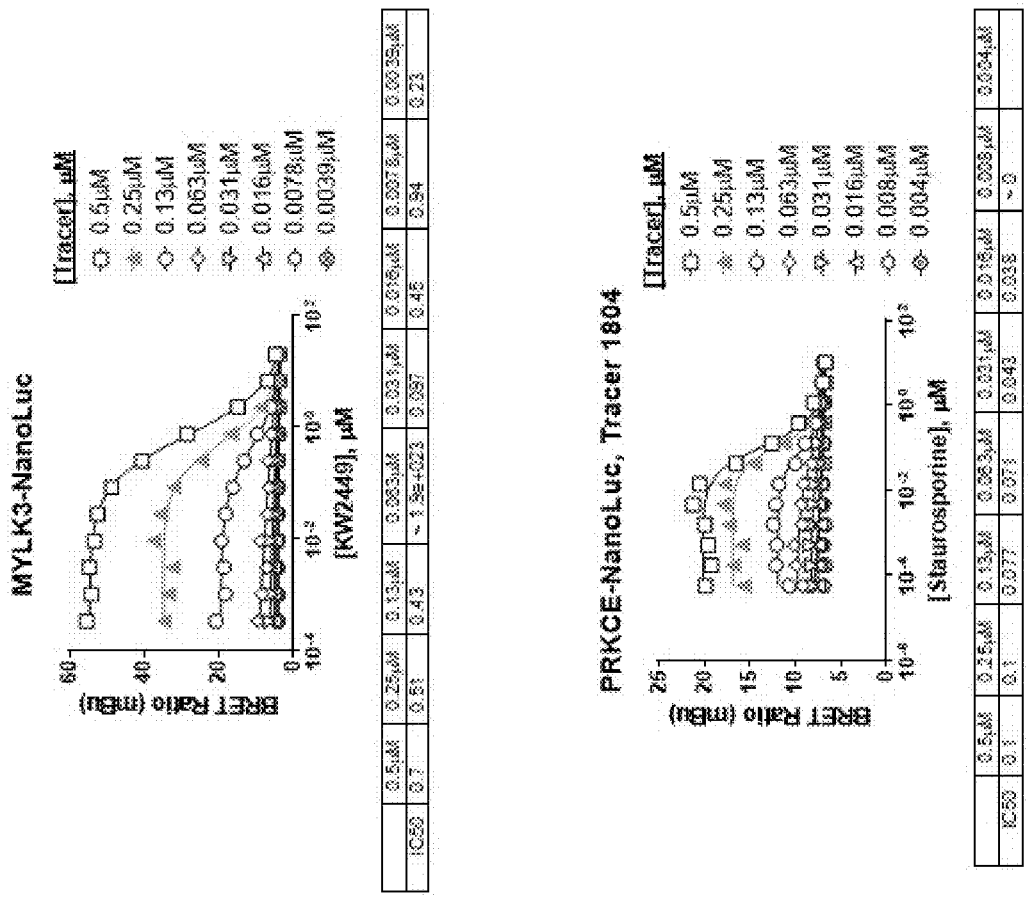

Experiments were conducted during development of embodiments herein to demonstrate novel live cell target engagement assays uniquely enabled by CC-1804, which are not enabled by CC-1294. In wells of 96-well plates, 20,000 HEK293 cells/well were transfected with pFN31K and pFN32K plasmids for expression of kinase/NanoLuc® (Nluc) fusion proteins. Transfections were performed using 3:1 FuGENE HD:plasmid ratios. 24 hours post transfection, cells were treated for 2 hours in the presence of varying concentrations of tracer and varying concentrations of control inhibitor as indicated in FIG. 2A-C. After incubation, NanoBRET™-TE substrate/inhibitor solution was added to a final concentration of 1×, and BRET was measured on a Glomax® Discover plate reader.

Example 13

Figure 3:
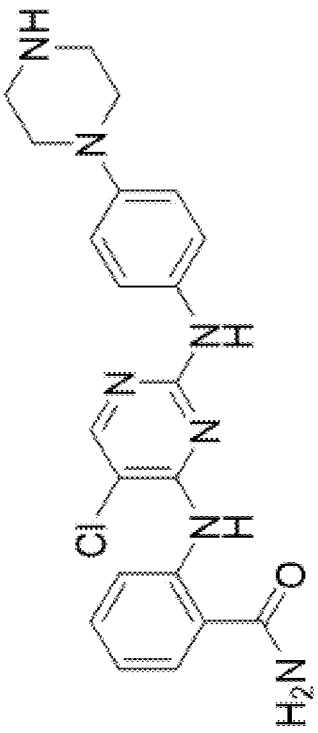
FIG. 3. The chemical structures of broad-spectrum kinase binding agents CC-1852, CC-1861 and CTx-02994885.
Figure 3:
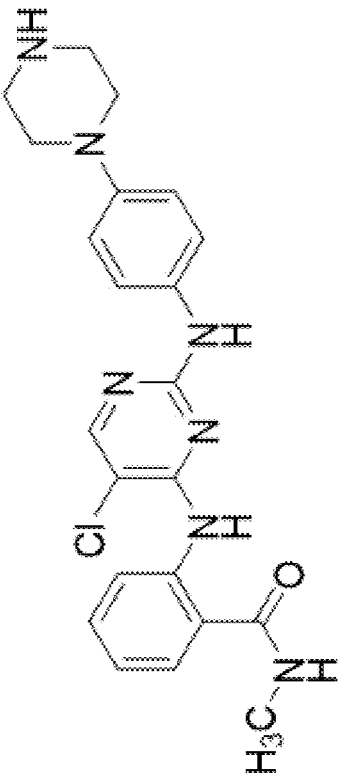
Figure 4:
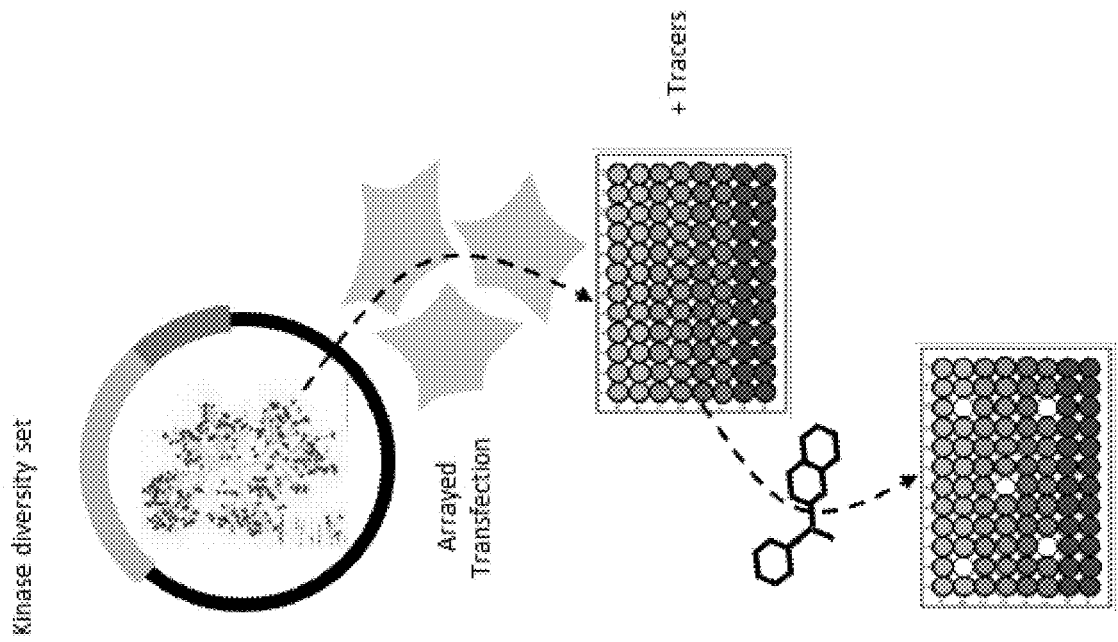
FIG. 4. Illustration of NanoBRET™ target engagement work flow for determining target engagement for CC-1861 vs CTx-0294885. NanoBRET™ tracers were introduced at approximately 50% target occupancy values. Occupancy of the test compounds are determined by competitive displacement of the NanoBRET™ Tracers in live cells FIG. 5. A condensed heat map of target engagement potency in live cells for 300 nM CC-1861 vs CTx-0294885. Target engagement was measured by competitive displacement against NanoBRET™ tracers in living HEK293 cells. Red indicates higher occupancy, and green indicates lower occupancy.

Experiments were conducted during development of embodiments herein to analyze the broad-spectrum intracellular kinase target engagement of parental molecules CC-1861 versus CTx-0294885 (FIG. 3). In wells of 96-well plates, 20,000 HEK293 cells per well were transfected with kinase/Nluc fusions expressed from pFN31K and pFN32K plasmids. Transfections were performed using 3:1 FuGENE HD:plasmid ratios. 24 hours post transfection, cells were treated for 2 hours in the presence of NanoBRET™ tracers (K4, K5, K7, K8, K9, K10, K11) introduced at optimized concentrations in the presence of test compounds 300 nM CC-1861, 300 nM CTx-0294885, or 0.1% DMSO (vehicle). Analysis was also performed in using untagged Nluc to determine zero BRET (full occupancy control sample). After incubation, NanoBRET™-TE substrate/inhibitor solution was added to a final concentration of 1×. NanoBRET was measured on a Glomax® Discover plate reader. To generate raw BRET ratio values, the acceptor emission value (e.g. 610 nm) was divided by the donor emission value (e.g. 450 nm) for each sample.

Determine Fractional Occupancy with the following equation;

% Occupancy=[1−(X−Z)/(Y−Z)]*100 where X=BRET in the presence of the test compound and tracer, Y=BRET in the presence of tracer only (zero occupancy control), and Z=BRET for the full occupancy control (ie., BRET from the untagged Nluc fusion).

Figure 5:
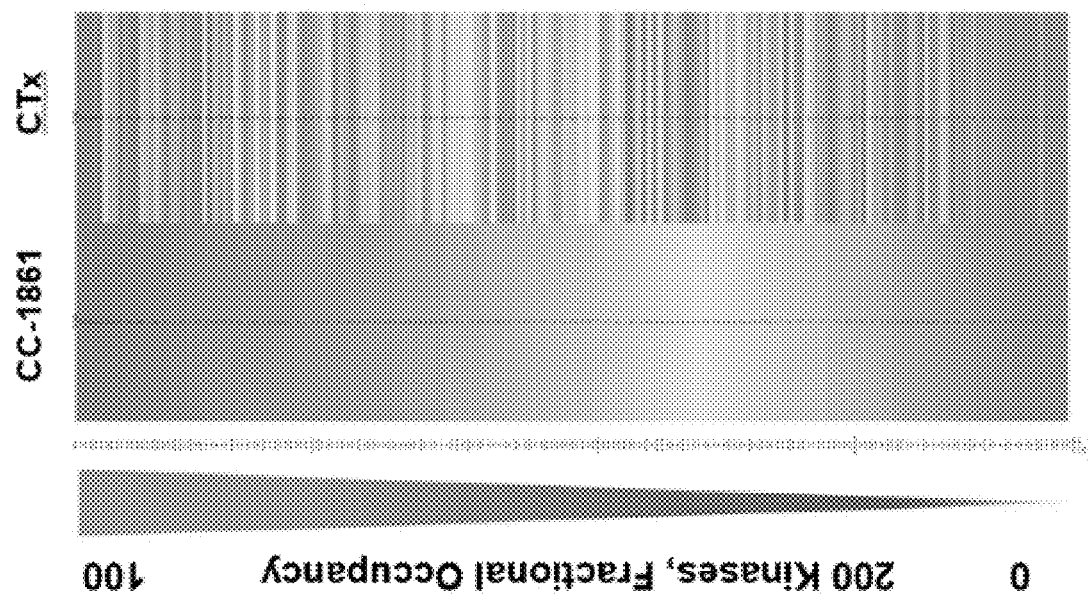

Of the 200 kinases evaluated 71 kinases preferred CC-1861 to CTx; only 4 kinase preferred CTx over CC-1861 (FIG. 5).

Example 14

Experiments were conducted during development of embodiments herein to demonstrate the increased kinase affinity of unmodified CC-1861 versus CTx-0294885. In wells of 96-well plates, 20,000 HEK293 cells per well were transfected with kinase/Nluc fusions expressed from pFN31K and pFN32K plasmids. Transfections were performed using 3:1 FuGENE HD:plasmid ratios. 24 hours post transfection, cells were treated for 2 hours in the presence of tracer and varying concentration of control inhibitor indicated. After incubation, NanoBRET™-TE substrate/inhibitor solution was added to a final concentration of 1×, and BRET was measured on a Glomax® Discover plate reader.

Figure 7:
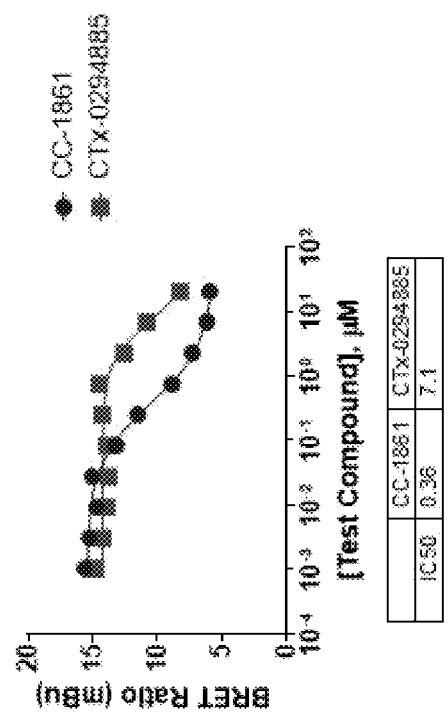
FIG. 7. Comparison of intracellular affinity for CC-1861 vs CTx-0294884. NanoBRET™ assays were run by competitive displacement of NanoBRET™ tracers in living HEK293 cells. Intracellular affinity of CC-1861 was stronger than CTx-0294885 for three of the four targets tested.
Figure 7:
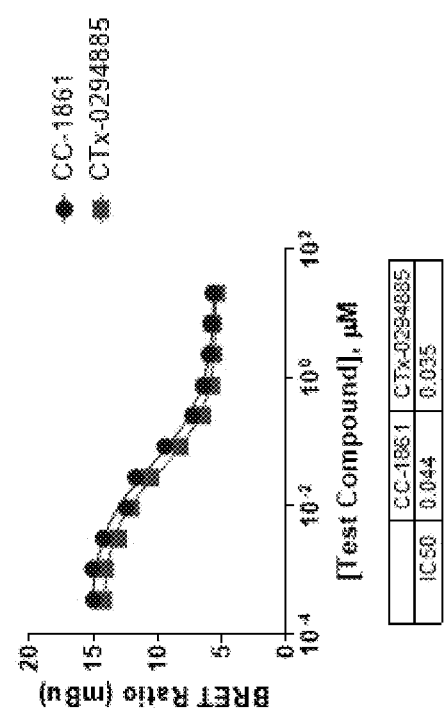
Figure 7:
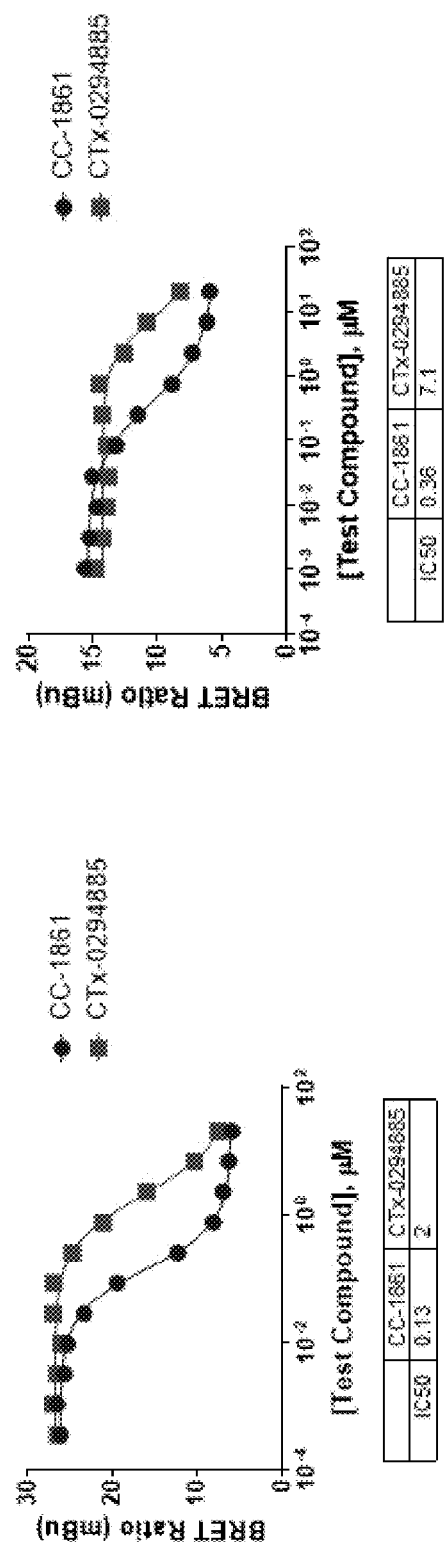
Figure 7:
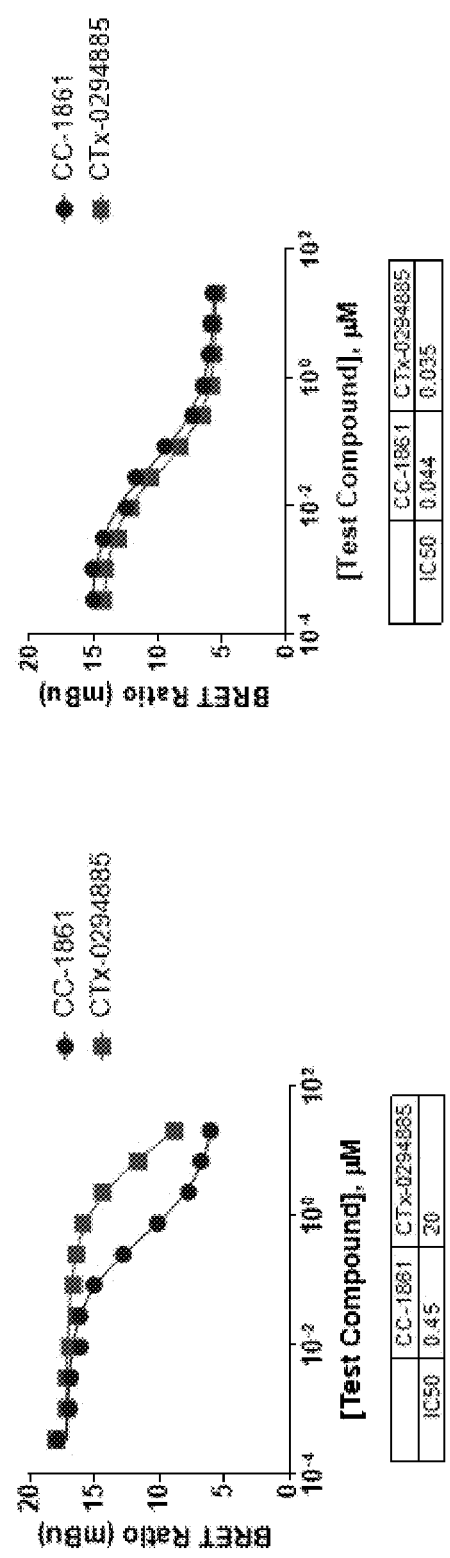

CC-1861 shows increased inhibitor potency compared to CTx (FIG. 7). CC-1861 had greater than 0.5 log shift in potency improvement compared to the CTx-0294885 for many of the kinases screened thus demonstrating CC-1861 as an improved broad-spectrum kinase binding agent (FIG. 8).

Example 15

2-((5-chloro-2-((4-(piperazin-1-yl)phenyl)amino)pyrimidin-4-yl)amino)benzamide

Compound CC-1861

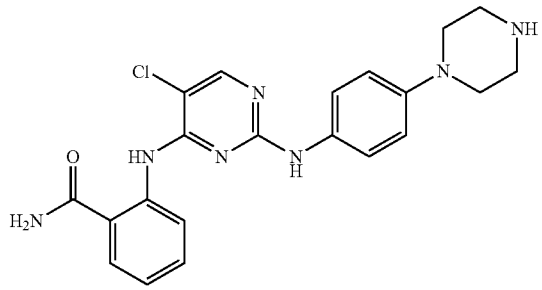 [SMILES: NC(=O)c1ccccc1Nc1nc(Nc2ccc(N3CCNCC3)cc2)ncc1Cl]

Tert-butyl 4-(4-((4-((2-carbamoylphenyl)amino)-5-chloropyrimidin-2-yl)amino)phenyl)piperazine-1-carboxylate (90.0 mg, 0.17 mmol) in DCM (2.0 mL) was treated with triisopropylsilane (200 uL, 0.17 mmol) followed by trifluoroacetic acid (2.0 mL). The capped mixture was stirred for 3 hrs, and volatiles removed under reduced pressure to give a yellow oil. The residue was treated with 20 mL diethyl ether giving a white solid. The ether was decanted, and the resulting white solid triturated with a 20 mL portion of fresh diethyl ether. The ether was decanted, and the resulting white solid dried under high vacuum for 20 min. The residue was dissolved in methanol (10 mL) and treated with 45 mg of potassium carbonate. The resulting mixture was stirred for 1 hr, absorbed on celite, and subjected to flash silica gel chromatography using a gradient of methanol in DCM. Product containing fractions were pooled and concentrated to give the product (50.0 mg, 68.7%) as a white solid. MS (ESI+) m/z calc'd for [M+H]+ C21H22ClN7O: 424.17, found 424.24.

SEQUENCE LISTING

```
Sequence total quantity: 6
SEQ ID NO: 1            moltype = AA   length = 5
FEATURE                 Location/Qualifiers
source                  1..5
                        mol_type = protein
                        organism = synthetic construct
SEQUENCE: 1
HHHHH                                                                    5

SEQ ID NO: 2            moltype = AA   length = 6
FEATURE                 Location/Qualifiers
source                  1..6
                        mol_type = protein
                        organism = synthetic construct
SEQUENCE: 2
HHHHHH                                                                   6

SEQ ID NO: 3            moltype = AA   length = 10
FEATURE                 Location/Qualifiers
source                  1..10
                        mol_type = protein
                        organism = synthetic construct
SEQUENCE: 3
EQKLISEEDL                                                              10

SEQ ID NO: 4            moltype = AA   length = 8
FEATURE                 Location/Qualifiers
source                  1..8
                        mol_type = protein
                        organism = synthetic construct
SEQUENCE: 4
DYKDDDDK                                                                 8

SEQ ID NO: 5            moltype = AA   length = 8
FEATURE                 Location/Qualifiers
source                  1..8
                        mol_type = protein
                        organism = synthetic construct
SEQUENCE: 5
WSHPQFEK                                                                 8

SEQ ID NO: 6            moltype = AA   length = 9
FEATURE                 Location/Qualifiers
source                  1..9
                        mol_type = protein
                        organism = synthetic construct
SEQUENCE: 6
YPYDVPDYA                                                                9
```

The invention claimed is:

1. A broad-spectrum kinase binding agent attached to a fluorophore, comprising a kinase binding moiety of formula:

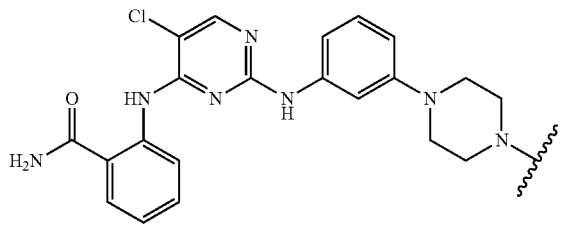 [SMILES: *N1CCN(c2cccc(Nc3ncc(Cl)c(Nc4ccccc4C(N)=O)n3)c2)CC1]

attached to the fluorophore.

2. A broad-spectrum kinase binding agent attached to a fluorophore, comprising a kinase binding moiety of formula:

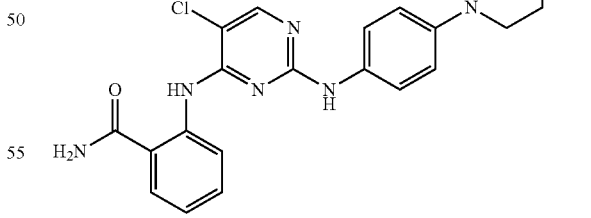

attached to the fluorophore.

3. The broad-spectrum kinase binding agent of claim 1, wherein the kinase binding moiety is attached to the fluorophore directly.

4. The broad-spectrum kinase binding agent of claim 1, wherein the kinase binding moiety is attached to the fluorophore via a linker.

5. The broad-spectrum kinase binding agent of claim 4, wherein the linker comprises —[(CH$_2$)$_2$O]$_n$—, wherein n is 1-20.

6. The broad-spectrum kinase binding agent of claim 5, wherein the linker is attached to the kinase binding moiety and/or the fluorophore by an amide bond.

7. The broad-spectrum kinase binding agent of claim 1, comprising a structure of:

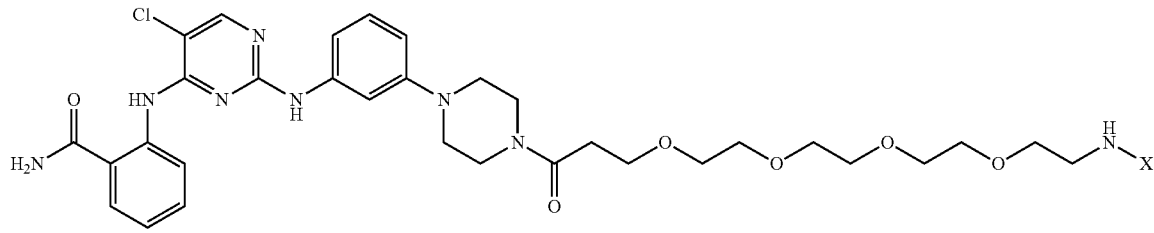

wherein X is the fluorophore.

8. The broad-spectrum kinase binding agent of claim 7, comprising a structure of:

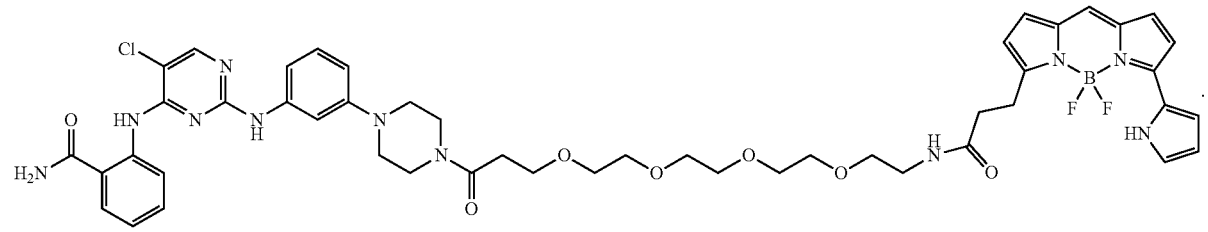

9. The broad-spectrum kinase binding agent of claim 2, comprising a structure of:

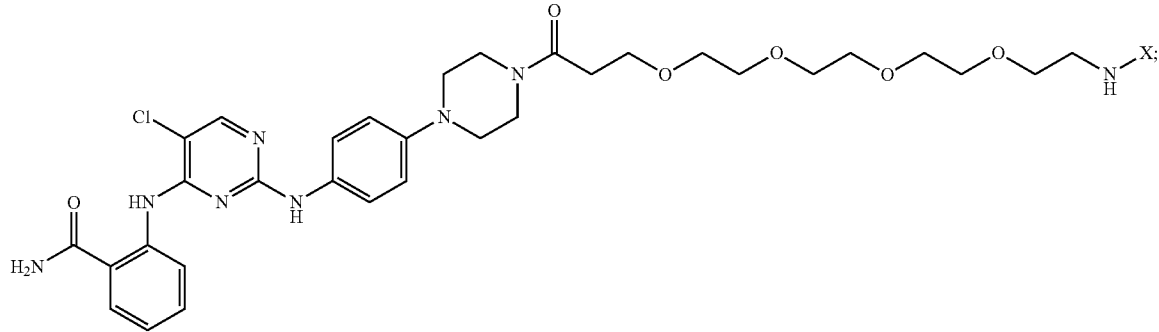

wherein X is the fluorophore.

10. The broad-spectrum kinase binding agent of claim 9, comprising a structure of:

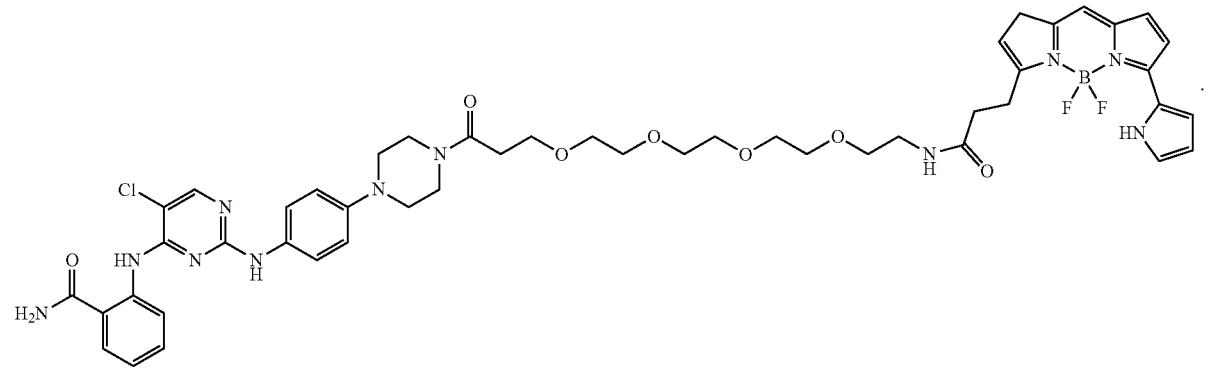

11. The broad-spectrum kinase binding agent of claim 2, wherein the kinase binding moiety is attached to the fluorophore directly.

12. The broad-spectrum kinase binding agent of claim 2, wherein the kinase binding moiety is attached to the fluorophore via a linker.

13. The broad-spectrum kinase binding agent of claim 12, wherein the linker comprises —[(CH$_2$)$_2$O]$_n$—, wherein n is 1-20.

14. The broad-spectrum kinase binding agent of claim 13, wherein the linker is attached to the kinase binding moiety and/or the fluorophore by an amide bond.

* * * * *